(12) United States Patent
Talisman et al.

(10) Patent No.: US 10,849,955 B2
(45) Date of Patent: Dec. 1, 2020

(54) METHODS OF TREATING PANCREATIC CANCER USING GPCR ANTAGONISTS

(71) Applicant: City of Hope, Duarte, CA (US)

(72) Inventors: Tijana Talisman, Glendora, CA (US); Sunetra Biswas, Santa Monica, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 15/719,421

(22) Filed: Sep. 28, 2017

(65) Prior Publication Data

US 2018/0153953 A1 Jun. 7, 2018

Related U.S. Application Data

(60) Provisional application No. 62/401,111, filed on Sep. 28, 2016.

(51) Int. Cl.

| | |
|---|---|
| *A61K 31/485* | (2006.01) |
| *A61K 38/08* | (2019.01) |
| *A61K 38/10* | (2006.01) |
| *A61K 38/12* | (2006.01) |
| *A61K 38/16* | (2006.01) |
| *A61P 1/18* | (2006.01) |
| *A61P 35/00* | (2006.01) |
| *G01N 33/574* | (2006.01) |

(52) U.S. Cl.
CPC ............ *A61K 38/08* (2013.01); *A61K 31/485* (2013.01); *A61K 38/10* (2013.01); *A61K 38/12* (2013.01); *A61K 38/16* (2013.01); *A61P 1/18* (2018.01); *A61P 35/00* (2018.01); *G01N 33/57438* (2013.01); *G01N 2333/726* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,861,760 | A | 8/1989 | Mazuel et al. |
| 4,911,920 | A | 3/1990 | Jani et al. |
| 5,212,162 | A | 5/1993 | Missel et al. |
| 5,403,841 | A | 4/1995 | Lang et al. |
| 5,846,934 | A | 12/1998 | Bass et al. |
| 5,925,618 | A | 7/1999 | Baumbach et al. |
| 8,206,722 | B2 | 6/2012 | Vranic et al. |
| 2002/0016298 | A1 | 2/2002 | Hay et al. |
| 2002/0091125 | A1 | 7/2002 | Hay et al. |
| 2008/0299040 | A1 | 12/2008 | Rivier et al. |
| 2009/0004195 | A1 | 1/2009 | Vranic et al. |

FOREIGN PATENT DOCUMENTS

| | | |
|---|---|---|
| EP | 863156 A1 | 9/1998 |
| EP | 1086947 A1 | 3/2001 |
| EP | 1149842 A2 | 10/2001 |
| EP | 1149842 A3 | 10/2001 |
| WO | WO-01/081408 A2 | 11/2001 |
| WO | WO-01/081408 A3 | 11/2001 |
| WO | WO-2003/090677 A2 | 11/2003 |
| WO | WO-2003/090677 A3 | 11/2003 |
| WO | WO-2006/052723 A2 | 5/2006 |
| WO | WO-2006/052723 A3 | 5/2006 |
| WO | WO-2008/048942 A2 | 4/2008 |
| WO | WO-2008/048942 A3 | 4/2008 |
| WO | WO-2009/129311 A2 | 10/2009 |
| WO | WO-2009/129311 A3 | 10/2009 |

OTHER PUBLICATIONS

Singleton et al., "The Mu Opioid Receptor: a new target for cancer therapy?", Cancer 121:2681-8 (published online Jun. 4, 2015) (Year: 2015).*

Tulipano et al, "The somatostatin subtype-2 receptor antagonist, BIM-23627, improves the catabolic effects induced by long-term glucocorticoid treatment in the rat," Regul. Peptides 125:85-2 (2005) (Year: 2005).*

Billadeau, D.D. et al. (2006). "Characterization of the CXCR4 signaling in pancreatic cancer cells," *In J Gastrointest Cancer* 37(4):110-119.

Kailey, B. et al. (Nov. 1, 2012, e-published Aug. 28, 2012). "SSTR2 is the functionally dominant somatostatin receptor in human pancreatic β- and α-cells," *Am J Physiol Endocrinol Metab* 303(9):E1107-E1116.

Korc, M. et al. (Oct. 1992). "Overexpression of the epidermal growth factor receptor in human pancreatic cancer is associated with concomitant increases in the levels of epidermal growth factor and transforming growth factor alpha," *J Clin Invest* 90(4):1352-1360.

Moore, M.J. et al. (May 2007, e-published Apr. 23, 2007). "Erlotinib plus gemcitabine compared with gemcitabine alone in patients with advanced pancreatic cancer: a phase III trial of the National Cancer Institute of Canada Clinical Trials Group," *J Clin Oncol* 25(15):1960-1966.

Pfeiffer, M. et al. (May 31, 2002, e-published Mar. 14, 2002). "Heterodimerization of somatostatin and opioid receptors cross-modulates phosphorylation, internalization, and desensitization," *J Biol Chem* 277(22):19762-19772.

Rozenfeld, R. et al. (Aug. 2007, e-published Mar. 23, 2007). "Receptor heterodimerization leads to a switch in signaling: beta-arrestin2-mediated ERK activation by mu-delta opioid receptor heterodimers," *FASEB J* 21(10:2455-2465.

Von Hoff, D.D. et al. (Oct. 31, 2013, e-published Oct. 16, 2013). "Increased survival in pancreatic cancer with nab-paclitaxel plus gemcitabine," *N Engl J Med* 369(18):1691-1703.

(Continued)

*Primary Examiner* — Julie Ha
*Assistant Examiner* — Kristina M Hellman
(74) *Attorney, Agent, or Firm* — Mintz, Levin, Cohn, Ferris, Glovsky and Popeo, P.C.

(57) ABSTRACT

Provided herein are, inter alia, compositions and methods for the treatment of cancer and inhibition of metastasis. The compositions include a μ-opioid receptor (MOR) polypeptide and a somatostatin receptor 2 (SSTR2) polypeptide, wherein the MOR polypeptide is bound to a MOR antagonist and the SSTR2 polypeptide is bound to a SSTR2 antagonist. The compositions and methods provided herein are, inter alia, useful to treat pancreatic cancer.

8 Claims, 49 Drawing Sheets

Specification includes a Sequence Listing.

(56) References Cited

OTHER PUBLICATIONS

Yuan, Y. et al. (May 1, 2013). "A Bivalent Ligand Targeting the Putative Mu Opioid Receptor and Chemokine Receptor CCR5 Heterodimers: Binding Affinity versus Functional Activities," *MedChemComm* 4(5):847-851.

Zheng, X. et al. (Nov. 26, 2015, e-published Nov. 11, 2015). "Epithelial-to-mesenchymal transition is dispensable for metastasis but induces chemoresistance in pancreatic cancer," *Nature* 527(7579):525-530.

\* cited by examiner

METHODS OF TREATING PANCREATIC CANCER USING GPCR ANTAGONISTS

CROSS-REFERENCES TO RELATED APPLICATIONS

This application claims priority to U.S. Provisional Application No. 62/401,111, filed Sep. 28, 2016, which is hereby incorporated by reference in its entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 048440-626001US_SEQUENCE_LISTING_ST25_1, created Dec. 16, 2019, 16,384 bytes, machine format IBM-PC, MS Windows operating system, is hereby incorporated by reference.

BACKGROUND

Pancreatic ductal adenocarcinoma (PDAC) is the fourth leading cancer-related cause of death in the United States (Howlader N, 2014). The high lethality of PDAC correlates to high rates of metastasis and is partially coupled to limited treatment options (Oberstein and Olive, 2013). Despite improvements in conventional therapies such as surgery, radiation, and chemotherapy (Von Hoff et al., 2013), it is estimated that approximately 93% of PDAC patients will succumb to the disease within 5 years of diagnosis (Howlader N, 2014). It is therefore imperative to identify new therapeutic targets for PDAC.

Evidence has recently emerged that G-protein-coupled receptors (GPCRs) may play a critical role in pancreatic tumorigenesis. However, despite significant interest in GPCRs and their role in PDAC, the number of PDAC targets and pharmacological agents aimed towards such targets is sparse. The compositions and methods provided herein address these and other needs in the art.

BRIEF SUMMARY OF INVENTION

In a first aspect, a method of treating pancreatic cancer in a subject in need thereof is provided. The method includes administering to a subject a therapeutically effective amount of a SSTR2 antagonist, thereby treating pancreatic cancer in the subject.

In another aspect, a pharmaceutical composition including an SSTR2 antagonist, a MOR antagonist and a pharmaceutically acceptable excipient is provided.

In another aspect, a method of inhibiting metastasis in a subject in need thereof is provided. The method includes administering to a subject a therapeutically effective amount of a SSTR2 antagonist, thereby inhibiting metastasis in the subject.

In one aspect, a method of detecting an expression level of a SSTR2-MOR polypeptide complex in a subject that has or is at risk for developing pancreatic cancer is provided. The method includes (i) obtaining a biological sample from the subject; and (ii) determining an expression level of an SSTR2-MOR polypeptide complex.

In one aspect, a method of treating pancreatic cancer in a subject in need thereof is provided. The method includes (i) detecting an elevated level of an SSTR2-MOR polypeptide complex relative to a standard control; and (ii) when an elevated expression level of the SSTR2-MOR polypeptide complex is found relative to the standard control, administering to the subject an SSTR2 antagonist, thereby treating the subject.

In one aspect, there is provided a G-protein-coupled receptor (GPCR)-ligand conjugate including: (i) a Mu opioid receptor (MOR) polypeptide bound to a somatostatin receptor 2 (SSTR2) polypeptide; and (ii) a first antagonist bound to a MOR polypeptide or a SSTR2 polypeptide.

In another aspect, there is provided a method for treating pancreatic cancer in a subject in need thereof. The method includes administering to the subject a therapeutically effective amount of a MOR antagonist, thereby treating pancreatic cancer in the subject.

In another aspect, there is provided a method of inhibiting metastasis in a subject in need thereof. The method includes administering to the subject a therapeutically effective amount of a MOR antagonist, thereby inhibiting metastasis in the subject.

In one aspect, there is provided a G-protein-coupled receptor (GPCR)-ligand conjugate including: (i) a Mu opioid receptor (MOR) polypeptide bound to a MOR antagonist; and (ii) a somatostatin receptor 2 (SSTR2) polypeptide bound to a SSTR2 antagonist; wherein the MOR polypeptide and the SSTR2 polypeptide are bound together.

In another aspect, there is provided a method of treating pancreatic cancer in a subject in need thereof. The method includes administering to the subject a therapeutically effective amount of a SSTR2 antagonist, thereby treating pancreatic cancer in the subject.

In another aspect, there is provided a method of inhibiting metastasis in a subject in need thereof. The method includes administering to the subject a therapeutically effective amount of a SSTR2 antagonist, thereby inhibiting metastasis in the subject.

BRIEF DESCRIPTION OF THE DRAWINGS

FIG. 1A. Using the mRNA levels of GAPDH in pancreatic cell lines as a point of comparison, the relative mRNA levels of CXCR4, MOR, and SSTR2 were determined. Normal epithelial pancreatic cells, primary pancreatic cancer cell lines, and metastatic pancreatic cell lines are shown. Measurements from three independent experiments, each done in triplicate, were used. CHO-S cells were used as negative controls and MCF-7 cells as positive controls. Results are expressed as the average with standard deviation. All GPCRs show statistically increased expression in cancerous cell lines compared to normal pancreatic cells ($p \leq 0.02$). FIG. 1B. In the membrane fraction of pancreatic cell lines, the protein levels of CXCR4, MOR, and SSTR2 were determined. CHO-S cells were used as negative controls and MCF-7 cells as positive controls. Loading was validated with Na/K ATPase. Quantitation of GPCR protein levels in different cell lines from 3 independent experiments is shown in FIG. 18A. Images were cropped for clarity; full blots are given in FIG. 18B.

FIG. 2A. The distribution of SSTR2 and MOR was determined in a region of normal epithelial pancreatic cells; Scale bar, 2 µm. Peak centers are shown. FIG. 2B. The distribution of SSTR2 and MOR was determined in a region of PANC-1 cells; Scale bar, 2 µm. Overlap is evident. Peak centers are shown. FIG. 2C. Cross-correlation curves with s.e.m show co-localization between MOR and SSTR2 in both PANC-1 cells (diamonds, N=41 regions from 22 cells) and PANC-1 MCTS (triangles, N=40 regions from 21 cells). In contrast, co-localization was not observed in normal pancreatic epithelial cells (circles, N=50 regions from 21 cells). These results represent combined data obtained using two labeling schemes: 1) MOR detected with Alexa Fluor 647; SSTR2 detected with Atto 488 and, 2) MOR detected with Atto 488; SSTR2 detected with Alexa Fluor 647. Individual curves are given in FIG. 11. In all cases no long-range correlations were observed. FIG. 2D. Cell lysates from either normal pancreatic epithelial cells or PANC-1 cells were immunoprecipitated with anti-MOR antibody and immunoblotted with anti-SSTR2 antibody. SSTR2 was detected in the MOR immunoprecipitate in PANC-1 cell line.

FIG. 3A. The distribution of CXCR4 and MOR was determined in a region of normal pancreatic cells; Scale bar, 2 µm. Peak centers are shown. FIG. 3B. The distribution of CXCR4 and MOR was determined in a region of PANC-1 cells; Scale bar, 2 µm. Peak centers are shown. FIG. 3C. Cross-correlation curves with s.e.m show no co-localization between MOR and CXCR4 in PANC-1 cells (diamonds, N=32 regions from 14 cells), PANC-1 MCTS (triangles, N=20 regions from 12 cells), and normal pancreatic epithelial cells (circles, N=21 regions from 13 cells). In all cases no long-range correlations were observed. FIG. 3D. Cell lysates from either normal pancreatic epithelial cells or PANC-1 cells were immunoprecipitated with anti-MOR antibody and immunoblotted with anti-CXCR4 antibody. CXCR4 was not detected in the MOR immunoprecipitate in either cell line. Quantitation is shown in FIG. 18D.

FIG. 4A. The distribution of SSTR2 and MOR was determined in healthy pancreatic tissue margins; scale bar, 2 µm. Controls with blocking peptides are given in inset; scale bar, 5 µm. Peak centers are shown. FIG. 4B. The distribution of SSTR2 and MOR was determined in matching cancerous pancreatic tissue; scale bar, 2 µm. Controls with blocking peptides are given in the inset; scale bar, 5 µm. Overlap is evident. Peak centers are shown. FIG. 4C. Cross-correlation with standard error of the mean demonstrates co-localization between MOR and SSTR2 in tumor tissue: triangles (Patient 1, N=9), circles (Patient 2, N=8) and diamonds (Patient 3, N=15). Co-localization was not detected in matching healthy tissue: triangles (Patient 1, N=7), circles (Patient 2, N=8) and diamonds (Patient 3, N=14). Only areas positive for keratin 8 and 18 were used for quantification. In all cases no long-range correlations are observed.

FIG. 5A. After treating either normal epithelial pancreatic cells or PANC-1 cells with agonists, phosphorylation of ERK1/2 and EGFR in cell lysates was analyzed (Western blot detection). The agonist treatments were 10 nM dermorphin; 10 nM L-054,264; or 10 nM dermorphin with 10 nM L-054,264. Treatment time periods are indicated. Images were cropped for clarity; large regions of representative original images are provided in FIG. 18E. FIG. 5B. Using Bio-rad Image Lab software, the amount of ERK1/2 or EGFR phosphorylation in each lane was quantified. The data was expressed as a ratio of either pERK1/2 over total ERK1/2 or pEGFR over total EGFR and averaged. Results were normalized (the maximum response for dermorphin in PANC-1 cells is taken as 100%) and presented with standard error. Dermorphin treatment is presented with diamond data point markers; L-054,264 treatment is presented with triangle data point markers; and combined treatment is presented with circle data point markers. $p<0.01$ (obtained using the single tail T-test) between dermorphin activation and either L-054,264 or combined L-054,264 and dermorphin activation are indicated with the star. For pEGFR/EGFR, corresponding $p<0.01$ in all cases. FIG. 5C. Confocal imaging was used to determine pERK1/2 localization in cells. The combined MOR and SSTR2 agonists targeted pERK1/2 to nucleus in normal pancreatic cells (low levels) and to cytoplasm in PANC-1 cells (high levels). Single agonists targeted pERK1/2 to nucleus in normal pancreatic cells (low levels) and to nucleus in PANC-1 cells (high levels). Scale bars 10 µm. FIG. 5D. After treating PANC-1 cells with agonists (10 nM dermorphin; 10 nM L-054,264; or 10 nM dermorphin with 10 nM L-054,264) for indicated periods of time, nuclear and cytoplasmic cell fractions were separated and levels of pERK1/2 and pRSK were observed using Western blots. Large regions of representative original images are provided in FIG. 18F. FIG. 5E. After treating normal pancreatic and PANC-1 cells with agonists (10 nM dermorphin; 10 nM L-054,264; or 10 nM dermorphin with 10 nM L-054,264) for 24 h, mRNA levels of N-cadherin, MMP-9, vimentin and E-cadherin were measured compared to their levels in untreated cells. For each group of four bars, bars from left to right represent data for N-cadherin, E-cadherin, MMP-9, and vimentin. Measurements from three independent experiments, each done in duplicate, were used. Results are expressed as the average with standard deviation.

FIG. 6A. Using dSTORM, MOR was imaged in PANC-1 cells. MOR was detected using a selective primary antibody and a tagged secondary antibody; scale bar, 5 µm. A magnified region is given in the bottom right; scale bar, 500 nm. A blocking peptide control is given in the upper right; scale bar, 5 µm. FIG. 6B. Using dSTORM, SSTR2 was imaged in PANC-1 cells. SSTR2 was detected using a selective primary antibody and a tagged secondary antibody; scale bar, 5 µm. A magnified region is given in the bottom right; scale bar, 500 nm. A blocking peptide control is given in the upper right; scale bar, 5 µm. FIG. 6C. Using dSTORM, CXCR4 was imaged in PANC-1 cells. CXCR4 was detected using a selective primary antibody and a tagged secondary antibody; scale bar, 5 µm. A magnified region is given in the bottom right; scale bar, 500 nm. A blocking peptide control is given in the upper right; scale bar, 5 µm. FIG. 6D. Schematic representation of the sequence overlay for human MOR, SSTR2, and CXCR4. The blocking peptide sequence (C-terminus for MOR and SSTR2; N-terminus for CXCR4) is boxed. For SSTR2, only the region of the sequence where blocking peptide is found is disclosed and highlighted. The upper MOR sequence is SEQ ID NO:3, the upper SSTR2 sequence is SEQ ID NO:4, the upper CXCR4 sequence is SEQ ID NO:5, the lower MOR sequence is SEQ ID NO:6, the lower SSTR2 sequence is SEQ ID NO:7, and the lower CXCR4 sequence is SEQ ID NO:8. Normalized Gaussians are shown throughout. Applicants confirmed that they were imaging cells using a transmission light source. Identical imaging and processing conditions were used. Images were inverted for clarity.

FIG. 7A. Western blot images confirm that CXCR4 is largely absent in PANC-1/CXCR4si cells; MOR is largely absent in PANC-1/MORsi cells; and SSTR2 is largely absent in PANC-1/SSTR2si cells. Other PANC-1 derived cell lines have unperturbed levels of the three GPCRs. Full blots are shown in FIG. 18C. FIG. 7B. As compared to levels in parental PANC-1 cells, the relative amounts of CXCR4, MOR, and SSTR2 mRNA were determined in PANC-1 derived cells. Results were obtained from three independent experiments, each done in triplicate. CHO-S cells were used as negative controls and MCF-7 cells as positive controls. Results are expressed as the average with standard deviation. FIG. 7C. CXCR4, MOR, and SSTR2 were detected with selective primary and tagged secondary antibodies in PANC-1 NS control cells. Magnified regions are shown; scale bar, 2 µm. PANC-1/CXCR4si, PANC-1/MORsi, and PANC-1/SSTR2si cells show no appreciable antibody binding (corresponding insets, scale bar 5 µm). Normalized Gaussians are shown throughout. Identical imaging and processing conditions were used. Images were inverted for clarity.

FIG. 8A. The distribution of SSTR2 and MOR was determined in normal pancreatic cells. FIG. 8B. The distribution of SSTR2 and MOR was determined in PANC-1 cells. Overlap is evident. Scale bar for full areas (top panels), 5 µm. Scale bar for magnified areas (middle and bottom panels), 100 nm. Top panel, all peak centers detected by NIS-Elements are shown. Middle panel, peak centers detected by NIS-Elements are shown; erode function in ImageJ was used to make peaks more visible. Bottom panel, normalized Gaussian rendering is shown. Identical imaging and processing conditions were used. Images were inverted for clarity.

FIG. 9A. The distribution of SSTR2 and MOR was determined in a region of PANC-1 MCTS. Overlap is evident; scale bar, 2 µm. FIG. 9B. Prior to dSTORM imaging, MOR and SSTR2 blocking peptides along with the respective primary antibodies were applied to PANC-1 MCTS. Subsequently, labeled secondary antibodies were used as before and imaging was performed. Negligible fluorescence is observed with blocking peptides; scale bar, 5 µm. FIG. 9C. The distribution of CXCR4 and MOR was determined in a region of PANC-1 MCTS; scale bar, 2 µm. FIG. 9D. Prior to dSTORM imaging, MOR and CXCR4 blocking peptides along with the respective primary antibodies were applied to PANC-1 MCTS. Subsequently, labeled secondary antibodies were used as before and imaging was performed. Negligible fluorescence is observed with blocking peptides; scale bar, 5 µm. Applicants confirmed they were imaging MCTS using a transmission light source. Identical imaging and processing conditions were used. Peak centers, detected by NIS-Elements, are shown throughout; erode function in ImageJ was used to make peaks more visible. Images were inverted for clarity.

FIG. 10A. MOR cluster radius in normal pancreatic cells (top, N=21 cells); cancerous PANC-1 cells (middle, N=22 cells); PANC-1 MCTS (bottom, N=21 cells). MOR was detected with either Atto 488 or Alexa Fluor 647. FIG. 10B. SSTR2 cluster radius in normal pancreatic cells (top, N=21 cells); cancerous PANC-1 cells (middle, N=22 cells); PANC-1 MCTS (bottom, N=21 cells). SSTR2 was detected with either Atto 488 or Alexa Fluor 647. FIG. 10C. CXCR4 cluster radius in normal pancreatic cells (top, N=13 cells); cancerous PANC-1 cells (middle, N=13 cells); PANC-1 MCTS (bottom, N=14 cells). CXCR4 was detected with Atto 488. FIG. 10D. Average cluster radius and cluster circularity for MOR, SSTR2, and CXCR4; * denotes $p \leq 0.02$. FIG. 10E. MOR cluster radius in normal tissue (top, N=17 cells) and cancerous tissue (bottom, N=19 cells) from 3 patients. FIG. 10F. SSTR2 cluster radius in normal tissue (top, N=17 cells) and cancerous tissue (bottom, N=19 cells) from 3 patients. FIG. 10G. Average cluster radius and cluster circularity for MOR and SSTR2 in patient samples; * denotes $p \leq 0.02$.

FIG. 11A. Cross-correlation curves show co-localization between MOR and SSTR2 in PANC-1 cells: for the dark gray diamonds, MOR was detected with Alexa Fluor 647 while SSTR2 was detected with Atto 488 (N=19 regions from 10 cells); for the light gray diamonds, MOR was detected with Atto 488 while SSTR2 was detected with Alexa Fluor 647 (N=22 regions from 12 cells). FIG. 11B. Cross-correlation curves show co-localization between MOR and SSTR2 in PANC-1 MCTS: for the dark gray triangles, MOR was detected with Alexa Fluor 647 while SSTR2 was detected with Atto 488 (N=19 regions from S6 MCTS); for the light gray triangles, MOR was detected with Atto 488 while SSTR2 was detected with Alexa Fluor 647 (N=21 regions from 10 MCTS). FIG. 11C. Cross-correlation curves show no co-localization between MOR and SSTR2 in normal pancreatic epithelial cells: for the dark gray circles, MOR was detected with Alexa Fluor 647 while SSTR2 was detected with Atto 488 (N=15 regions from 8 cells); for the light gray circles, MOR was detected with Atto 488 while SSTR2 was detected with Alexa Fluor 647 (N=36 regions from 13 cells). In all cases no long-range correlations were observed. Error bars represent standard error of the mean; region area size, 80 µm². For both combinations, 1) MOR and SSTR2 had significantly lower density ($p<0.05$) in normal pancreatic cells compared to PANC-1 cells; 2) SSTR2 had significantly lower density ($p<0.05$) in PANC-1 MCTS compared to PANC-1 cells.

FIG. 12A. The densities of R and G were equal to 20 receptors per µm²; 50% of the receptors were labeled (10 receptors detected in each channel per µm²). No homodimers (RR and GG) were present. Averaged number of appearances was 8 for both channels. FIG. 12B. The densities of R and G were equal to 20 receptors per µm²; 50% of the receptors were labeled (10 receptors detected in each channel per µm²). No homodimers (RR and GG) were present. Averaged number of appearances was 6 and 2 for R and G channels, respectively. FIG. 12C. The densities of R and G were equal to 20 receptors per µm²; 50% of the receptors were labeled (10 receptors detected in each channel per µm²). No homodimers (RR and GG) were present. Averaged number of appearances was 4 for both channels. FIG. 12D. The densities of R and G were equal to 50 receptors per µm²; 20% of the receptors were labeled (10 receptors detected in each channel per µm²). No homodimers (RR and GG) were present. Averaged number of appearances was 4 for both channels. FIG. 12E. The densities of R and G were equal to 20 receptors per µm²; 50% of the receptors were labeled (10 receptors detected in each channel per µm²). Receptors that were not involved in heterodimerization were organized as either monomers or homodimers with equal probability: i.e. 50% monomers (R and G) and 50% homodimers (RR and GG). Averaged number of appearances was 4 for both channels. FIG. 12F. The density of R was equal to 20 receptors per µm²; 50% of the receptors were labeled. The density of G was equal to 50 receptors per µm²; 20% of the receptors were labeled (10 receptors detected in each channel per µm²). No homodimers (RR and GG) were present. Averaged number of appearances was 4 for both channels. FIG. 12G. The densities of R and G were equal to 8 receptors per µm²; 50% of the receptors were labeled (4 receptors detected in each channel per µm²). No homodimers (RR and GG) were present. Averaged number of appearances was 4 for both channels. FIG. 12H. The densities of R and G were equal to 20 receptors per µm²; 20% of the receptors were labeled (4 receptors detected in each channel per µm²). No homodimers (RR and GG) were present. Averaged number of appearances was 4 for both channels.

FIG. 14A. Keratin 8 and 18 was detected in PANC-1 cells using a labeled secondary antibody; scale bar, 5 µm. FIG. 14B. There was no cross-talk between 405 and 488/647 channels in tissue samples. Keratin 8 and 18 was detected using selective primary and tagged secondary antibodies; MOR and SSTR2 were not affinity labeled. dSTORM imaging using 488 and 647 lasers was performed first (bottom); subsequently, images were acquired with a 405 laser (top). No appreciable 488/647 signal was observed; scale bar, 5 µm. When Keratin 8 and 18 was not affinity labeled, while MOR and SSTR2 were affinity labeled (using selective primary antibodies and labeled secondary antibodies), no signal from epithelial cells in tissue samples was observed in the 405 channel.

FIG. 15A. In the absence of agonist, MOR and SSTR2 were predominantly localized on the plasma membrane with appreciable co-localization. FIG. 15B. Addition of combined agonist resulted in MOR and SSTR2 receptor internalization. Gray scale images are shown on the bottom. Scale bars, 10 µm.

FIG. 16A. PANC-1 cells were treated with 10 nM dermorphin; 10 nM L-054,264; or 10 nM dermorphin with 10 nM L-054,264 for 3 or 30 min. FIG. 16B. Normal pancreatic cells were treated with 10 nM dermorphin; 10 nM L-054,264; or 10 nM dermorphin with 10 nM L-054,264 for 3 or 30 min. FIG. 16C. PANC-1 NS (top), PANC-1/MORsi (middle), and PANC-1/SSTR2si (bottom) cells were treated with 10 nM dermorphin and 10 nM L-054,264 for 3 min. Cells were turboGFP positive. FIG. 16D. PANC-1 cells were treated with 100 ng/ml CXCL12 or 100 ng/ml CXCL12 with 10 nM dermorphin for 3 or 30 min. FIG. 16E. Untreated PANC-1 cells (top) and normal pancreatic cells (bottom). FIG. 16F. Left, validation of PANC-1/β-arrestin2si cells with western blots; full blots are shown in FIG. 18G. Right, PANC-1/β-arrestin2si cells were treated with 10 nM dermorphin and 10 nM L-054,264 for 3 min. Cells were turboGFP positive.

FIG. 17A. Combined MOR and SSTR2 agonist treatment did not have a significant effect on mRNA levels of 4 markers in PANC-1/MORsi and PANC-1/SSTR2si cells. Control PANC-1 NS cells have signatures comparable to PANC-1 cells. 10 nM dermorphin and 10 nM L-054,264 were used. Measurements were obtained from three independent experiments, each done in duplicate. Results are expressed as the average with standard deviation. FIG. 17B. Combined MOR and CXCR4 agonist treatment and CXCR4 agonist treatment did not have a significant effect on mRNA levels of 4 markers in PANC-1 cells. 10 nM dermorphin and 100 ng/mL CXCL12 were used. Measurements were obtained from three independent experiments, each done in duplicate. Results are expressed as the average with standard deviation. FIG. 17C. Combined MOR and SSTR2 agonist treatment increased protein levels of vimentin and N-cadherin and decreased levels of E-cadherin in PANC-1 cells but not in normal pancreatic cells. Large regions of representative original images are provided in FIG. 18H.

FIG. 18A. Quantification of GPCR protein levels from 3 independent measurements with standard deviation. The blots were quantified using the Biorad-ImageLab software. FIG. 18B. from FIG. 1B. FIG. 18C. from FIG. 7. FIG. 18D. Quantification of co-IP blots with standard deviation from FIG. 3D. The blots were quantified using the Biorad-ImageLab software. FIG. 18E. From FIG. 5A. FIG. 18F. from FIG. 5D. FIG. 18G. from FIG. 16F. FIG. 18H. from FIG. 17C.

FIG. 19A shows that treatment with combination of MOR and SSTR2 agonists appears to lead to increased number of live PANC-1 cells. Low serum and full media were controls. Each condition was repeated minimum twice in triplicates. FIG. 19B shows that treatment with combination of MOR and SSTR2 antagonist (methylnaltrexone (MNTX) and Bim-23627) appears to lead to reduced growth of PANC-1 derived MCTS. Minimum of 7 MCTS per condition.

DETAILED DESCRIPTION

Definitions

Figure 1A:
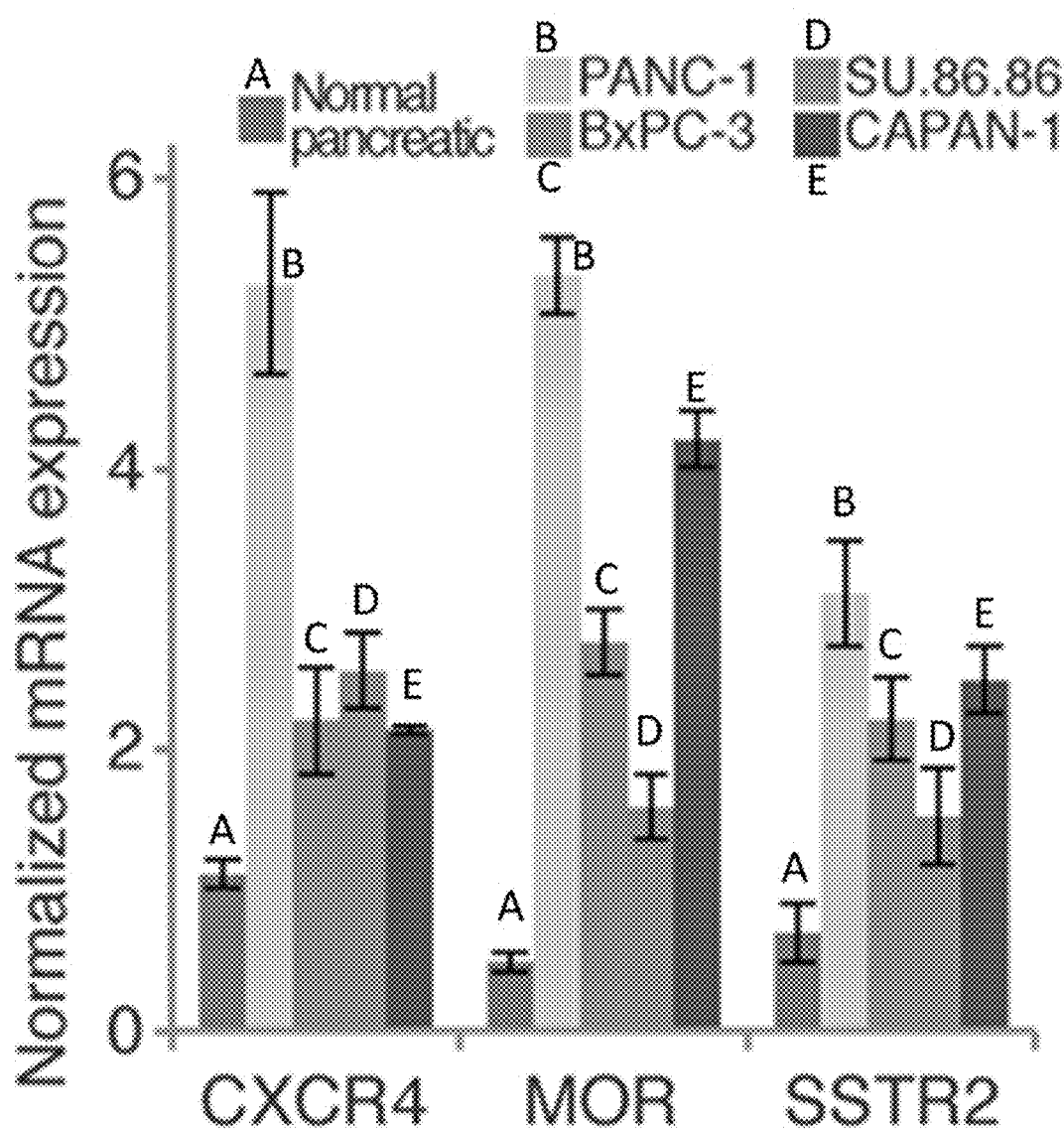
FIG. 1A-1B: Expression of CXCR4, MOR, and SSTR2 in pancreatic cell lines.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

A "chemical linker," as provided herein, is a covalent linker, a non-covalent linker, a peptide linker (a linker including a peptide moiety), a cleavable peptide linker, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof. Thus, a chemical linker as provided herein may include a plurality of chemical moieties, wherein each of the plurality of chemical moieties is chemically different. Alternatively, the chemical linker may be a non-covalent linker. Examples of non-covalent linkers include without limitation, ionic bonds, hydrogen bonds, halogen bonds, van der Waals interactions (e.g. dipole-dipole, dipole-induced dipole, London dispersion), ring stacking (pi effects), and hydrophobic interactions. In embodiments, a chemical linker is formed using conjugate chemistry including, but not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition).

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer. A "fusion protein" refers to a chimeric protein encoding two or more separate protein sequences that is recombinantly expressed as a single moiety.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids sequences encode any given amino acid residue. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers nucleic acids that have the same basic chemical structure as a naturally occurring nucleic acids. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

As used herein, the term "conjugate" refers to the association between atoms or molecules. The association can be direct or indirect. For example, a conjugate between polypeptides provided herein (e.g., a MOR polypeptide and a SSTR2 polypeptide) can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, the polypeptides provided herein (e.g., a MOR polypeptide and a SSTR2 polypeptide) are non-covalently bound through a non-covalent chemical reaction between a component of the first polypeptide (e.g., a MOR polypeptide) and a component of the second polypeptide (e.g., SSRT2 polypeptide). In embodiments, the polypeptides provided herein (e.g., a MOR polypeptide and a SSTR2 polypeptide) are non-covalently bound through an accessory protein (i.e. a polypeptide linker). An "accessory protein" as referred to herein is a polypeptide linking a MOR polypeptide provided herein to a SSTR2 polypeptide provided herein. The accessory protein may non-covalently bind to a MOR polypeptide provided herein. In embodiments, the accessory protein binds non-covalently to a SSTR2 polypeptide. Examples of accessory proteins linking a MOR polypeptide to a SSTR2 polypeptide are described in Gomes et al., 2004, Pello et al., 2008, Finley et al., 2008, and Kharmate et al., 2013, which are hereby incorporated in their entirety and for all purposes. In other embodiments, the polypeptides provided herein (e.g., a MOR polypeptide and a SSTR2 polypeptide) include one or more reactive moieties, e.g., a covalent reactive moiety, as described herein (e.g., an amine reactive moiety). In other embodiments, the microparticle includes a linker e.g., a polypeptide linker or peptide linker) with one or more reactive moieties, e.g., a covalent reactive moiety, as described herein (e.g., an amine reactive moiety).

Useful reactive moieties or functional groups used for conjugate chemistries (including "click chemistries" as known in the art) herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc.;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds; and (n) sulfones, for example, vinyl sulfone.

The reactive functional groups can be chosen such that they do not participate in, or interfere with, the chemical stability of the compositions described herein. Alternatively, a reactive functional group can be protected from participating in the crosslinking reaction by the presence of a protecting group.

Chemical synthesis of compositions by joining small modular units using conjugate ("click") chemistry is well known in the art and described, for example, in H. C. Kolb, M. G. Finn and K. B. Sharpless ((2001). "Click Chemistry: Diverse Chemical Function from a Few Good Reactions". Angewandte Chemie International Edition 40 (11): 2004-2021); R. A. Evans ((2007). "The Rise of Azide-Alkyne 1,3-Dipolar 'Click' Cycloaddition and its Application to Polymer Science and Surface Modification". Australian Journal of Chemistry 60 (6): 384-395; W. C. Guida et al. Med. Res. Rev. p 3 1996; Spiteri, Christian and Moses, John E. ((2010). "Copper-Catalyzed Azide-Alkyne Cycloaddition: Regioselective Synthesis of 1,4,5-Trisubstituted 1,2,3-Triazoles". Angewandte Chemie International Edition 49 (1): 31-33); Hoyle, Charles E. and Bowman, Christopher N. ((2010). "Thiol-Ene Click Chemistry". Angewandte Chemie International Edition 49 (9): 1540-1573); Blackman, Melissa L. and Royzen, Maksim and Fox, Joseph M. ((2008). "Tetrazine Ligation: Fast Bioconjugation Based on Inverse-Electron-Demand Diels-Alder Reactivity". Journal of the American Chemical Society 130 (41): 13518-13519); Devaraj, Neal K. and Weissleder, Ralph and Hilderbrand, Scott A. ((2008). "Tetrazine Based Cycloadditions: Application to Pretargeted Live Cell Labeling". Bioconjugate Chemistry 19 (12): 2297-2299); Stöckmann, Henning; Neves, Andre; Stairs, Shaun; Brindle, Kevin; Leeper, Finian ((2011). "Exploring isonitrile-based click chemistry for ligation with biomolecules". Organic & Biomolecular Chemistry), all of which are hereby incorporated by reference in their entirety and for all purposes.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, *Bioconjugate Techniques* 1996, Academic Press, Inc., San Diego.

A "labeled protein or polypeptide" is one that is bound, either covalently, through a linker or a chemical bond, or noncovalently, through ionic, van der Waals, electrostatic, or hydrogen bonds to a label such that the presence of the labeled protein or polypeptide may be detected by detecting the presence of the label bound to the labeled protein or polypeptide. Alternatively, methods using high affinity interactions may achieve the same results where one of a pair of binding partners binds to the other, e.g., biotin, streptavidin.

"Antibody" refers to a polypeptide comprising a framework region from an immunoglobulin gene or fragments thereof that specifically binds and recognizes an antigen, e.g., a specific bacterial antigen. Typically, the "variable region" contains the antigen-binding region of the antibody (or its functional equivalent) and is most critical in specificity and affinity of binding. See Paul, *Fundamental Immunology* (2003).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies can exist as intact immunoglobulins or as any of a number of well-characterized fragments that include specific antigen-binding activity. Such fragments can be produced by digestion with various peptidases. Pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell.

The term "modulation", "modulate", or "modulator" are used in accordance with their plain ordinary meaning and refer to the act of changing or varying one or more properties. "Modulator" refers to a composition that increases or decreases the level of a target molecule or the function of a target molecule or the physical state of the target of the molecule. "Modulation" refers to the process of changing or varying one or more properties. For example, as applied to the effects of a modulator on a biological target, to modulate means to change by increasing or decreasing a property or function of the biological target or the amount of the biological target.

A "binding agent" as provided herein refers to a substance capable of binding a SSTR2-MOR polypeptide complex. The binding agent may be a nucleic acid or a protein. In embodiments, the binding agent is an aptamer. In embodiments, the binding agent is a peptide. In embodiments, the binding agent is a small molecule. In embodiments, the binding agent is an antibody. In embodiments, the SSTR2-MOR polypeptide complex of a fragment thereof is contacted with a binding agent in a biological sample (e.g., whole blood, serum or plasma). In embodiments, the binding agent includes a detectable moiety. In embodiments, the detectable moiety is a fluorescent moiety. In embodiments, the binding agent includes a capturing moiety. A "capturing moiety" refers to a protein or nucleic acid, which is covalently, through a linker or a chemical bond, or noncovalently attached to the binding agent and is capable of interacting with a capturing agent. An example of a capturing moiety useful for the methods provided herein is biotin.

A "capturing agent" as provided herein refers to an agent capable of binding a capturing moiety. The interaction between the capturing moiety and the capturing agent may be a high affinity interaction, wherein the capturing moiety and the capturing agent bind to each other (e.g., biotin, streptavidin). An example of a capturing agent useful for the methods provided herein are streptavidin coated beads. In embodiments, the capturing agent is a streptavidin coated bead. Without limitation any suitable affinity binding pairs known in the art may be used as capturing moiety and capturing agent in the methods provided herein. For example, the capturing moiety may be an antibody and the capturing agent may be an antigen-coated bead. In embodiments, the capturing moiety is biotin and the capturing agent is a streptavidin coated bead.

As defined herein, the term "inhibition", "inhibit", "inhibiting" and the like in reference to a protein-inhibitor (e.g. antagonist) interaction means negatively affecting (e.g. decreasing) the activity or function of the protein relative to the activity or function of the protein in the absence of the inhibitor. In embodiments inhibition refers to reduction of a disease or symptoms of disease. Thus, in embodiments, inhibition includes, at least in part, partially or totally blocking stimulation, decreasing, preventing, or delaying activation, or inactivating, desensitizing, or down-regulating signal transduction or enzymatic activity or the amount of a protein.

The term "antagonist" as provided herein refers to a substance (e.g., small molecule, peptide) capable of detectably lowering expression or activity of a given protein (e.g., a MOR polypeptide or a SSTR2 polypeptide) relative to the absence of the antagonist. The antagonist can inhibit expression or activity by 10%, 20%, 30%, 40%, 50%, 60%, 70%, 80%, 90%, 100% or less in comparison to a control in the absence of the antagonist. In embodiments, the inhibition is 1.5-fold, 2-fold, 3-fold, 4-fold, 5-fold, 10-fold, or more than the expression or activity in the absence of the antagonist.

A "MOR antagonist" is a compound or small molecule that inhibits a MOR protein e.g., by binding, partially or totally blocking stimulation, decrease, prevent, or delay activation, or inactivate, desensitize, or down-regulate signal transduction, gene expression or enzymatic activity necessary for MOR activity. Alternatively, a MOR antagonist may decrease the activity of a protein or receptor in a signaling pathway that is involved in the activation of MOR or increase the activity of a protein or receptor in a signaling pathway that is involved in inhibiting/reducing MOR activity.

A "SSTR2 antagonist" is a compound or small molecule that inhibits a SSTR protein e.g., by binding, partially or totally blocking stimulation, decrease, prevent, or delay activation, or inactivate, desensitize, or down-regulate signal transduction, gene expression or enzymatic activity necessary for SSTR2 activity. Alternatively, a SSTR2 antagonist may decrease the activity of a protein or receptor in a signaling pathway that is involved in the activation of SSTR2 or increase the activity of a protein or receptor in a signaling pathway that is involved in inhibiting/reducing SSTR2 activity. Non-limiting examples of SSTR2 antagonists useful for the compositions and methods provided herein include antagonists described in Bass, R. T. et al. Molecular Pharmacology, 50:709-715(1996); Bass, R. T. et al. Molecular Pharmacology, 50:709-715(1996); Fani, M. et al., J Nucl Med 2011; 52:1110-1118; Rossowski, W. J. et al. European Journal of Pharmacology 438 (2002) 159-170; Hocart, S. J. et al. Journal of Medicinal Chemistry (1999), 42(11), 1863-1871; Yue, J. T. et al. Diabetes. 2012 January; 61(1):197-207; Baumbach, W. R. Mol Pharmacol. 1998 November; 54(5):864-73; Rossowski, W. J. et al. European Journal of Pharmacology 438 (2002) 159-170; Tulipano, G. et al. Endocrinology 143(4):1218-1224; Hocart, S. J. J. Med. Chem. 1998, 41, 1146-1154; Edwards, W. B. et al. Bioconjugate Chem. 2008, 19, 192-200; Booth, C. E. GASTROENTEROLOGY 2001; 121: 358-369; Nunn, C. Naunyn Schmiedebergs Arch Pharmacol. 2003 January; 367(1):1-9; Tran, T. et al. J Med Chem. 1998 Jul. 16; 41(15):2679-85; Hay, B. A. et al. Bioorg Med Chem Lett. 2001 Oct. 22; 11(20):2731-4; Rajeswaran W. G. et al. Bioorg Med Chem. 2002 June; 10(6):2023-9; Grace, C. R. Biopolymers. 2008 December; 89(12):1077-87; Li, Yawen; Gallazzi, Fabio; Kuchuk, Maryna; Lewis, Michael R.; Jurisson, Silvia S.; Hennkens, Heather M. from Abstracts of Papers, 250th ACS National Meeting & Exposition, Boston, Mass., United States, Aug. 16-20, 2015 (2015), FLUO-13; U.S. Pat. No. 8,206,722 B2; European Patent Application EP 1086947; US Published Patent Application US 20020091125 A1; Published International Application WO 2001081408 A2; Published International Application WO 2006052723; U.S. Pat. No. 5,846,934; Published International Application WO 2009129311; US Published Patent Application US20080299040; Published International Application WO 2008048942; Published International Application WO 2003090677; US Published Patent Application US 20020016298; US Published Patent Application US 20090004195; U.S. Pat. No. 5,925,618; European Patent Application EP 863156 A1; European Patent Application EP 1149842 A2; which are hereby incorporated in their entirety and for all purposes.

The term "MOR" or "MOR polypeptide" as provided herein includes any of the recombinant or naturally-occurring forms of the μ-opioid receptors (MOR) or variants or homologs thereof that maintain MOR polypeptide (e.g. within at least 50%, 80%, 90%, 95%, 96%, 97%, 98%, 99% or 100% activity compared to MOR). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring MOR polypeptide. In embodiments, the MOR polypeptide is the protein as identified by the UniProt reference P35372, homolog or functional fragment thereof. In embodiments, the MOR polypeptide is encoded by a nucleic acid sequence identified by the NCBI sequence reference GI:550822366, homolog or functional fragment thereof.

The term "SSTR2" or "SSTR2 polypeptide" as provided herein includes any of the recombinant or naturally-occurring forms of the Somatostatin receptor type 2 (SSTR2) or variants or homologs thereof that maintain SSTR2 polypeptide (e.g. within at least 50%, 80%, 90%, 95%, 96%, 97%, 98%, 99% or 100% activity compared to SSTR2). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring SSTR2 polypeptide. In embodiments, the SSTR2 polypeptide is the protein as identified by the UniProt reference P30874, homolog or functional fragment thereof. In embodiments, the SSTR2 polypeptide is encoded by a nucleic acid sequence identified by the NCBI sequence reference GI:44890054, homolog or functional fragment thereof.

"BNTX" in a customary sense refers to the compound having the chemical name: Morphinan-6-one,17-(cyclopropylmethyl)-4,5-epoxy-3,14-dihydroxy-7-(phenylmethylene)-,(5a,7E)-maleate. "AT-076" in a customary sense refers to the compound identified by PubChem reference number 91938095. "CTAP" in a customary sense refers to a peptide having the chemical name D-Phe-Cys-Tyr-D-Trp-Arg-Thr-Pen-Thr-NH$_2$. "LY2456302" in a customary sense refers to the compound identified by Cas Registry No.: 1174130-61-0 or the chemical name 4-[4-[[(2S)-2-(3,5-dimethylphenyl)pyrrolidin-1-yl]methyl]phenoxy]-3-fluorobenzamide or zyklophin.

As used herein, "treating" or "treatment of" a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently.

As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

The term "prevent" refers to a decrease in the occurrence of pancreatic disease symptoms in a patient. As indicated above, the prevention may be complete (no detectable symptoms) or partial, such that fewer symptoms are observed than would likely occur absent treatment.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a MOR antagonist as described herein and a MOR polypeptide. In embodiments contacting includes, for example, allowing a MOR antagonist described herein to interact with a MOR polypeptide. In embodiments contacting includes, for example, allowing a MOR polypeptide described herein to interact with a SSTR2 polypeptide.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The compound of the invention (MOR antagonist, SSTR2 antagonist) can be administered alone or can be coadministered to the patient. Coadministration is meant to include simultaneous or sequential administration of the compound individually or in combination (more than one compound or agent). Co-administration as used herein also refers to administration of ADCs as described herein. Thus, in embodiments, the preparations can also be combined, when desired, with other active substances (e.g. to reduce metabolic degradation). The compositions of the present invention can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

A "effective amount" is an amount sufficient for an active compound (e.g., a MOR antagonist or a SSTR2 antagonist) to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount. "A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations.

Pharmaceutical compositions provided by the present invention include compositions wherein the active ingredient (e.g. compositions described herein, including embodiments or examples) is contained in a therapeutically effective amount, i.e., in an amount effective to achieve its intended purpose. The actual amount effective for a particular application will depend, inter alia, on the condition being treated. For any antagonist described herein, the therapeutically effective amount can be initially determined from cell culture assays. Determination of a therapeutically effective amount of a compound (e.g., SSTR2 antagonist or MOR antagonist) of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer, neurodegeneration, or cardiovascular disease and severity of such symptoms), kind of concurrent treatment, complications from the disease being treated or other health-related problems. Other therapeutic regimens or agents can be used in conjunction with the methods and compounds of the invention. Adjustment and manipulation of established dosages (e.g., frequency and duration) are well within the ability of those skilled in the art.

For any compound described herein (e.g., a MOR antagonist or a SSTR2 antagonist), the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The term "anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer. In embodiments, the anticancer agent is a SSTR2 antagonist. In embodiments, the anticancer agent is a MOR antagonist.

The compounds described herein (e.g., a MOR antagonist or a SSTR2 antagonist) can be used in combination with one another, with other active agents known to be useful in treating a cancer such as anti-cancer agents.

Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexa- methlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like. In embodiments, the compositions herein may be used in combination with adjunctive agents that may not be effective alone, but may contribute to the efficacy of the active agent in treating cancer.

In embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In embodiments, co-administration can be accomplished by co-formulation, i.e., preparing a single pharmaceutical composition including both active agents. In embodiments, the active agents can be formulated separately. In embodiments, the active and/or adjunctive agents may be linked or conjugated to one another.

The term "associated" or "associated with" in the context of a substance or substance activity or function associated with a disease (e.g. a protein associated disease, or symptom associated with a cancer, neurodegenerative disease, or cardiovascular disease) means that the disease (e.g. cancer) is caused or characterized by (in whole or in part) the substance or substance activity or function, or a symptom of the disease is caused or characterized by (in whole or in part) the substance or substance activity or function. As used herein, what is described as being associated with a disease, if a causative agent, could be a target for treatment of the disease. For example, a disease associated with aberrant MOR or SSTR2 expression or function, may be treated with an agent (e.g. composition as described herein) effective for decreasing the level of activity of MOR or SSTR2, respectively.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active or prodrug form of a composition as provided herein with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "cancer" refers to all types of cancer, neoplasm, benign or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulinoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The P388 leukemia model is widely accepted as being predictive of in vivo anti-leukemic activity. It is believed that a compound that tests positive in the P388 assay will generally exhibit some level of anti-leukemic activity in vivo regardless of the type of leukemia being treated. Accordingly, the present application includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma *villosum*.

As used herein, the terms "metastasis," "metastatic," and "metastatic cancer" can be used interchangeably and refer to the spread of a proliferative disease or disorder, e.g., cancer, from one organ to another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans).

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

GPCR Ligand Conjugate

Provided herein are, inter alia, compositions and methods for the treatment of cancer (e.g., pancreatic cancer) and inhibition of metastasis (e.g., pancreatic cancer-related metastasis). The compositions and methods provided herein are, inter alia, useful to treat pancreatic cancer. Applicants are the first to describe the expression of a heteromer formed by μ-opioid receptor (MOR) and somatostatin receptor 2 (SSTR2) on pancreatic cancer cells. A "heteromer" as referred to herein is used according to its ordinary meaning in the art and refers to a multi-protein complex (a protein complex consisting of more than one polypeptide) which includes a MOR polypeptide and a SSTR2 polypeptide. The term heteromer may be used interchangeably with the term "SSTR2-MOR polypeptide complex." In embodiments, a heteromer includes MOR polypeptide and a SSTR2 polypeptide. A heteromer may further include additional polypeptides (e.g., accessory proteins), which may interact with the MOR and/or SSTR2 polypeptide. Applicants have found that heteromers including MOR and SSTR2, while present on pancreatic cancer cells, are absent on healthy cells and therefore constitute a unique target for therapeutic purposes. The heteromer is formed by a MOR polypeptide and a SSTR2 polypeptide bound together covalently (through a chemical linker) or non-covalently (through accessory proteins). Applicants have surprisingly found that binding of a MOR agonist and a SSTR2 agonist to its corresponding receptor in a MOR/SSTR2 heteromer expressed on a pancreatic cancer cell increases the metastatic potential of said pancreatic cancer cell. Applicants will test the effect of MOR antagonists and SSTR2 antagonists on cancer activity and metastatic potential in pancreatic cancer cells and other cancer cells (e.g., breast cancer cells).

In a first aspect, there is provided a G protein-coupled receptor (GPCR)-ligand conjugate including: (i) a Mu opioid receptor (MOR) polypeptide bound to a somatostatin receptor 2 (SSTR2) polypeptide; and (ii) a first antagonist bound to a MOR polypeptide or a SSTR2 polypeptide. In embodiments, the MOR polypeptide includes the sequence of SEQ ID NO:1. In embodiments the MOR polypeptide is the sequence of SEQ ID NO:1. In embodiments the SSTR2 polypeptide includes the sequence of SEQ ID NO:2. In embodiments the SSTR2 polypeptide is the sequence of SEQ ID NO:2.

The first antagonist may be a MOR antagonist or a SSTR2 antagonist. Where the first antagonist is a MOR antagonist it may be bound to the MOR polypeptide covalently or non-covalently. In embodiments, the MOR antagonist is bound to the MOR polypeptide through a chemical linker. In embodiments, the chemical linker is a covalent linker, a non-covalent linker, a peptide linker (a linker including a peptide moiety), a cleavable peptide linker, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof. Thus, a chemical linker as provided herein may include a plurality of chemical moieties, wherein each of the plurality of moieties is chemically different.

In embodiments, the MOR antagonist is a small molecule or a peptide. In embodiments, the MOR antagonist is a peptide. In embodiments, the MOR antagonist is a small molecule. In embodiments, the MOR antagonist is [$^3$H]diprenorphine, [$^3$H]naloxone, naloxonazine, diprenorphine, quadazocine, naltrexone, nalmefene, alvimopan, levallorphan, naloxone, nalorphine, BNTX, AT-076, methylnaltrexone, CTAP, naloxone benzoylhydrazone, naltrindole, naltriben, nor-binaltorphimine, LY2456302 or zyklophin. In embodiments, the MOR antagonist is [$^3$H]diprenorphine. In embodiments, the MOR antagonist is [$^3$H]naloxone. In embodiments, the MOR antagonist is naloxonazine. In embodiments, the MOR antagonist is diprenorphine. In embodiments, the MOR antagonist is quadazocine. In embodiments, the MOR antagonist is naltrexone. In embodiments, the MOR antagonist is nalmefene. In embodiments, the MOR antagonist is alvimopan. In embodiments, the MOR antagonist is levallorphan. In embodiments, the MOR antagonist is naloxone. In embodiments, the MOR antagonist is nalorphine. In embodiments, the MOR antagonist is BNTX. The term "BNTX" is used in its customary sense and refers to the compound identified by CAS reference number 864461-31-4. In embodiments, the MOR antagonist is AT-076. The term "AT-076" is used in its customary sense and refers to the compound identified by PubChem reference number CID 91938095. In embodiments, the MOR antagonist is methylnaltrexone. In embodiments, the MOR antagonist is CTAP. In embodiments, the MOR antagonist is naloxone benzoylhydrazone. In embodiments, the MOR antagonist is naltrindole. In embodiments, the MOR antagonist is naltriben. In embodiments, the MOR antagonist is nor-binaltorphimine. In embodiments, the MOR antagonist is LY2456302. The term "LY2456302" is used in its customary sense and refers to the compound identified by CAS reference number 1174130-61-0. In embodiments, the MOR antagonist is zyklophin.

The first antagonist may be a SSTR2 antagonist. Where the first antagonist is a SSTR2 antagonist it may be bound to the SSTR2 polypeptide covalently or non-covalently. In embodiments, the SSTR2 antagonist is bound to the SSTR2 polypeptide through a chemical linker. In embodiments, the chemical linker is a covalent linker, a non-covalent linker, a peptide linker (a linker including a peptide moiety), a cleavable peptide linker, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof. Thus, a chemical linker as provided herein may include a plurality of chemical moieties, wherein each of the plurality of moieties is chemically different. In embodiments, the first antagonist is a SSTR2 antagonist. In embodiments, the SSTR2 antagonist is a small molecule or a peptide. In embodiments, the SSTR2 antagonist is a small molecule.

In embodiments, the SSTR2 antagonist is a peptide. In embodiments, the SSTR2 antagonist is a peptide of formula (cyclo 3-14)DOTA-pNO$_2$-Phe-cyclo[DCys-Tyr-D-4Aph (Cbm)-Lys-Thr-Cys]-DTyr-NH$_2$, NH$_2$-pNO$_2$-Phe-cyclo [DCys-Tyr-D-4Aph(Cbm)-Lys-Thr-Cys]-DTyr-NH$_2$, H-p-Chloro-DPhe-cyclo[DCys-Pal-Trp-Lys-Val-Cys]-2-Nal-NH$_2$ or H-p-Chloro-Phe-DCys-β-(2-pyridyl)-Ala-Trp-Lys-Val-Cys-2-Nal-NH$_2$. In embodiments, the SSTR2 antagonist is a peptide of formula (cyclo 3-14)DOTA-pNO$_2$-Phe-cyclo [DCys-Tyr-D-4Aph(Cbm)-Lys-Thr-Cys]-DTyr-NH$_2$ or NH$_2$-pNO$_2$-Phe-cyclo[DCys-Tyr-D-4Aph(Cbm)-Lys-Thr-Cys]-DTyr-NH$_2$. In embodiments, the SSTR2 antagonist is a peptide of formula (cyclo 3-14)DOTA-pNO$_2$-Phe-cyclo [DCys-Tyr-D-4Aph(Cbm)-Lys-Thr-Cys]-DTyr-NH$_2$. In embodiments, the SSTR2 antagonist is a peptide of formula NH$_2$-pNO$_2$-Phe-cyclo[DCys-Tyr-D-4Aph(Cbm)-Lys-Thr-Cys]-DTyr-NH$_2$. In embodiments, the SSTR2 antagonist is a peptide of formula H-p-Chloro-DPhe-cyclo[DCys-Pal-Trp-Lys-Val-Cys]-2-Nal-NH$_2$. In embodiments, the SSTR2 antagonist is a peptide of formula Hp-Chloro-Phe-DCys-β-(2-pyridyl)-Ala-Trp-Lys-Val-Cys-2-Nal-NH$_2$. In embodiments, the SSTR2 antagonist is a peptide of formula H-p-Chloro-Phe-D-Cys-β-(2-pyridyl)-Ala-Trp-Lys-Val-Cys-2-Nal-NH$_2$. Where the SSTR2 antagonist is a peptide of formula H-p-Chloro-Phe-D-Cys-β-(2-pyridyl)-Ala-Trp-Lys-Val-Cys-2-Nal-NH$_2$ it may also referred to as BIM-23627. "BIM-23627" as used herein refers in a customary sense to the compound identified by Cas Registry No: 429619-37-4.

In embodiments, a second antagonist is bound to the MOR polypeptide or the SSTR2 polypeptide. In embodiments, the first antagonist is a SSTR2 antagonist and the second antagonist is a MOR antagonist and the SSTR2 antagonist and the MOR antagonist are defined as described herein. For example, the MOR antagonist may be a small molecule (e.g., [$^3$H]diprenorphine, [$^3$H]naloxone, naloxonazine, diprenorphine, quadazocine, naltrexone, nalmefene, alvimopan, levallorphan, naloxone, nalorphine, BNTX, AT-076, methylnaltrexone, CTAP, naloxone benzoylhydrazone, naltrindole, naltriben, nor-binaltorphimine, LY2456302).

In embodiments, the first antagonist is a MOR antagonist and the second antagonist is a SSTR2 antagonist. The SSTR2 antagonist is defined as described herein (e.g., a small molecule or a peptide). The SSTR2 antagonist may be a peptide of formula (cyclo 3-14)DOTA-pNO$_2$-Phe-cyclo [DCys-Tyr-D-4Aph(Cbm)-Lys-Thr-Cys]-DTyr-NH$_2$ or NH$_2$-pNO$_2$-Phe-cyclo[DCys-Tyr-D-4Aph(Cbm)-Lys-Thr-Cys]-DTyr-NH$_2$.

As described above the MOR polypeptide and the SSTR2 polypeptide form a heteromer and are bound together through a covalent or non-covalent linker. In embodiments, the chemical linker is a covalent linker, a non-covalent linker (e.g., an accessory protein), a peptide linker (a linker including a peptide moiety), a cleavable peptide linker, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof. Thus, a chemical linker as provided herein may include a plurality of chemical moieties, wherein each of the plurality of moieties is chemically different. In embodiments, the MOR polypeptide is covalently bound to the SSTR2 polypeptide. In embodiments, the MOR polypeptide is non-covalently bound to the SSTR2 polypeptide.

The conjugates provided herein including embodiments thereof may form part of a cell (e.g., a cancer cell). Thus, in embodiments, the conjugate forms part of a cell. In embodiments, the cell is a cancer cell. As described above the cancer cell may be a pancreatic cancer cell. Thus, in embodiments, the cell is a pancreatic cancer cell. In embodiments, the cell is a pancreatic ductal adenocarcinoma cell.

The conjugates provided herein including embodiments thereof may form part of specific cellular components. In embodiments, the conjugate forms part of a cell membrane. In embodiments, the conjugate forms part of a lipid raft. In embodiments, the conjugate forms part of a cytoplasm.

The MOR/SSTR2 conjugates provided herein including embodiments thereof may include a MOR antagonist bound to a MOR polypeptide and a SSTR2 antagonist bound to a SSTR2 polypeptide. Thus, in one aspect, there is provided a G-protein-coupled receptor (GPCR)-ligand conjugate including: (i) a Mu opioid receptor (MOR) polypeptide bound to a MOR antagonist; and (ii) a somatostatin receptor 2 (SSTR2) polypeptide bound to a SSTR2 antagonist; wherein the MOR polypeptide and the SSTR2 polypeptide are bound together. As described herein, the MOR polypeptide may include the sequence of SEQ ID NO:1. In embodiments, the MOR polypeptide is the sequence of SEQ ID NO:1. In embodiments, the SSTR2 polypeptide includes the sequence of SEQ ID NO:2. In embodiments, the SSTR2 polypeptide is the sequence of SEQ ID NO:2.

In embodiments, the MOR antagonist is a small molecule or a peptide. In embodiments, the MOR antagonist is a peptide. In embodiments, the MOR antagonist is a small molecule. In embodiments, the MOR antagonist is [$^3$H] diprenorphine, [$^3$H]naloxone, naloxonazine, diprenorphine, quadazocine, naltrexone, nalmefene, alvimopan, levallorphan, naloxone, nalorphine, BNTX, AT-076, methylnaltrexone, CTAP, naloxone benzoylhydrazone, naltrindole, naltriben, nor-binaltorphimine, LY2456302 or zyklophin. In embodiments, the MOR antagonist is [$^3$H]diprenorphine. In embodiments, the MOR antagonist is [$^3$H]naloxone. In embodiments, the MOR antagonist is naloxonazine. In embodiments, the MOR antagonist is diprenorphine. In embodiments, the MOR antagonist is quadazocine. In embodiments, the MOR antagonist is naltrexone. In embodiments, the MOR antagonist is nalmefene. In embodiments, the MOR antagonist is alvimopan. In embodiments, the MOR antagonist is levallorphan. In embodiments, the MOR antagonist is naloxone. In embodiments, the MOR antagonist is nalorphine. In embodiments, the MOR antagonist is BNTX. The term "BNTX" is used in its customary sense and refers to the compound identified by CAS reference number 864461-31-4. In embodiments, the MOR antagonist is AT-076. The term "AT-076" is used in its customary sense and refers to the compound identified by PubChem reference number CID 91938095. In embodiments, the MOR antagonist is methylnaltrexone. In embodiments, the MOR antagonist is CTAP. In embodiments, the MOR antagonist is naloxone benzoylhydrazone. In embodiments, the MOR antagonist is naltrindole. In embodiments, the MOR antagonist is naltriben. In embodiments, the MOR antagonist is nor-binaltorphimine. In embodiments, the MOR antagonist is LY2456302. The term "LY2456302" is used in its customary sense and refers to the compound identified by CAS reference number 1174130-61-0. In embodiments, the MOR antagonist is zyklophin.

In embodiments, the SSTR2 antagonist is a small molecule or a peptide. In embodiments, the SSTR2 antagonist is a small molecule. In embodiments, the SSTR2 antagonist is a peptide. In embodiments, the SSTR2 antagonist is a peptide of formula (cyclo 3-14)DOTA-pNO$_2$-Phe-cyclo[DCys-Tyr-D-4Aph(Cbm)-Lys-Thr-Cys]-DTyr-NH$_2$, NH$_2$-pNO$_2$-Phe-cyclo[DCys-Tyr-D-4Aph(Cbm)-Lys-Thr-Cys]-DTyr-NH$_2$, H-p-Chloro-DPhe-cyclo[DCys-Pal-Trp-Lys-Val-Cys]-2-Nal-NH$_2$ or H-p-Chloro-Phe-DCys-β-(2-pyridyl)-Ala-Trp-Lys-Val-Cys-2-Nal-NH$_2$. In embodiments, the SSTR2 antagonist is a peptide of formula (cyclo 3-14) DOTA-pNO$_2$-Phe-cyclo[DCys-Tyr-D-4Aph(Cbm)-Lys-Thr-Cys]-DTyr-NH$_2$ or NH$_2$-pNO$_2$-Phe-cyclo[DCys-Tyr-D-4Aph(Cbm)-Lys-Thr-Cys]-DTyr-NH$_2$. In embodiments, the SSTR2 antagonist is a peptide of formula (cyclo 3-14) DOTA-pNO$_2$-Phe-cyclo[DCys-Tyr-D-4Aph(Cbm)-Lys-Thr-Cys]-DTyr-NH$_2$. In embodiments, the SSTR2 antagonist is a peptide of formula NH$_2$-pNO$_2$-Phe-cyclo[DCys-Tyr-D-4Aph(Cbm)-Lys-Thr-Cys]-DTyr-NH$_2$. In embodiments, the SSTR2 antagonist is a peptide of formula H-p-Chloro-DPhe-cyclo[DCys-Pal-Trp-Lys-Val-Cys]-2-Nal-NH$_2$. In embodiments, the SSTR2 antagonist is a peptide of formula H-p-Chloro-Phe-DCys-β-(2-pyridyl)-Ala-Trp-Lys-Val-Cys-2-Nal-NH$_2$.

In embodiments, the conjugate forms part of a cell. In embodiments, the conjugate forms part of a cell membrane. In embodiments, the conjugate forms part of a lipid raft. In embodiments, the conjugate forms part of a cytoplasm. In embodiments, the cell is a cancer cell. In embodiments, the cell is a pancreatic cancer cell. In embodiments, the cell is a pancreatic ductal adenocarcinoma cell.

In embodiments, the MOR polypeptide is the sequence of SEQ ID NO:1, the MOR antagonist is methylnatrexone, the SSTR2 polypeptide is the sequence of SEQ ID NO:2 and the SSTR2 antagonist is a peptide of formula (cyclo 3-14) DOTA-pNO$_2$-Phe-cyclo[DCys-Tyr-D-4Aph(Cbm)-Lys-Thr-Cys]-DTyr-NH$_2$.

In embodiments, the MOR polypeptide is the sequence of SEQ ID NO:1, the MOR antagonist is methylnatrexone, the SSTR2 polypeptide is the sequence of SEQ ID NO:2 and the SSTR2 antagonist is a peptide of NH$_2$-pNO$_2$-Phe-cyclo[DCys-Tyr-D-4Aph(Cbm)-Lys-Thr-Cys]-DTyr-NH$_2$.

In embodiments, the MOR polypeptide is the sequence of SEQ ID NO:1, the MOR antagonist is methylnatrexone, the SSTR2 polypeptide is the sequence of SEQ ID NO:2 and the SSTR2 antagonist is a peptide of H-p-Chloro-DPhe-cyclo[DCys-Pal-Trp-Lys-Val-Cys]-2-Nal-NH$_2$.

In embodiments, the MOR polypeptide is the sequence of SEQ ID NO:1, the MOR antagonist is methylnatrexone, the SSTR2 polypeptide is the sequence of SEQ ID NO:2 and the SSTR2 antagonist is a peptide of H-p-Chloro-Phe-DCys-β-(2-pyridyl)-Ala-Trp-Lys-Val-Cys-2-Nal-NH$_2$.

Methods of Treatment

The methods described herein use the polypeptides and antagonists described herein. Thus, it is understood that the MOR antagonists and SSTR2 antagonists useful for the methods of treatment and inhibition of metastasis described in this section include any of the MOR antagonists (e.g., methylnaltrexone) and SSTR antagonists (e.g., a peptide of formula (cyclo 3-14)DOTA-pNO$_2$-Phe-cyclo[DCys-Tyr-D-4Aph(Cbm)-Lys-Thr-Cys]-DTyr-NH$_2$, NH$_2$-pNO$_2$-Phe-cyclo[DCys-Tyr-D-4Aph(Cbm)-Lys-Thr-Cys]-DTyr-NH$_2$, H-p-Chloro-DPhe-cyclo[DCys-Pal-Trp-Lys-Val-Cys]-2-Nal-NH$_2$, H-p-Chloro-Phe-DCys-β-(2-pyridyl)-Ala-Trp-Lys-Val-Cys-2-Nal-NH$_2$) described herein including embodiments thereof.

The methods provided herein are, inter alia, useful for the treatment of pancreatic cancer and/or metastasis. Applicants have surprisingly shown that SSTR2-MOR polypeptide complexes (heteromers) are selectively expressed by pancreatic cancer cells, while absent on healthy (non-cancerous) cells. Further, Applicants were the first to show that the combination treatment of a SSTR2 antagonist with a MOR antagonist inhibits pancreatic cancer cell growth and metastasis. Therefore, the SSTR2-MOR polypeptide complexes described herein may be used as therapeutic targets for treating pancreatic cancer as well as diagnostic means to detect pancreatic cells in patients having or being at risk of developing pancreatic cancer.

In a first aspect, a method of treating pancreatic cancer in a subject in need thereof is provided. The method includes administering to a subject a therapeutically effective amount of a SSTR2 antagonist, thereby treating pancreatic cancer in the subject.

In embodiments, the method includes administering to the subject a therapeutically effective amount of an anti-cancer agent. In embodiments, the method includes administering to the subject a therapeutically effective amount of a MOR antagonist. In embodiments, the effective amount of a SSTR2 antagonist and the effective amount of a MOR antagonist are a combined additive amount. In embodiments, the effective amount of a SSTR2 antagonist and the effective amount of a MOR antagonist are a combined synergistic amount. In embodiments, the SSTR2 antagonist and the MOR antagonist are administered sequentially or concurrently.

In embodiments, the SSTR2 antagonist and the MOR antagonist are administered in a combined synergistic amount. A "combined synergistic amount" as used herein refers to the sum of a first amount (e.g., an amount of an SSTR2 antagonist) and a second amount (e.g., an amount of a MOR antagonist) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of compounds administered in combination where the measured effect is greater than the sum of the individual effects of each of the compounds administered alone as a single agent.

In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the SSTR2 antagonist when used separately from the MOR antagonist. In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the MOR antagonist when used separately from the SSTR2 antagonist.

The synergistic effect may be an SSTR2 activity decreasing effect and/or a MOR activity decreasing effect. In embodiments, synergy between the SSTR2 antagonist and the MOR inhibitor may result in about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater decrease (e.g., decrease of SSTR2 activity or decrease of MOR activity) than the sum of the decrease of the SSTR2 antagonist or the MOR antagonist when used individually and separately. In embodiments, synergy between the SSTR2 antagonist and the MOR antagonist may result in 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater inhibition of the SSTR2 protein and/or the MOR protein than the sum of the inhibition of the SSTR2 antagonist or the MOR antagonist when used individually and separately.

The synergistic effect may be a cancer-treating effect such as an pancreatic cancer (i.e. a pancreatic cancer-treating synergistic effect), bladder cancer (i.e. a bladder cancer-treating synergistic effect), melanoma (i.e. a melanoma-treating synergistic effect), renal cell carcinoma (i.e. a renal cell carcinoma-treating synergistic effect), colon cancer (i.e. a colon cancer-treating synergistic effect), ovarian cancer (i.e. an ovarian cancer-treating synergistic effect), gastric cancer (i.e. a gastric cancer-treating synergistic effect), breast cancer (i.e. a breast cancer-treating synergistic effect), head and neck carcinoma (i.e. a head and neck carcinoma-treating synergistic effect), prostate cancer (i.e. a prostate cancer-treating synergistic effect) and a hematologic malignancy (i.e. a hematologic malignancy-treating synergistic effect).

The SSTR2 antagonist and the MOR antagonist may be administered in combination either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of the SSTR2 antagonist and the MOR antagonist. In embodiments, where the SSTR2 antagonist and the MOR antagonist are administered sequentially, the SSTR2 antagonist is administered at a first time point and the MOR antagonist is administered at a second time point, wherein the first time point precedes the second time point. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly). Thus, in embodiments, the SSTR2 antagonist and MOR antagonist are administered simultaneously or sequentially.

In embodiments, the SSTR2 antagonist and the MOR antagonist are admixed together prior to administration. In embodiments, the SSTR2 antagonist and the MOR antagonist are administered in a single dosage form. Where the SSTR2 antagonist and the MOR antagonist are administered in a single dosage form, the SSTR2 antagonist and the MOR antagonist are included in the same dosage form (e.g., oral preparation, infusion). In embodiments, the SSTR2 antagonist and the MOR antagonist are administered in two separate dosage forms. Where the SSTR2 antagonist and the MOR antagonist are administered in two separate dosage forms, the SSTR2 antagonist and the MOR antagonist are each included in a separate dosage form (e.g., oral preparation, infusion).

In embodiments, the SSTR2 antagonist is the compound BIM-23627 and the MOR antagonist is methylnaltrexone.

In embodiments, the subject is a mammal. In embodiments, the mammal is a human.

Any of the SSTR2 antgonists or MOR antagonists described in above GPCR Ligand conjugate section may be used for the methods described herein. Thus, in embodiments, the MOR antagonist is a small molecule. In embodiments, the MOR antagonist is [$^3$H]diprenorphine, [$^3$H]naloxone, naloxonazine, diprenorphine, quadazocine, naltrexone, nalmefene, alvimopan, diprenorphine, levallorphan, nalorphine, naloxone, BNTX, AT-076, methylnaltrexone, CTAP, naloxone benzoylhydrazone, naltrindole, naltriben, nor-binaltorphimine, LY2456302 or zyklophin.

In embodiments, the MOR antagonist is methylnaltrexone (MNTX). In embodiments, the SSTR2 antagonist is a small molecule or a peptide. In embodiments, the SSTR2 antagonist is a small molecule. In embodiments, the SSTR2 antagonist is a peptide. In embodiments, the SSTR2 antagonist is a peptide of formula (cyclo 3-14)DOTA-pNO$_2$-Phe-cyclo[DCys-Tyr-D-4Aph(Cbm)-Lys-Thr-Cys]-DTyr-NH$_2$ or NH$_2$-pNO$_2$-Phe-cyclo[DCys-Tyr-D-4Aph(Cbm)-Lys-Thr-Cys]-DTyr-NH$_2$. In embodiments, the SSTR2 antagonist binds a SSTR2 polypeptide in the subject and the SSTR2 polypeptide is bound to a MOR polypeptide. In embodiments, the MOR antagonist binds a MOR polypeptide in the subject and the MOR polypeptide is bound to a SSTR2 polypeptide. Thus, a conjugate as described above may be formed.

In another aspect, a pharmaceutical composition including an SSTR2 antagonist, a MOR antagonist and a pharmaceutically acceptable excipient is provided. In embodiments, the SSTR2 antagonist and the MOR antagonist are present at a combined synergistic amount. In embodiments, the SSTR2 antagonist and the MOR antagonist are present in a single dosage form. In embodiments, the SSTR2 antagonist and the MOR antagonist are present in two dosage forms.

In another aspect, a method of inhibiting metastasis in a subject in need thereof is provided. The method includes administering to a subject a therapeutically effective amount of a SSTR2 antagonist, thereby inhibiting metastasis in the subject. In embodiments, the method includes administering to the subject a therapeutically effective amount of a MOR antagonist. In embodiments, the subject suffers from pancreatic cancer.

In one aspect, a method of detecting an expression level of a SSTR2-MOR polypeptide complex in a subject that has or is at risk for developing pancreatic cancer is provided. The method includes (i) obtaining a biological sample from the subject; and (ii) determining an expression level of an SSTR2-MOR polypeptide complex. In embodiments, the detecting includes: (a) contacting the SSTR2-MOR polypeptide complex with a binding agent in the biological sample, thereby forming a SSTR2-MOR polypeptide complex-binding agent complex; and (b) detecting the SSTR2-MOR polypeptide complex-binding agent complex. In embodiments, the method includes selecting a subject that has or is at risk for developing pancreatic cancer. In embodiments, the method includes administering to the subject an effective amount of a SSTR2 antagonist. In embodiments, the SSTR2 antagonist is a small molecule or a peptide. In embodiments, the method includes administering to the subject an effective amount of a MOR antagonist. In embodiments, the MOR antagonist is a small molecule.

In one aspect, a method of treating pancreatic cancer in a subject in need thereof is provided. The method includes (i) detecting an elevated level of an SSTR2-MOR polypeptide complex relative to a standard control; and (ii) when an elevated expression level of the SSTR2-MOR polypeptide complex is found relative to the standard control, administering to the subject an SSTR2 antagonist, thereby treating the subject. In embodiments, the method includes administering to the subject an effective amount of a MOR antagonist.

In another aspect, there is provided a method for treating pancreatic cancer in a subject in need thereof. The method includes administering to the subject a therapeutically effective amount of a MOR antagonist, thereby treating pancreatic cancer in the subject. In embodiments, the method includes administering to the subject a therapeutically effective amount of an anti-cancer agent. In embodiments, the anti-cancer agent is gemcitabine. The term "gemcitabine" is used in its customary sense and refers to the compound identified by CAS reference number 95058-81-4. In embodiments, the method includes administering to the subject a therapeutically effective amount of an SSTR2 antagonist.

In embodiments, the MOR antagonist is a small molecule. In embodiments, the MOR antagonist is [$^3$H]diprenorphine, [$^3$H]naloxone, naloxonazine, diprenorphine, quadazocine, naltrexone, nalmefene, alvimopan, levallorphan, nalorphine, naloxone, BNTX, AT-076, methylnaltrexone, CTAP, naloxone benzoylhydrazone, naltrindole, naltriben, nor-binaltorphimine, LY2456302 or zyklophin. In embodiments, the MOR antagonist is methylnaltrexone. In embodiments, the SSTR2 antagonist is a small molecule or a peptide. In embodiments, the SSTR2 antagonist is a small molecule. In embodiments, the SSTR2 antagonist is a peptide. In embodiments, the SSTR2 antagonist is a peptide of formula (cyclo 3-14)DOTA-pNO$_2$-Phe-cyclo[DCys-Tyr-D-4Aph(Cbm)-Lys-Thr-Cys]-DTyr-NH$_2$ or NH$_2$-pNO$_2$-Phe-cyclo[DCys-Tyr-D-4Aph(Cbm)-Lys-Thr-Cys]-DTyr-NH$_2$.

In embodiments, the MOR antagonist binds a MOR polypeptide in the subject and the MOR polypeptide is bound to a SSTR2 polypeptide. In embodiments, the SSTR2 antagonist binds a SSTR2 polypeptide in the subject and the SSTR2 polypeptide is bound to a MOR polypeptide.

In another aspect, there is provided a method of treating pancreatic cancer in a subject in need thereof. The method includes administering to the subject a therapeutically effective amount of a SSTR2 antagonist, thereby treating pancreatic cancer in the subject. In embodiments, the method includes administering to a subject a therapeutically effective amount of an anti-cancer agent. In embodiments, the anti-cancer agent is gemcitabine. In embodiments, the method includes administering to a subject a therapeutically effective amount of a MOR antagonist. In embodiments, the MOR antagonist is a small molecule. In embodiments, the MOR antagonist is [$^3$H]diprenorphine, [$^3$H]naloxone, naloxonazine, diprenorphine, quadazocine, naltrexone, nalmefene, alvimopan, levallorphan, nalorphine, naloxone, BNTX, AT-076, methylnaltrexone, CTAP, naloxone benzoylhydrazone, naltrindole, naltriben, nor-binaltorphimine, LY2456302 or zyklophin. In embodiments, the MOR antagonist is methylnaltrexone.

In embodiments, the SSTR2 antagonist is a small molecule or a peptide. In embodiments, the SSTR2 antagonist is a small molecule. In embodiments, the SSTR2 antagonist is a peptide. In embodiments, the said SSTR2 antagonist is a peptide of formula (cyclo 3-14)DOTA-pNO$_2$-Phe-cyclo[DCys-Tyr-D-4Aph(Cbm)-Lys-Thr-Cys]-DTyr-NH$_2$ or NH$_2$-pNO$_2$-Phe-cyclo[DCys-Tyr-D-4Aph(Cbm)-Lys-Thr-Cys]-DTyr-NH$_2$. In embodiments, the SSTR2 antagonist binds a SSTR2 polypeptide in a subject wherein the SSTR2 polypeptide is bound to a MOR polypeptide. In embodiments, the MOR antagonist binds a MOR polypeptide in a subject wherein the MOR polypeptide is bound to a SSTR2 polypeptide.

In another aspect, there is provided a method of inhibiting metastasis in a subject in need thereof. The method includes administering to the subject a therapeutically effective amount of a MOR antagonist, thereby inhibiting metastasis in the subject. In embodiments, the method includes administering to the subject a therapeutically effective amount of an SSTR2 antagonist. In embodiments, the subject suffers from pancreatic cancer.

In another aspect, there is provided a method of inhibiting metastasis in a subject in need thereof. The method includes administering to the subject a therapeutically effective amount of a SSTR2 antagonist, thereby inhibiting metastasis in the subject. In embodiments, the method includes administering to the subject a therapeutically effective amount of a MOR antagonist. In embodiments, the subject suffers from pancreatic cancer.

EXAMPLES

In the United States, the fourth leading cancer-related cause of death is pancreatic ductal adenocarcinoma—PDAC (Howlader N, 2014). For many PDAC patients, the cancer presents itself at an advanced stage and only 20% of cases are eligible for surgical resection (Li et al., 2004a). While conventional therapies (surgery, radiation, chemotherapy) have been improved (Von Hoff et al., 2013) and a new targeted therapy (Moore et al., 2007) has been introduced, the overall survival rate for PDAC patients over the last four decades remains remarkably dismal. Within five years of the diagnosis, the disease will claim approximately 93% of all patients (Howlader N, 2014). This high lethality correlates to high rates of metastasis and is partially coupled to limited treatment options (Oberstein and Olive, 2013). It is therefore imperative to identify new therapeutic targets for PDAC.

Toward this goal, Applicants have been studying G-protein coupled receptors (GPCRs), which play a substantial role in the tumorigenesis of pancreatic cancer. GPCRs activated by chemokines (e.g. from inflammation (Allavena et al., 2008)) and by neurotransmitters/hormones (from autocrine/paracrine signaling (Heasley, 2001)) can lead to pathological signaling (Hanahan and Weinberg, 2011). Additionally, GPCRs are often expressed at aberrant levels in PDAC (Koshiba et al., 2000; Balkwill, 2004; Li et al., 2004b; Billadeau et al., 2006; Laklai et al., 2009; Soria and Ben-Baruch, 2009; Call et al., 2013; Shahbaz et al., 2015), and somatic mutations in GPCRs have been found in many tumors, including pancreatic tumors (Kan et al., 2010). As such, GPCRs are being targeted in a number of clinical trials for cancer. A Phase 1 trial for pancreatic cancer (NCT02179970) is evaluating a C-X-C motif receptor 4 (CXCR4) ligand; a Phase 1 trial for pancreatic cancer (NCT01385956) is studying a combination of gemcitabine with a somatostatin receptor-2 (SSTR2) ligand; and a Phase 1 trial for advanced malignancies (NCT01015222) is examining a combination treatment involving a mu opioid receptor (MOR) ligand. Despite this significant interest, pharmacological agents that target GPCRs in PDAC are currently unavailable. The absence of such drugs may be partially attributable to the complexity of GPCR signaling networks.

Although they can organize and function as monomers (Whorton et al., 2007; Kuszak et al., 2009), an increasing body of evidence indicates that GPCRs also interact with each other, either directly or through accessory proteins (Pfeiffer et al., 2002; Gomes et al., 2004; Wang et al., 2005; Finley et al., 2008; Pello et al., 2008; Gomes et al., 2013; Kharmate et al., 2013), to form multi-component functional entities. Compared to the biochemical properties of each GPCR constituent (i.e. protomers), these associated GPCRs exhibit discernibly different biochemical properties and are called heteromers (Ferre et al., 2009). GPCR heteromers are often observed under pathological conditions and appear to be involved in the pathophysiology of a number of diseases, including Parkinson's disease (Azdad et al., 2009), neuropathic pain (Bushlin et al., 2012), liver fibrosis (Rozenfeld et al., 2011), schizophrenia (Albizu et al., 2011), preeclampsia (AbdAlla et al., 2001), and acromegaly (Grant et al., 2008). Recently, associated GPCRs have been targeted by heterovalent ligands (Daniels et al., 2005; Jaquet et al., 2005; Yuan et al., 2013) and antibodies (Gupta et al., 2010; Berg et al., 2012), and new methodologies for targeting these entities are emerging (Donaldson et al., 2013; Lewis et al., 2014). Despite the significant success of these approaches, which have been primarily developed for neurological disorders, there are limited examples of targeting GPCR heteromers in cancer (Moreno et al., 2014). Identifying GPCR interactions within the context of human malignancies is challenging, particularly at the molecular level and in the native state (Gomes et al., 2004; Albizu et al., 2010; Sams et al., 2014; Dudok et al., 2015; Gomes et al., 2016).

To identify cancer-specific GPCR heteromers, high-resolution information along a large spatial region is desired. Single molecule pointillistic super-resolution microscopy techniques (Betzig et al., 2006; Hess et al., 2006; Rust et al., 2006; Folling et al., 2008; Wombacher et al., 2010), like direct stochastic optical reconstruction microscopy (dSTORM) (Wombacher et al., 2010; Scarselli et al., 2012; Sams et al., 2014; Tobin et al., 2014; Dudok et al., 2015; Jonas et al., 2015), are well suited for this purpose. To dissect the complex arrangement of proteins visualized in this way, Applicants utilized quantitative analysis of dSTORM data. Applied to super-resolution imaging data sets, Voronoï tessellation (Levet et al., 2015) was used to determine receptor organization and cluster sizes, while pair-correlation analysis (Sengupta et al., 2011; Sengupta et al., 2013) and Monte Carlo simulations were used to precisely interrogate interactions between receptors. This unique approach is quantitative, operates at the single molecule level, and is well suited for interrogating tight GPCR networks.

Using quantitative super-resolution microscopy, clustering of GPCRs and co-localization between GPCR pairs was evaluated in pancreatic environments: healthy cells, cancerous cells, multicellular tumor spheroids (MCTS, a 3D cell culture system (Sutherland, 1988)), and matching tissue samples from three patients. Applicants identified a heteromer between MOR and SSTR2, called MOR-SSTR2, which is specific for PDAC. To the best of their knowledge, Applicants are the first to show an association between two GPCRs and pancreatic malignancy in a native environment. In addition, it is the first time a quantitative correlation has been obtained on a molecular level between GPCR networks in cultured cells (2D and 3D environments) and matching tissue samples. Importantly, Applicants correlated the physical association between MOR and SSTR2 with signaling outcomes. According to results from biochemical experiments, activation of both MOR and SSTR2 1) correlates with signaling events unique to PDAC cells; and 2) leads to increased malignant potency of only cancerous epithelial pancreatic cells. Cumulatively, these results suggest that the MOR-SSTR2 heteromer may represent a PDAC specific therapeutic target.

Figure 18A:
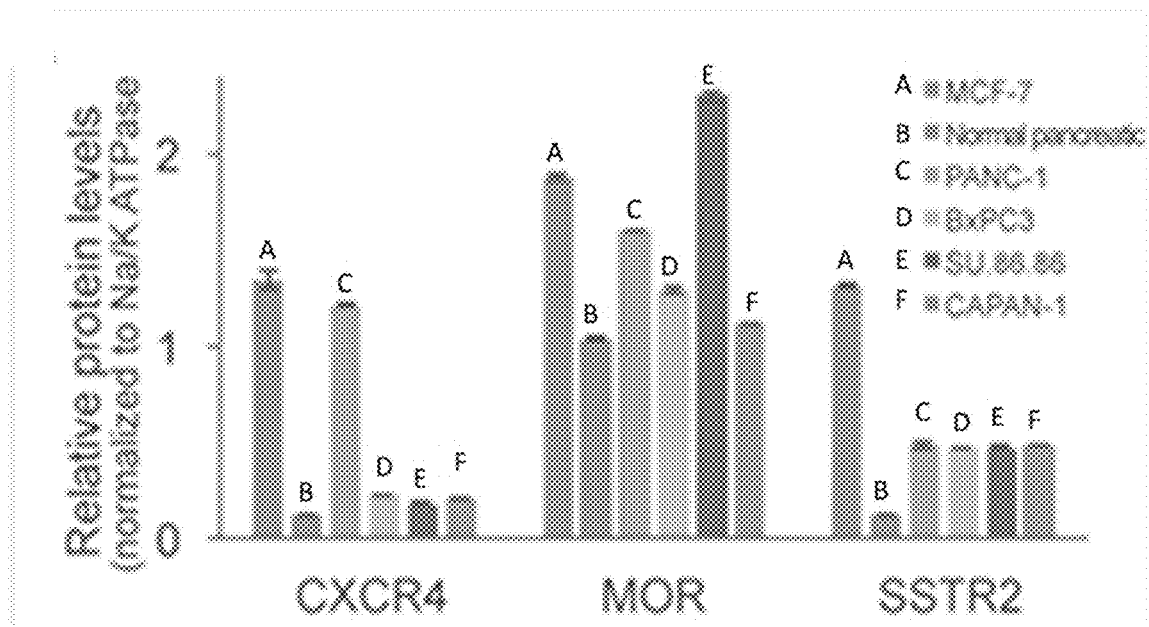
FIG. 18A-18H: Western blot quantification and unmodified scans of representative Western blots.
Figure 18B:
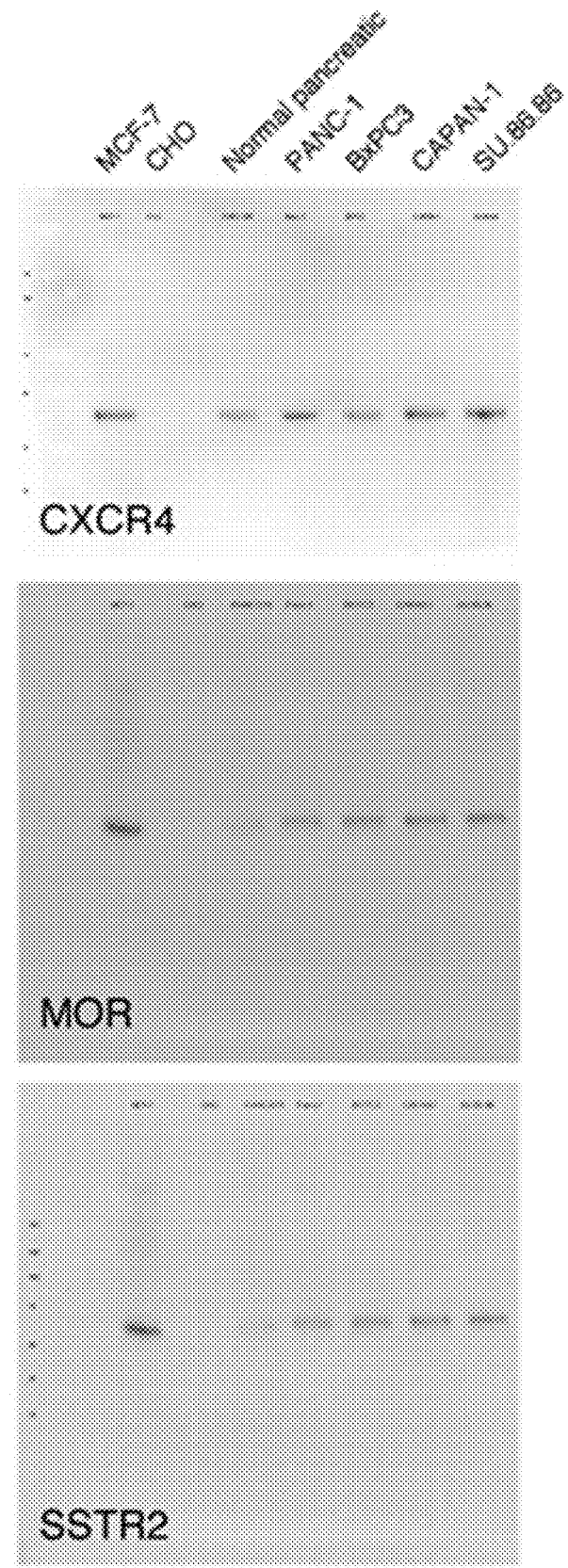
Figure 18C:
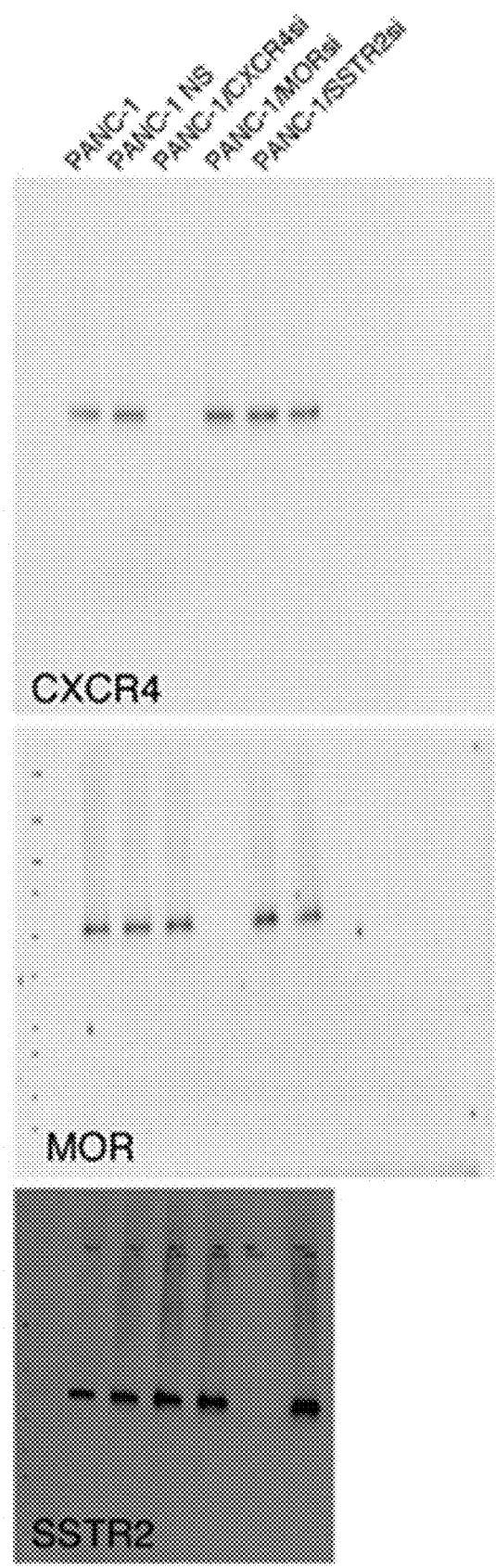
Figure 18D:
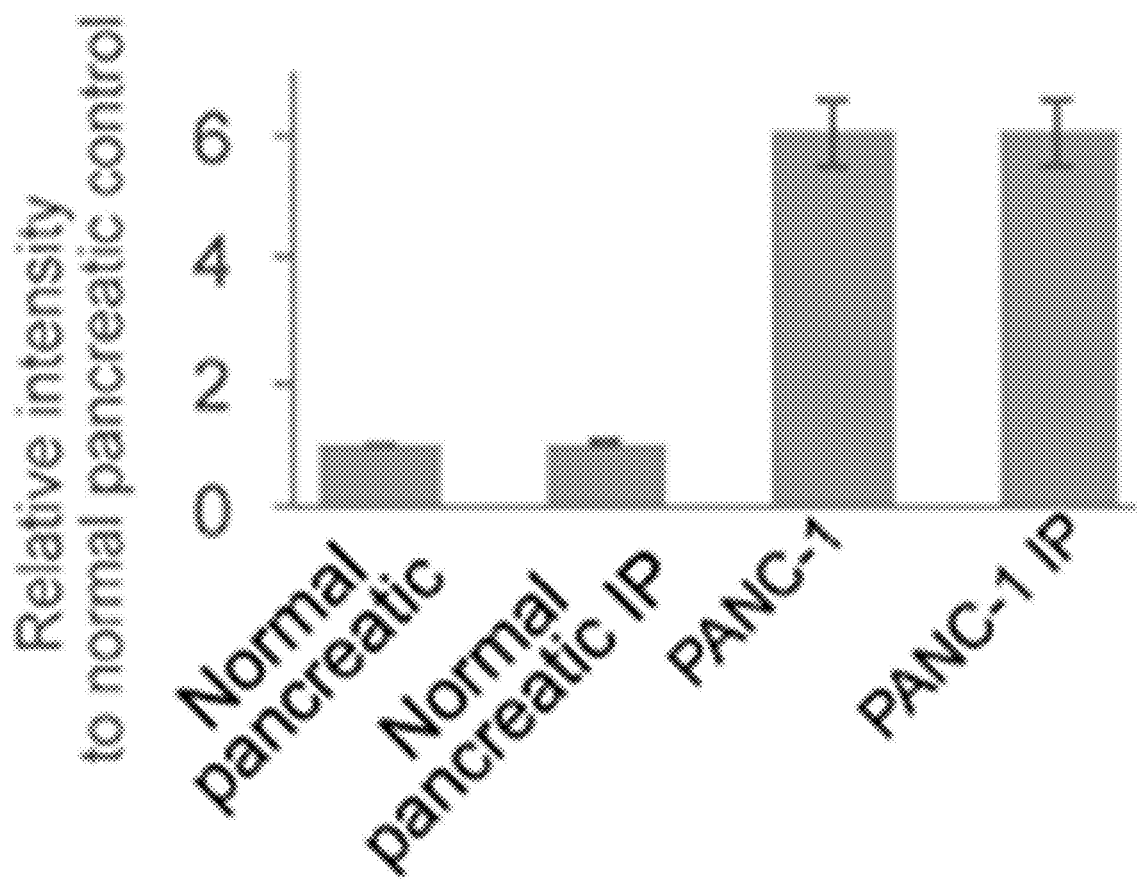
Figure 18E:
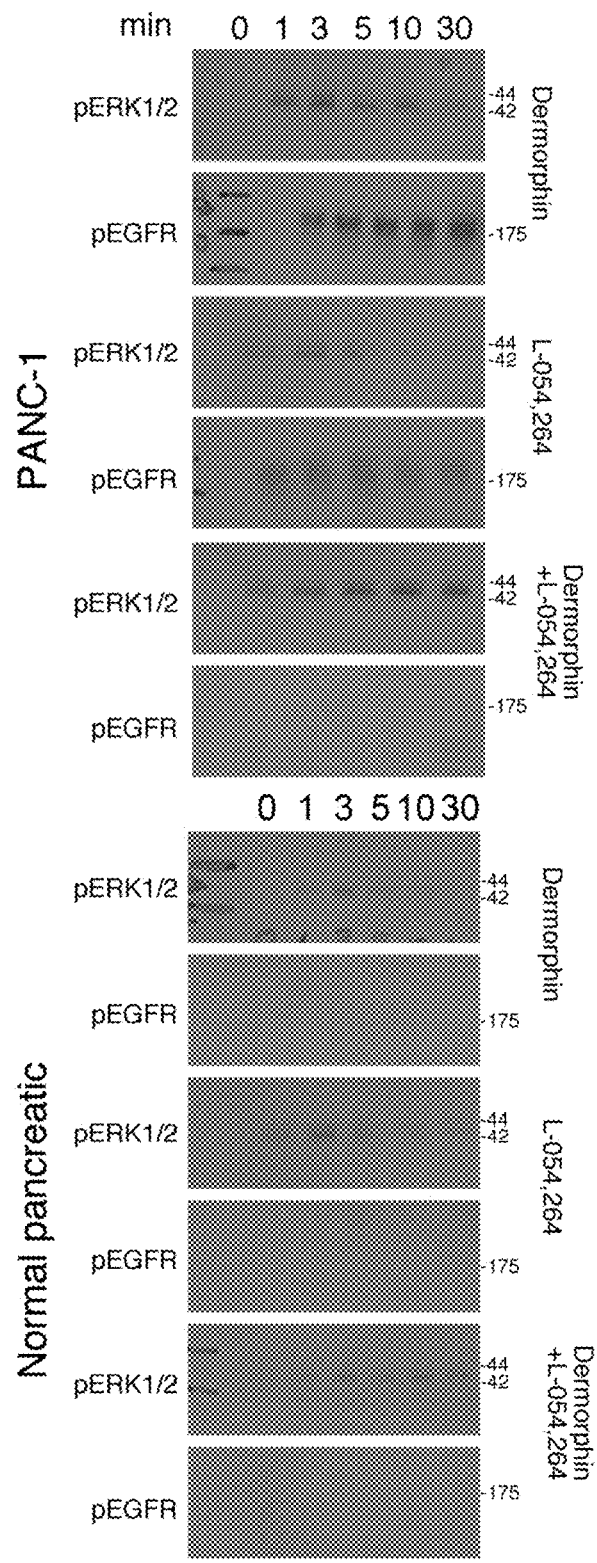
Figure 18F:
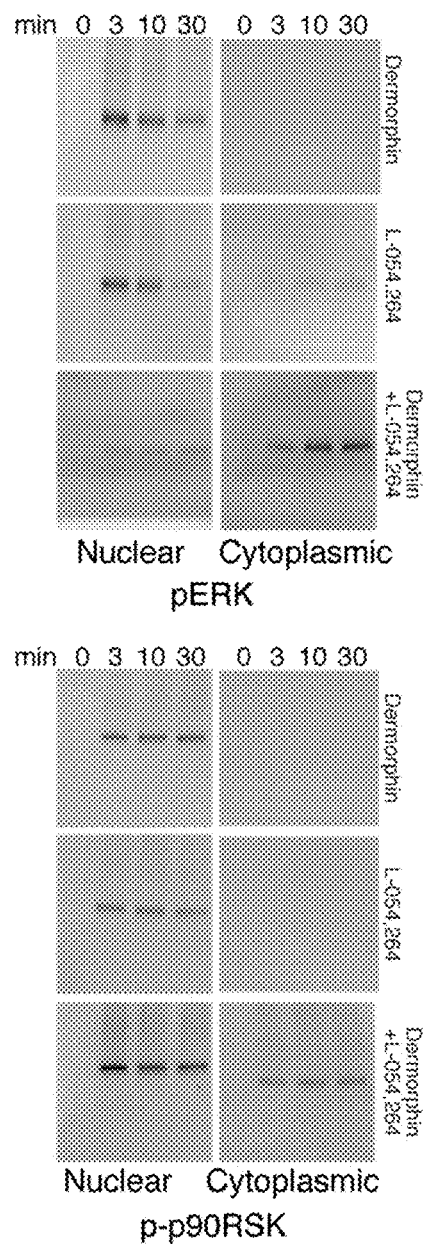
Figure 18G:
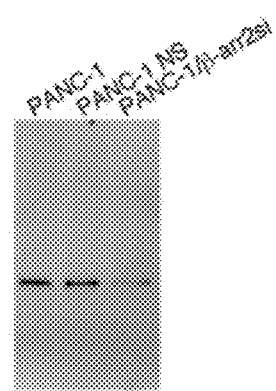
Figure 18H:
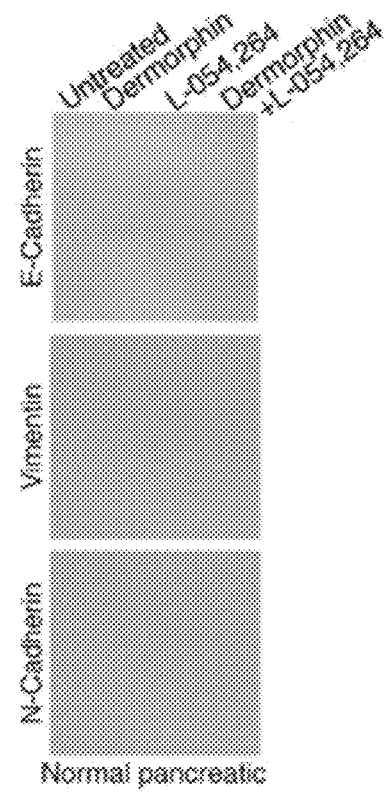
Figure 18H:
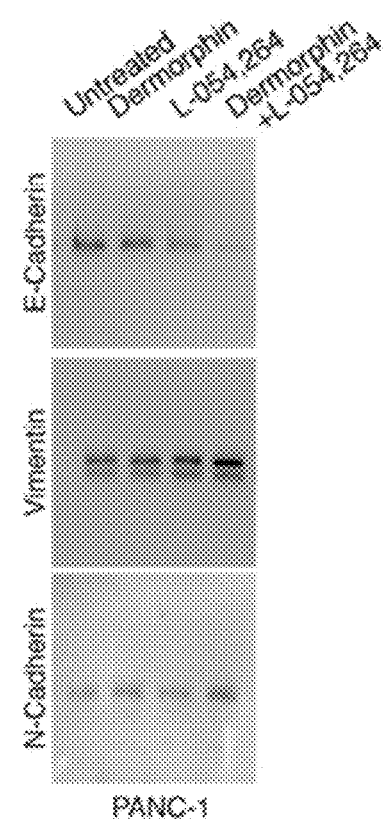
Figure 19A:
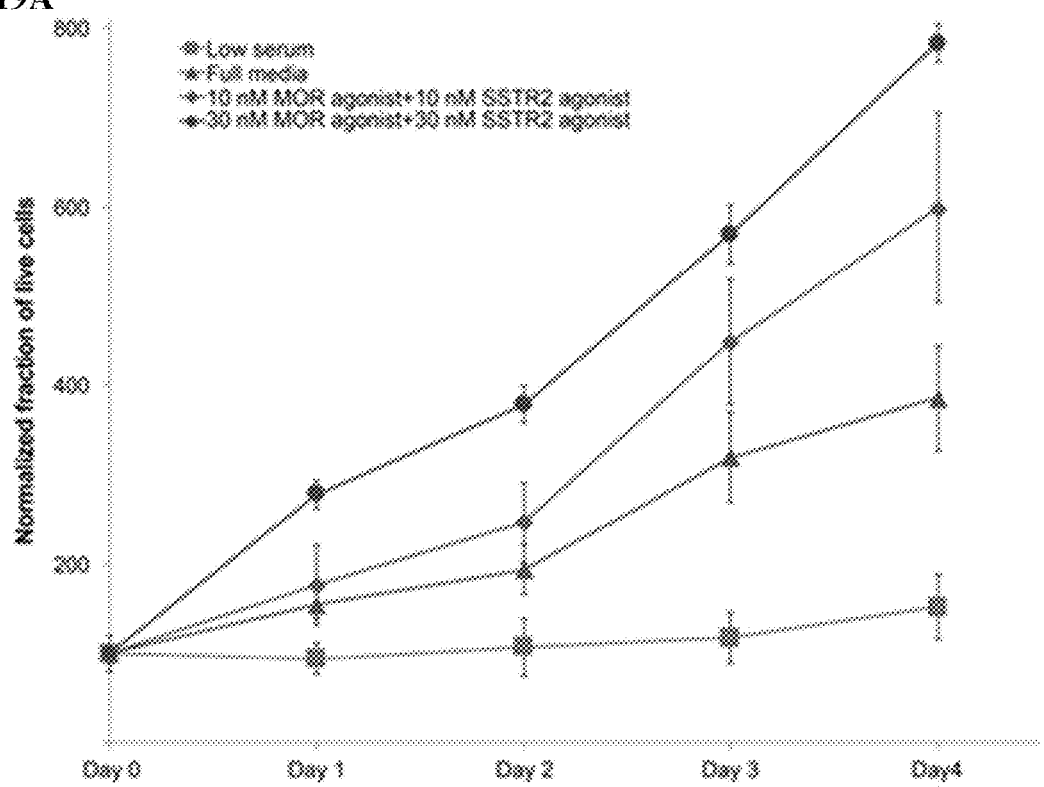
FIG. 19A-19B.
Figure 19B:
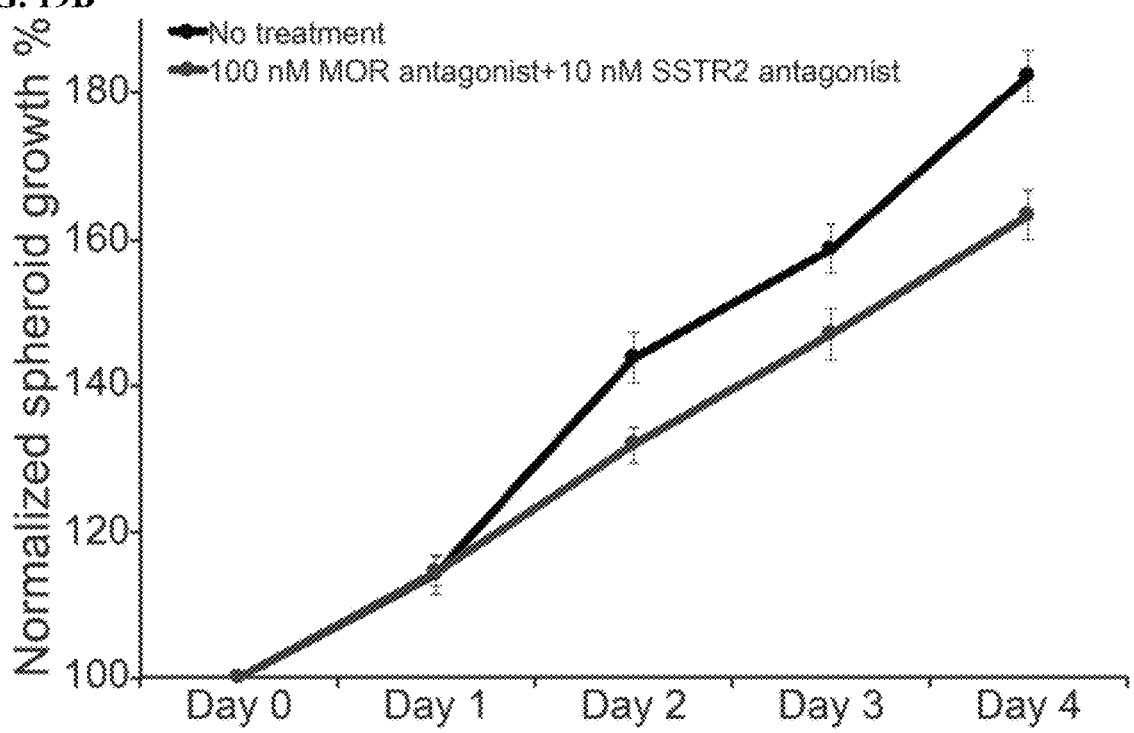

MOR, SSTR2, and CXCR4 GPCRs are More Highly Expressed in Cancer Cells than Normal Pancreatic Epithelial Cells Applicants investigated the expression and organization of MOR, SSTR2, and CXCR4 in six cell lines: 1) control CHO-S cells, 2) normal epithelial pancreatic cells, 3) PANC-1 cells, which is a PDAC cell line with K-Ras mutations (Lieber et al., 1975), 4) BxPC-3 cells, which is a PDAC cell line with no K-Ras mutations, 5) SU.86.86 cells, which is a PDAC cell line derived from metastatic liver, and 6) CAPAN-1 cells, which is a PDAC cell line derived from metastatic liver. Using RT-PCR and Western blot analysis, the expression levels of these GPCRs were evaluated. The results, which are consistent with previous reports (Koshiba et al., 2000; Li et al., 2004b; Gradiz et al., 2016), showed that SSTR2, CXCR4, and MOR were expressed at higher levels in a pancreatic cancer environment compared to normal pancreatic cells (FIG. 1A,B and FIG. 18A). No detectable expression was observed in control CHO-S cells.

Validation of dSTORM Imaging with GPCR Specific Antibodies

Figure 6A:
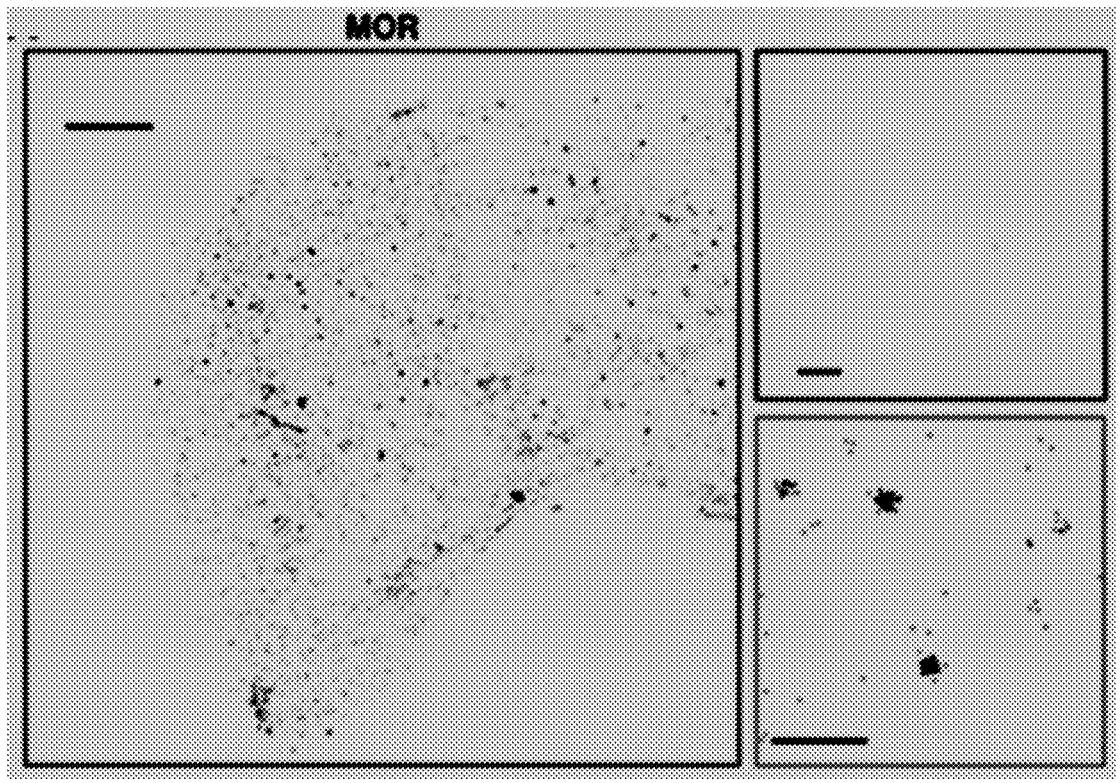
FIG. 6A-6D: Distribution of endogenous MOR, SSTR2, and CXCR4 in PANC-1 cells.
Figure 6B:
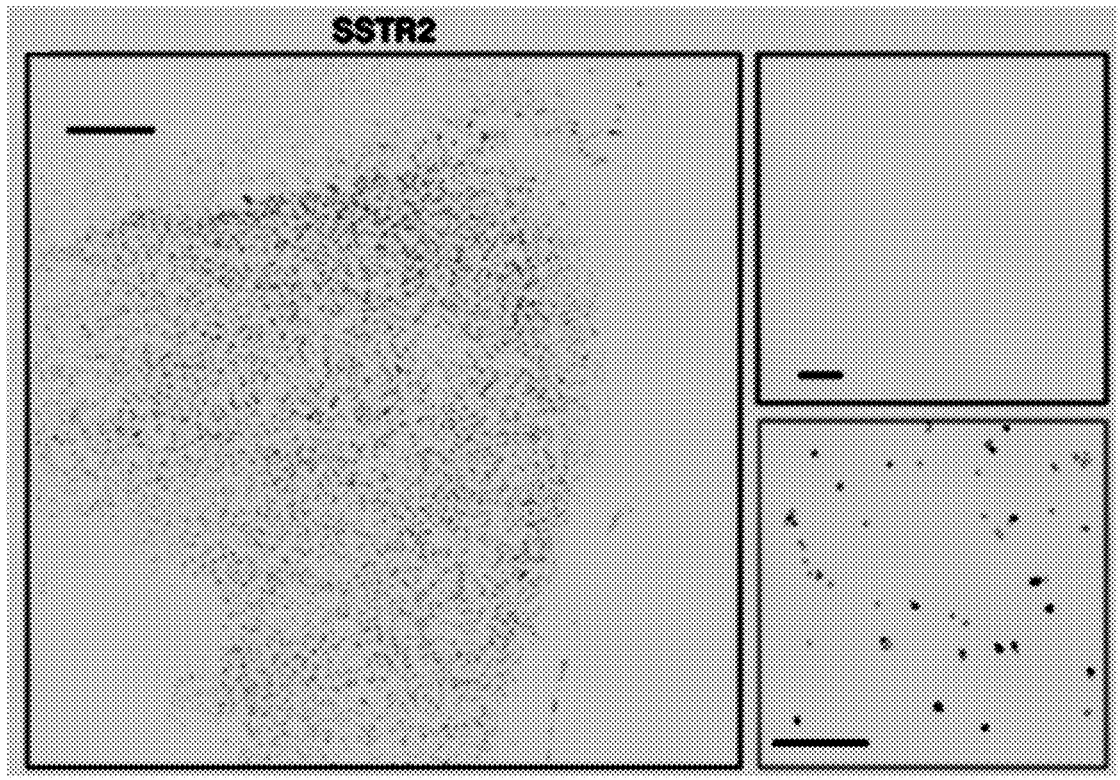
Figures 6C, 6D:
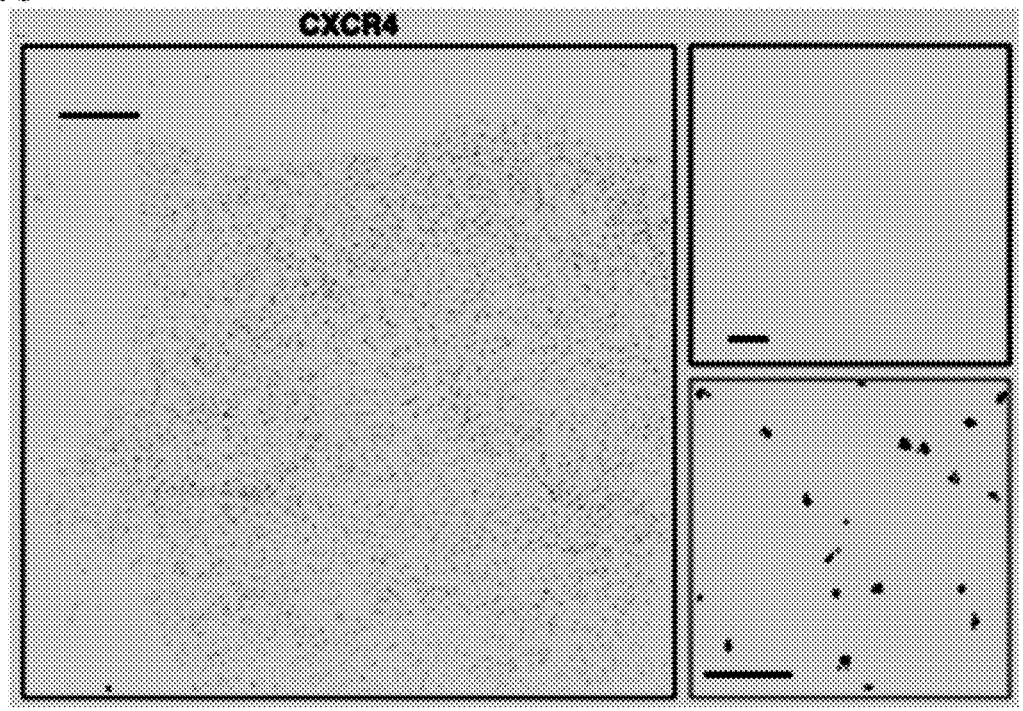
Figure 7A:
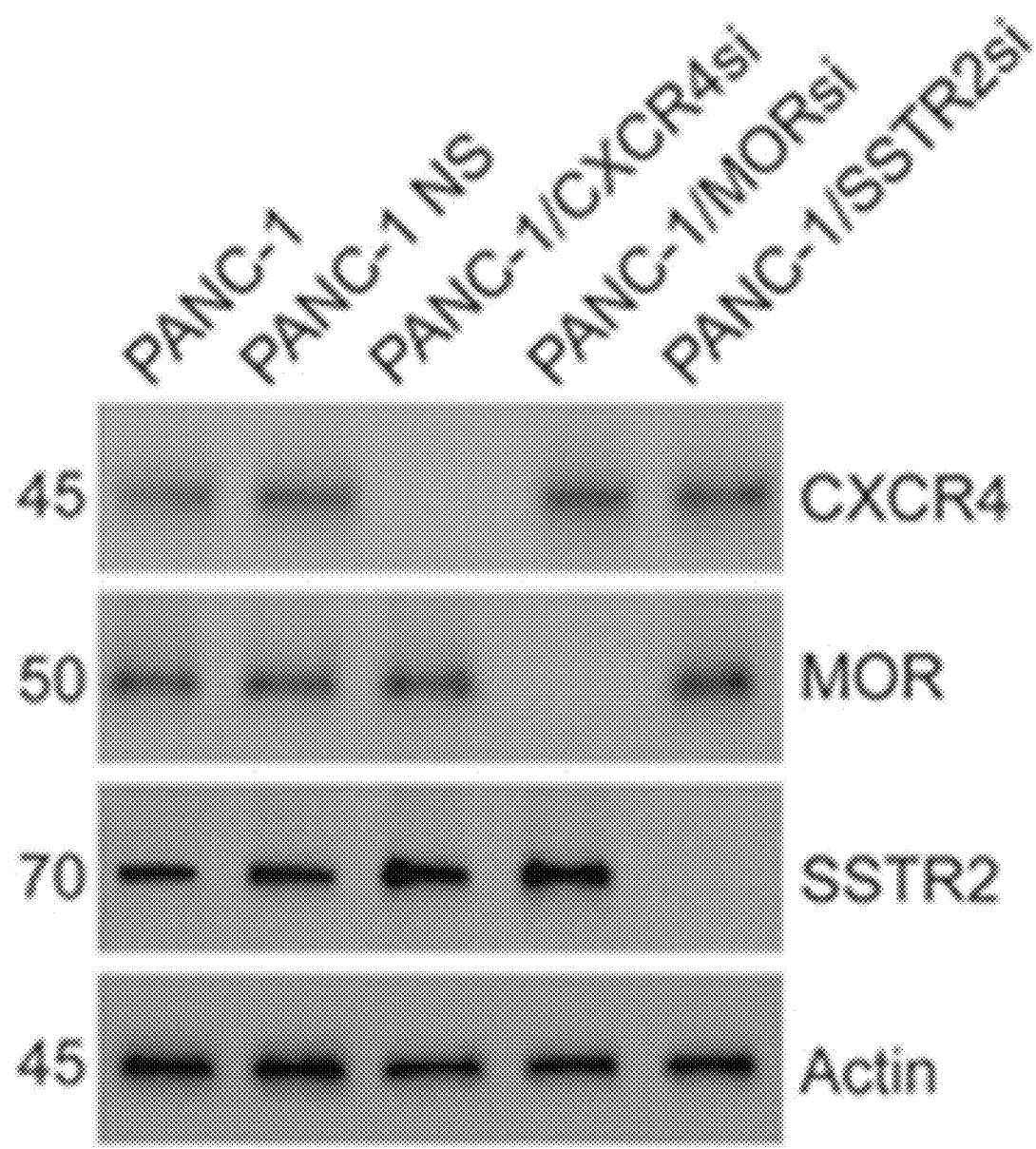
FIG. 7A-7C: Knockdowns of CXCR4, MOR, and SSTR2 in PANC-1 cells confirm antibody specificity.
Figure 7B:
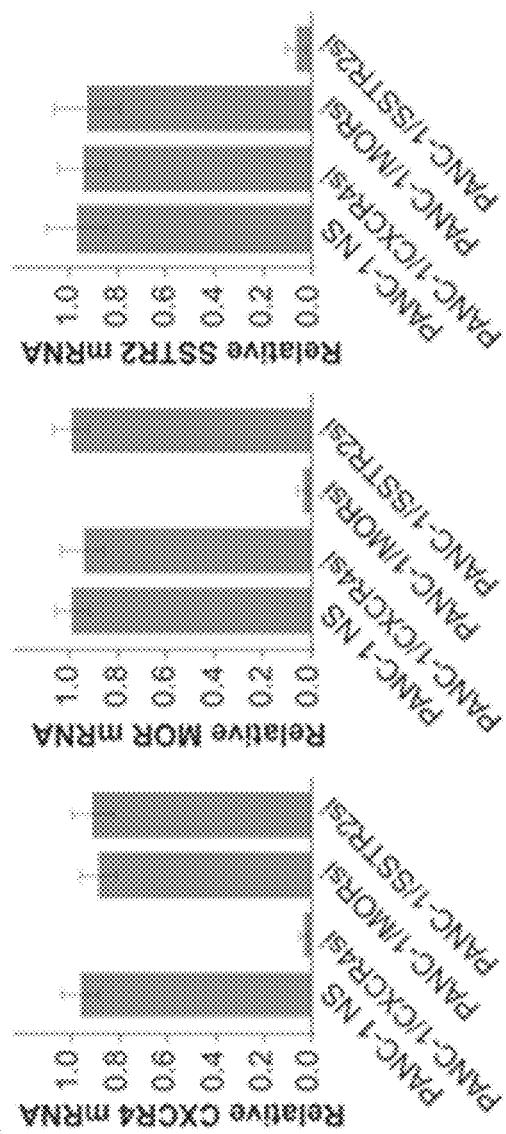
Figure 7C:
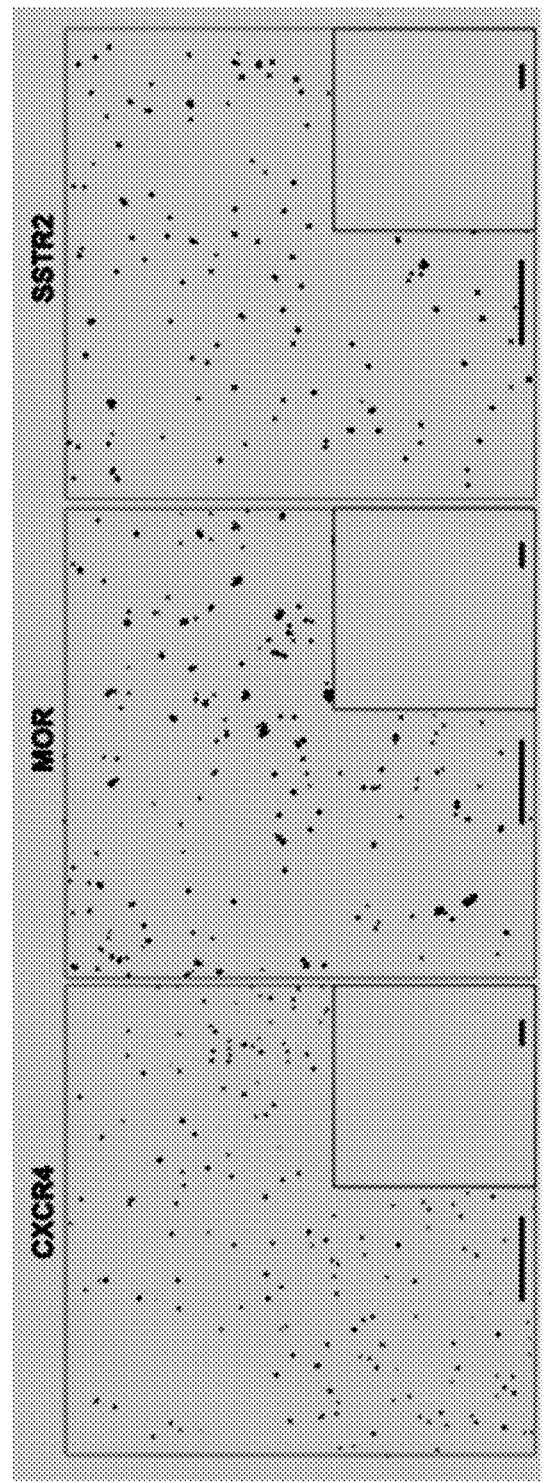

Having established higher GPCR expression levels in PANC-1 cells compared to normal pancreatic cells, the feasibility of detecting GPCRs using dSTORM was determined. As shown in FIG. 6A-C, the plasma membrane organization of the MOR, SSTR2, and CXCR4 in pancreatic cells can be observed. The three GPCRs were detected by affinity tagging with specific primary antibodies and fluorescently labeled secondary antibodies (Tobin et al., 2014; Dudok et al., 2015). The antibodies' specificities for their respective GPCRs were extensively interrogated using both blocking peptides and knockdown cells. Because blocking peptides bind to the antigen-binding region on the antibody, they interrupt antibody-GPCR interactions and are thus useful for isolating non-specific interactions. As shown in FIG. 6A-C (top right squares), no appreciable signal was observed when the antibodies were blocked with peptides, which indicates that the antibodies are specific for MOR, SSTR2, and CXCR4. In FIG. 6D an overlay of GPCR sequences with highlighted blocking peptide regions (terminal domains) is provided. Antibodies were also validated using MOR, SSTR2, and CXCR4 knockdown cells. According to both Western blots and RT-PCR analyses (FIG. 7A, B), each GPCR was knocked down in PANC-1 cells with excellent efficiency. While dSTORM imaging with non-silencing (NS) control cells produced signal comparable to wild type PANC-1 cells, no significant super-resolution signal was detected in each knockdown, which confirmed the specificity of the antibodies for the their respective GPCR (FIG. 7C). Therefore, antibody labeling and dSTORM detection can be a valid approach for determining the organization of GPCRs in pancreatic cancer.

MOR and SSTR2 Show Distinct Signatures in Malignant Pancreatic Environments

Figure 1B:
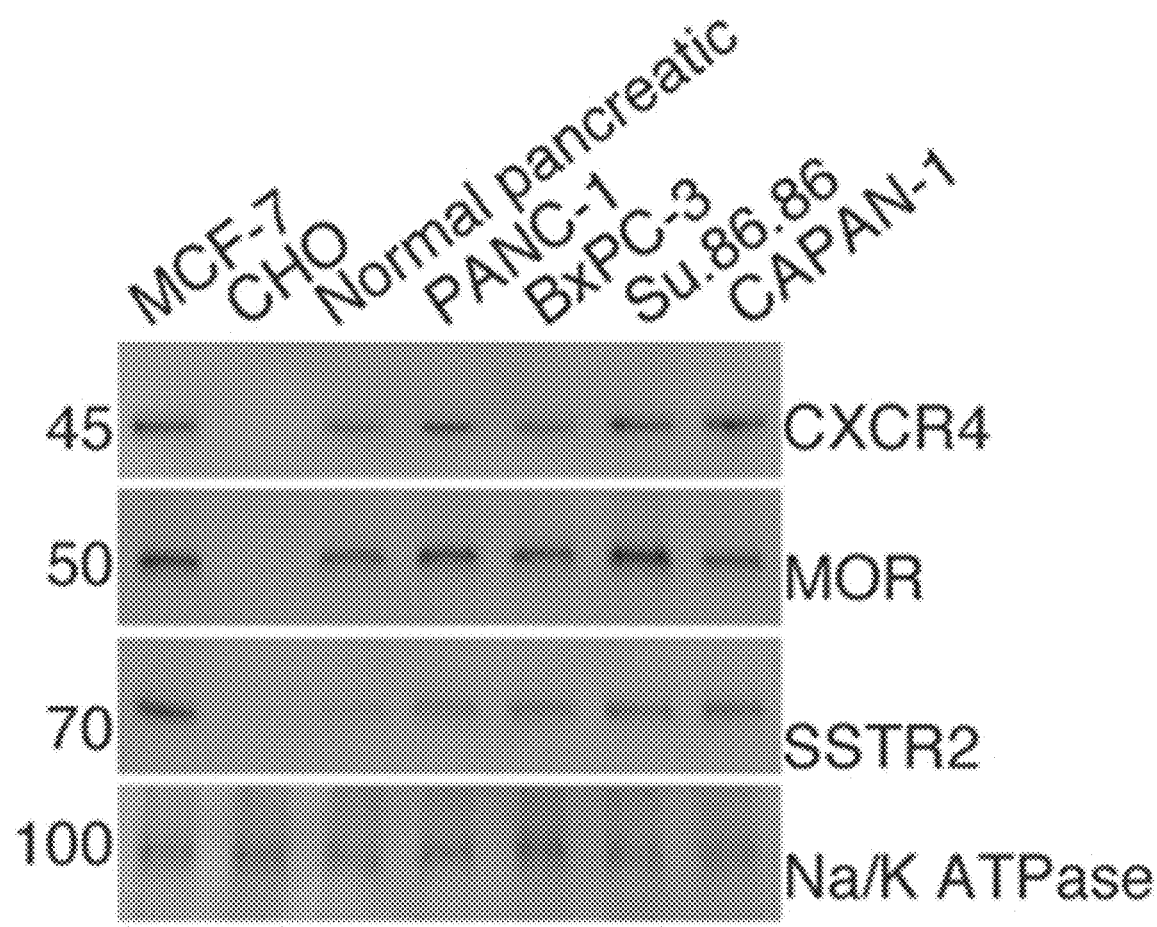
Figure 2A:
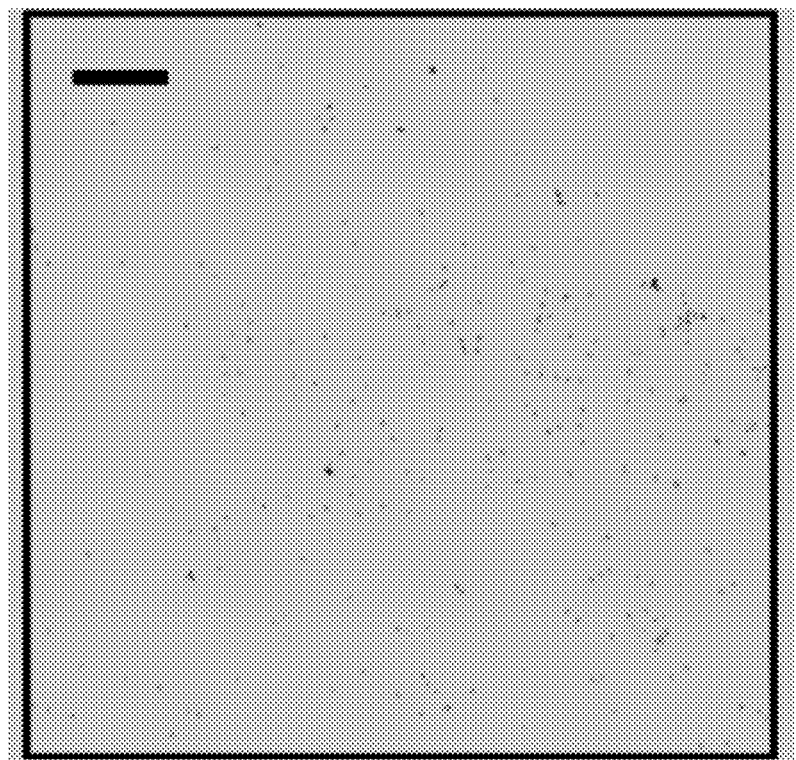
FIG. 2A-2D: Co-localization of MOR and SSTR2.
Figure 2B:
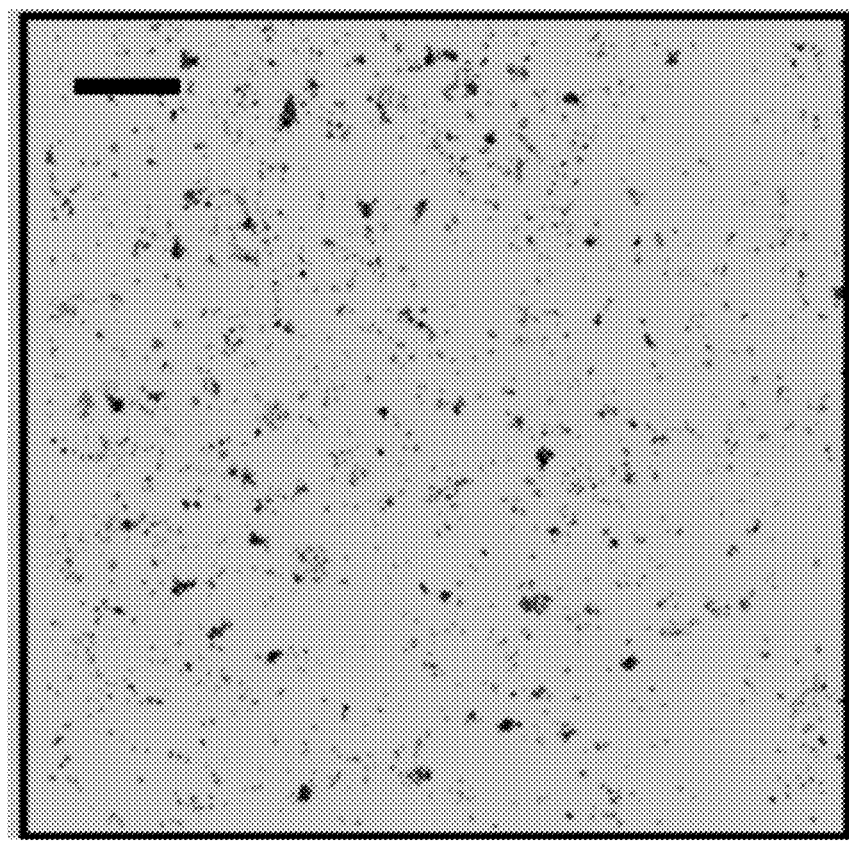
Figure 8A:
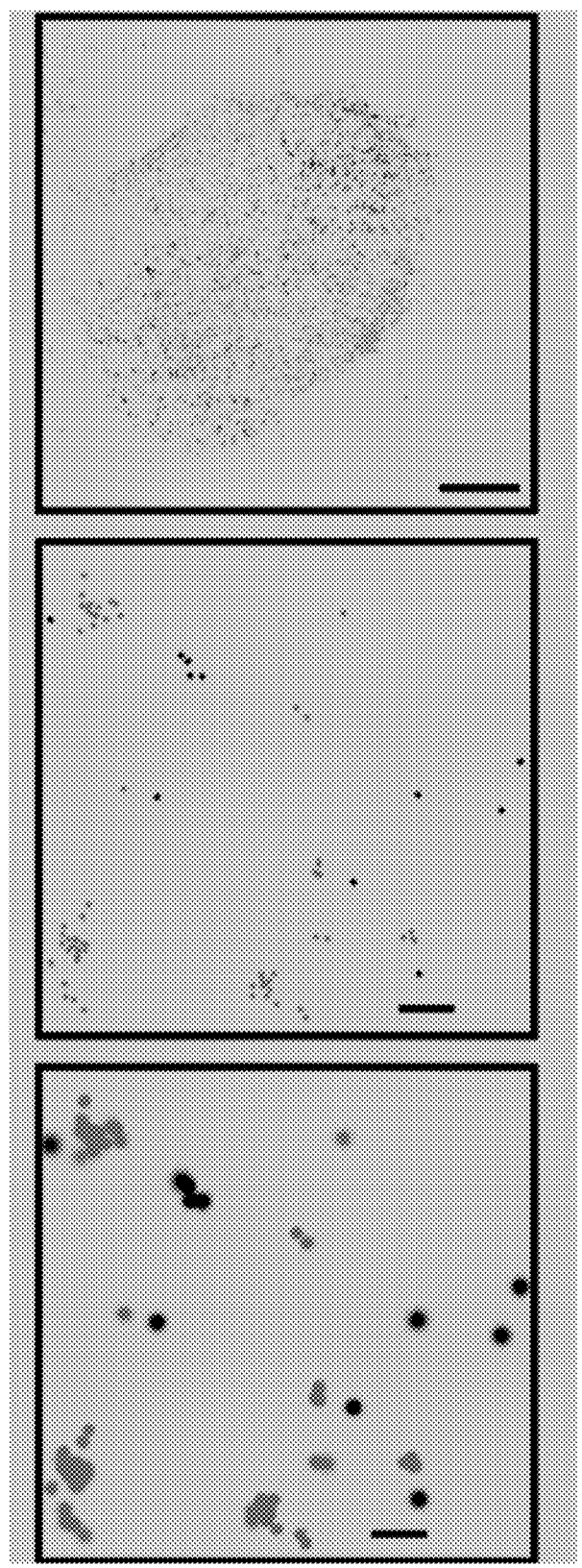
FIG. 8A-8B: Distribution of SSTR2 and MOR in pancreatic cells.
Figure 8B:
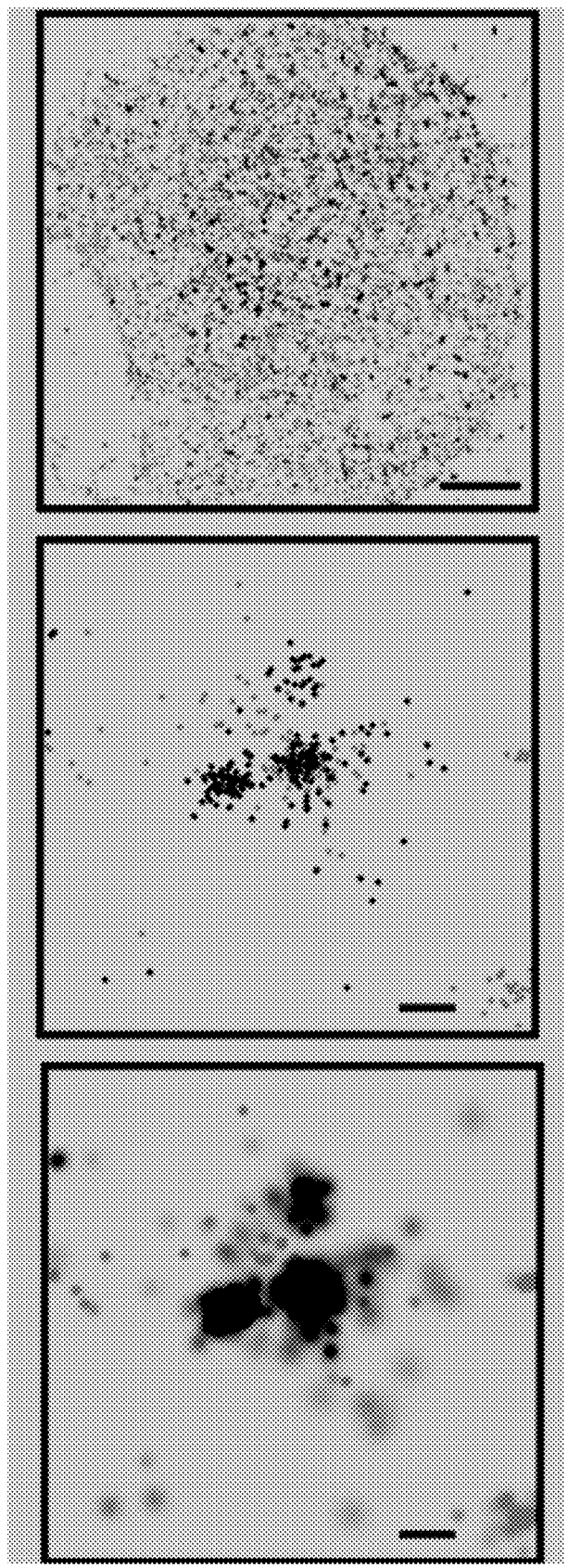
Figure 9A:
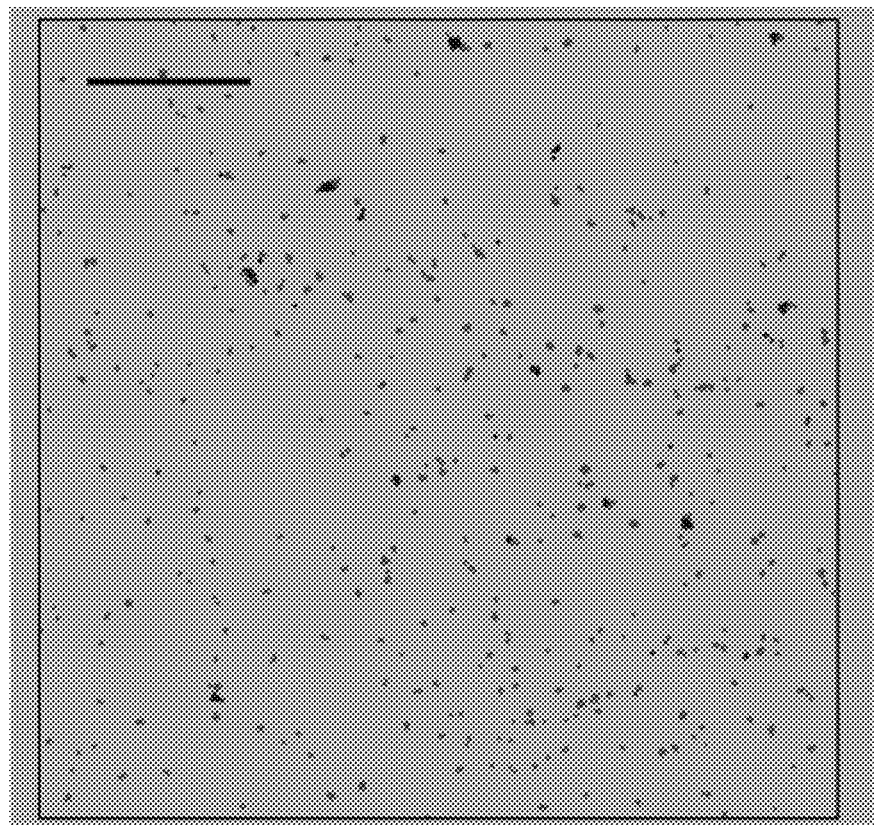
FIG. 9A-9D: Imaging of MOR/SSTR2 and MOR/CXCR4 in PANC-1 MCTS.

To determine receptor organization and their interactions, Applicants acquired two color dSTORM images. The far-red photoswitchable organic dye Alexa Fluor 647 and spectrally distinct photoswitchable organic dye Atto 488 were used as reporters. The distribution of MOR and SSTR2 was detected in normal pancreatic cells, malignant PANC-1 cells, and three-dimensional cultures of PANC-1 cells, i.e. MCTS (FIG. 2A,B, FIGS. 8 and 9A). Consistent with results from Western blot and RT-PCR analyses (FIG. 1), dSTORM revealed significantly lower surface density of both MOR and SSTR2 in normal pancreatic cells compared to PANC-1 cells. While all cells showed receptor clustering, only in PANC-1 cells and PANC-1 MCTS was the overlap between MOR and SSTR2 evident. Applicants next used Voronoï tessellation, with the fast, unbiased, and freely available software tool SR-Tesseler (Levet et al., 2015), to quantitatively compare receptor organization in various cell types. A clustered distribution with an average cluster radius ranging between 35 and 55 nm was observed in all cell types (FIG. 10). A significantly higher average cluster size was detected for MOR compared to SSTR2 in PANC-1 cells and PANC-1 MCTS but not in normal pancreatic cells. Moreover, both MOR and SSTR2 had significantly higher cluster circularity in PANC-1 cells and PANC-1 MCTS compared to normal pancreatic cells. These features suggest a differential distribution of MOR and SSTR2 in healthy versus cancerous cells and may reflect their organization into distinct signaling domains in cancerous cells.

Figure 2C:
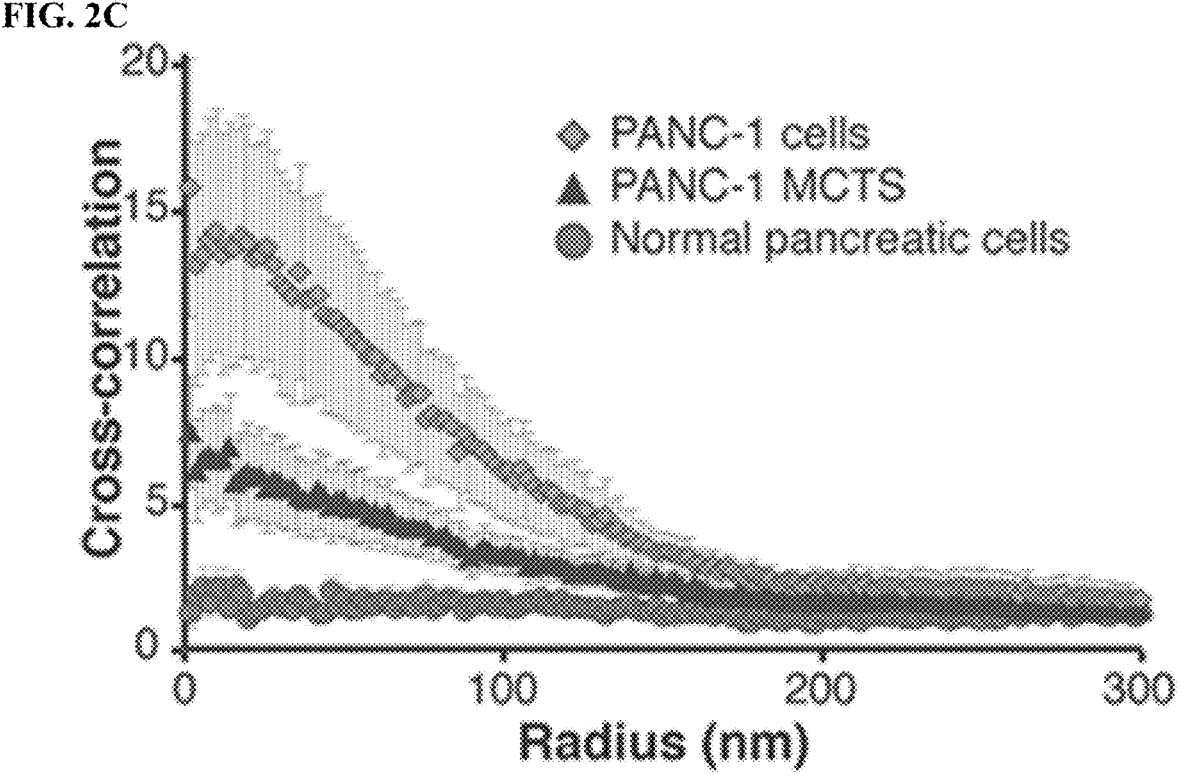

In both HEK-293 cells (Pfeiffer et al., 2002) and possibly in some breast cancer cell lines (Kharmate et al., 2013), MOR and SSTR2 have been shown to form heterodimers. Heterodimerization of MOR and SSTR2 cross-modulates phosphorylation, internalization, and desensitization (Pfeiffer et al., 2002), and it appears to be involved in anti-proliferative pathways in breast cancer (Kharmate et al., 2013). To quantitatively examine whether such interactions are present in pancreatic cancer cells and MCTS, co-localization between MOR and SSTR2 was evaluated by PC-dSTORM in 80 µm² cell regions (Sengupta et al., 2011; Tobin et al., 2014; Stone and Veatch, 2015). The results demonstrate that co-localization between the receptors does not occur (correlation curve approximately equal to 1) in normal pancreatic cells (FIG. 2C). In contrast, MOR and SSTR2 co-localize (correlation curve above 1) in malignant PANC-1 cells and PANC-1 MCTS (FIG. 2C).

Figure 2D:
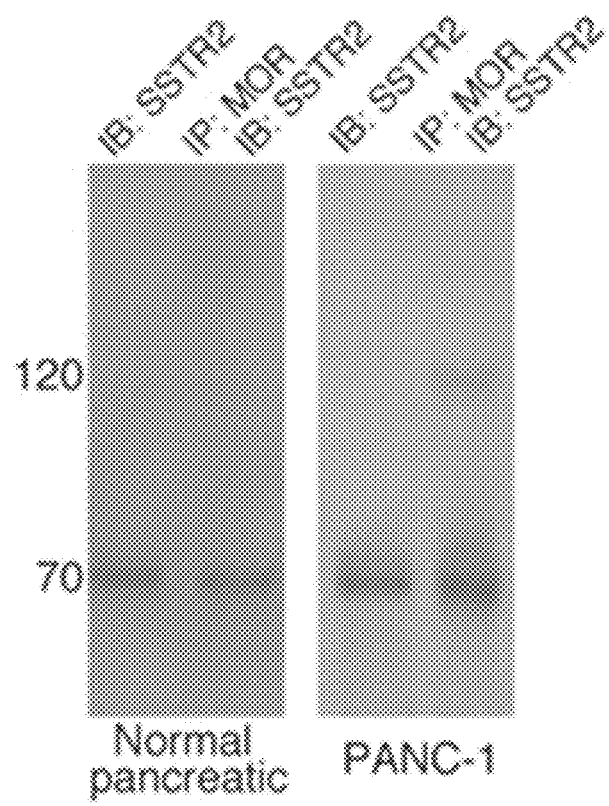
Figure 11A:
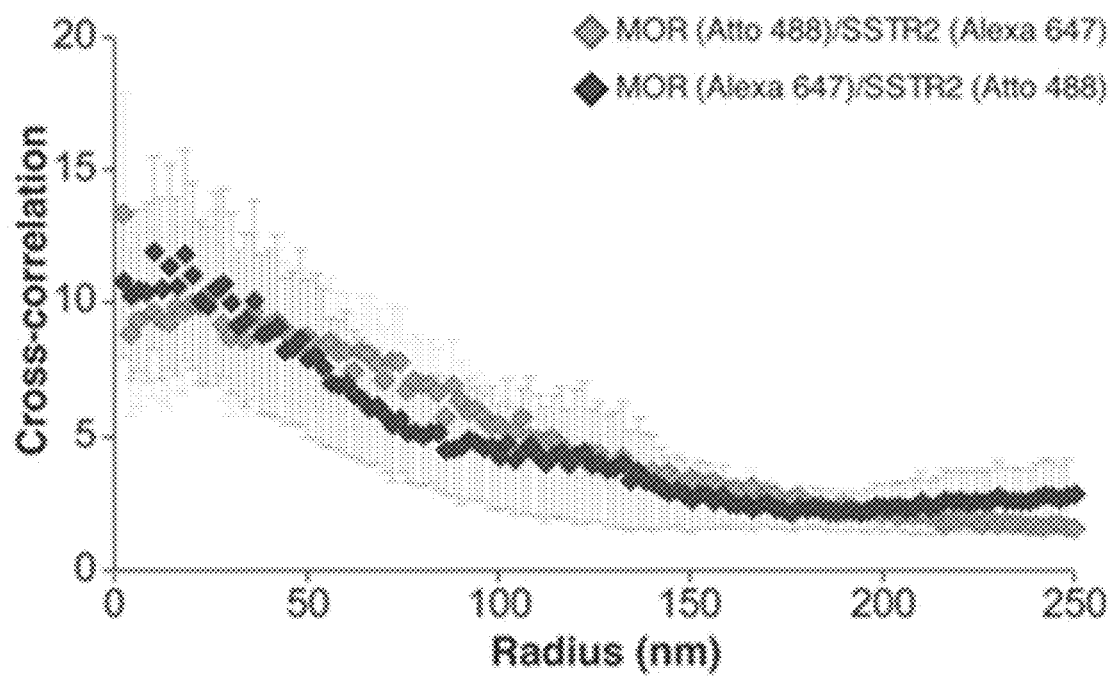
FIG. 11A-11C: Choice of label does not influence co-localization between MOR and SSTR2.
Figure 11B:
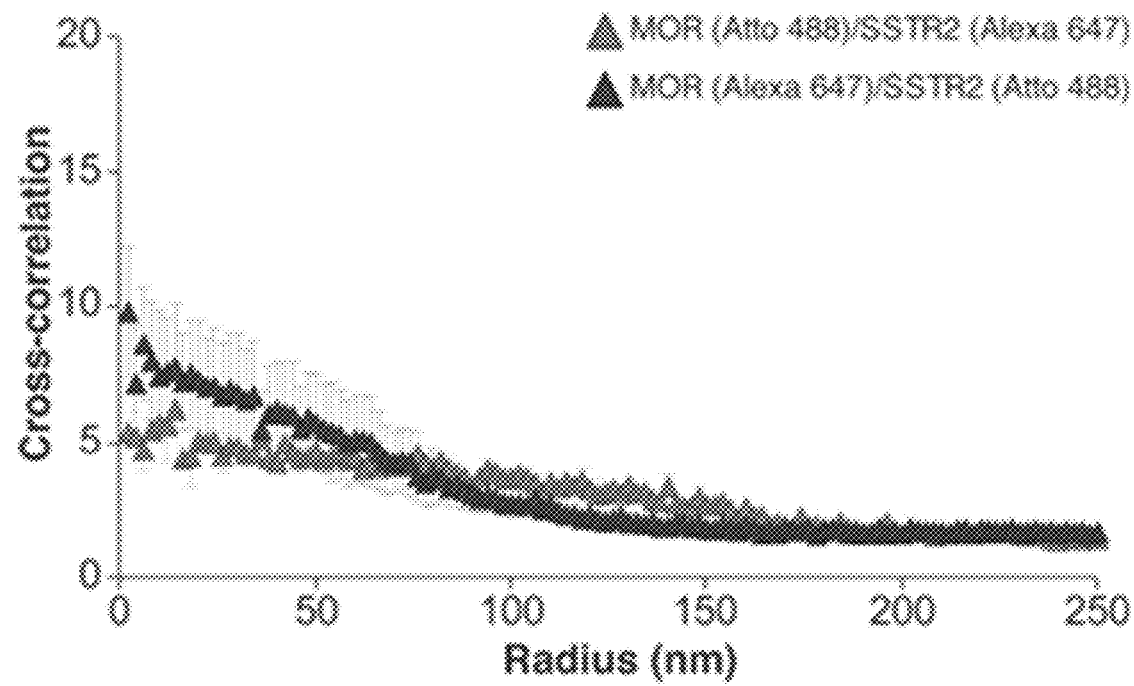
Figure 11C:
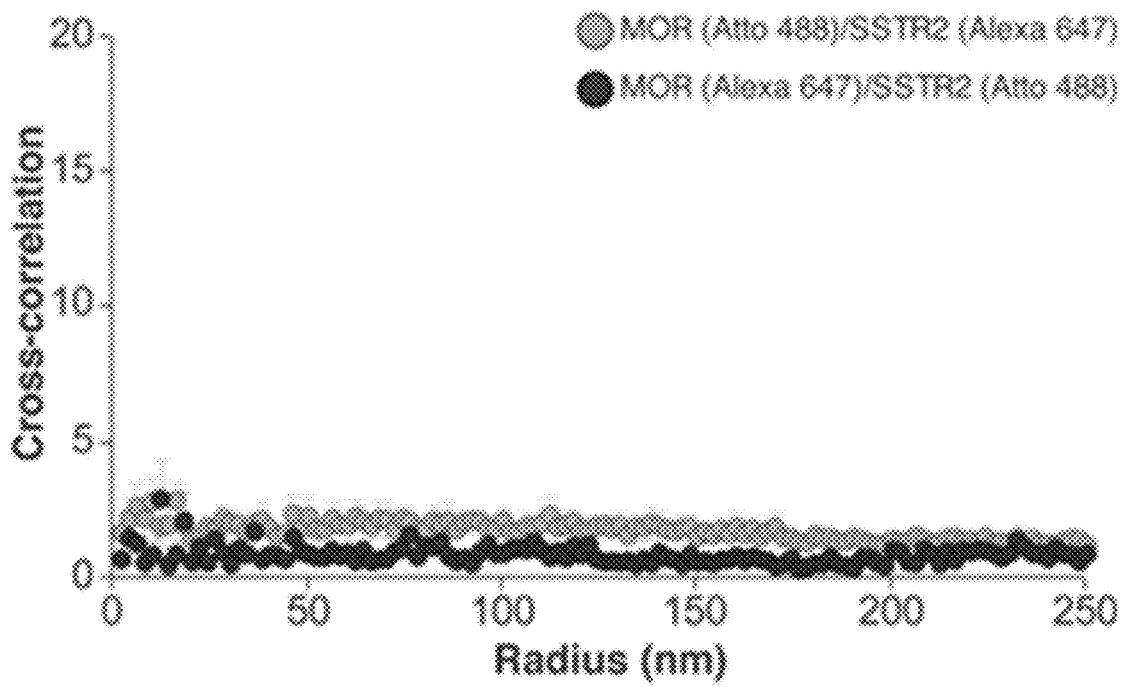
Figure 12A:
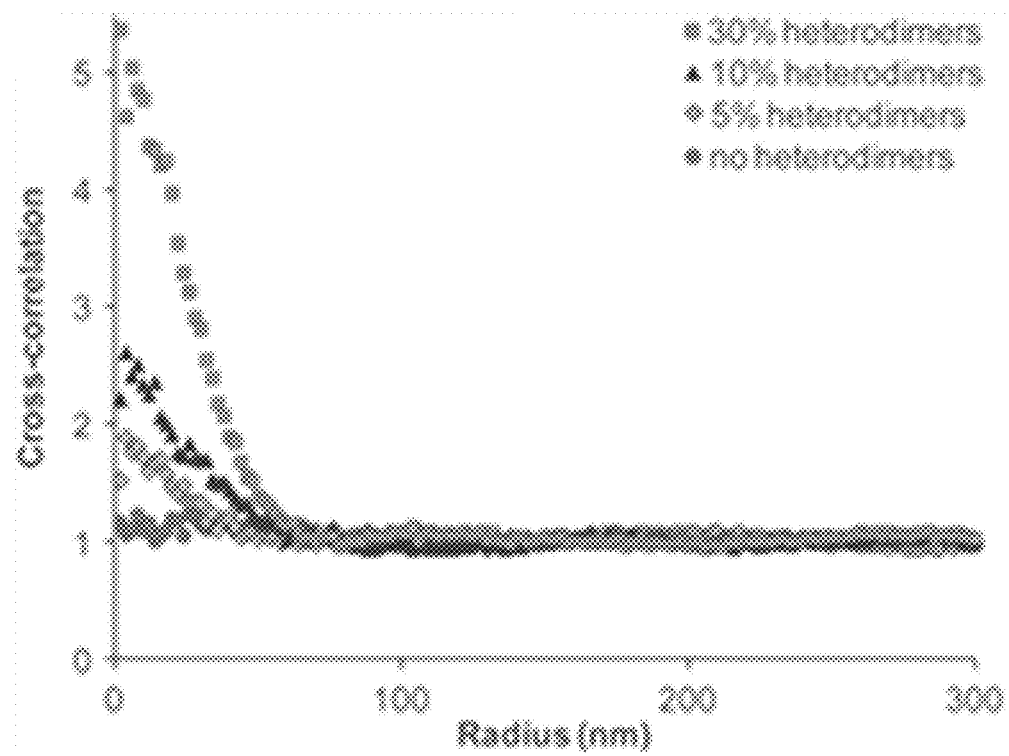
FIG. 12A-12H: Cross-correlation analysis is robust. Cross-correlation curves were obtained from Monte-Carlo simulations. In all cases Applicants simulated two channels: one generated with receptor R and another generated with receptor G. Applicants then computed a cross-correlation curve from the image with R and G combined assuming different antibody binding efficiencies and receptor densities. In all cases the cross-correlation curve equaled 1 when no heterodimers were present; the cross-correlation curves were greater than 1 when Applicants had 5%, 10%, or 30% heterodimers. Applicants assumed the following hypotheses, which operate under eight different cases.
Figure 12B:
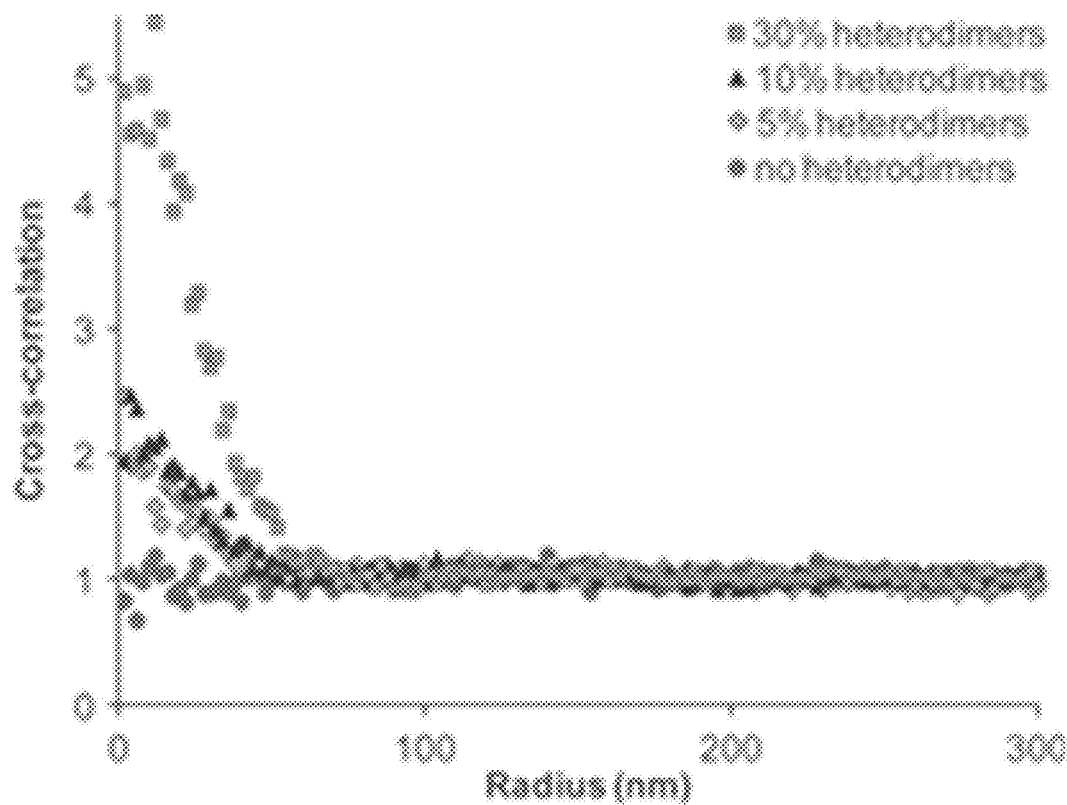
Figure 12C:
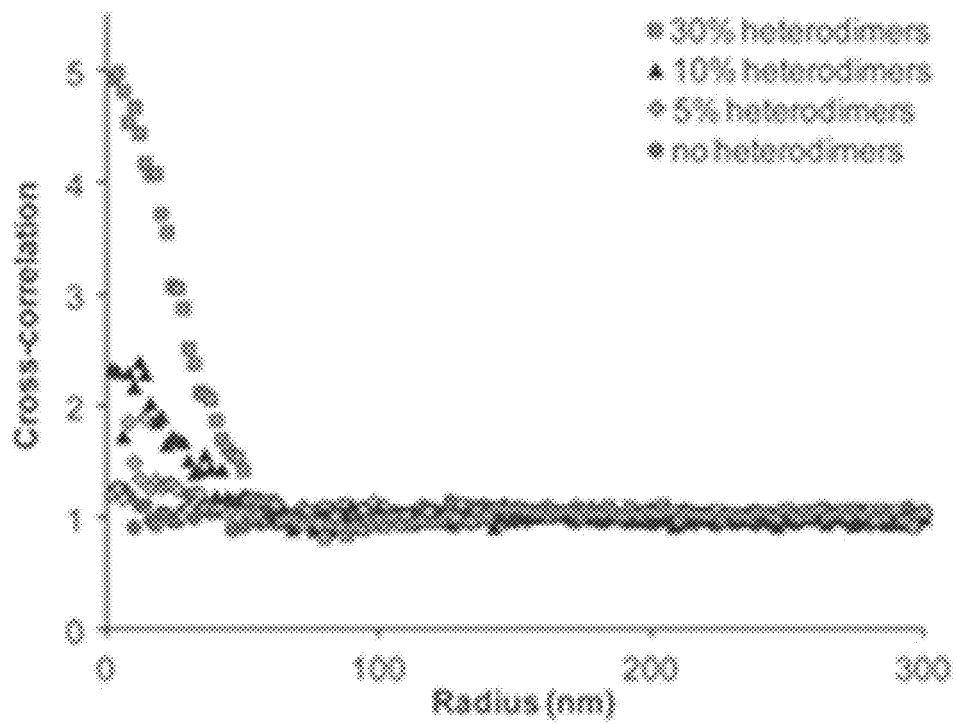
Figure 12D:
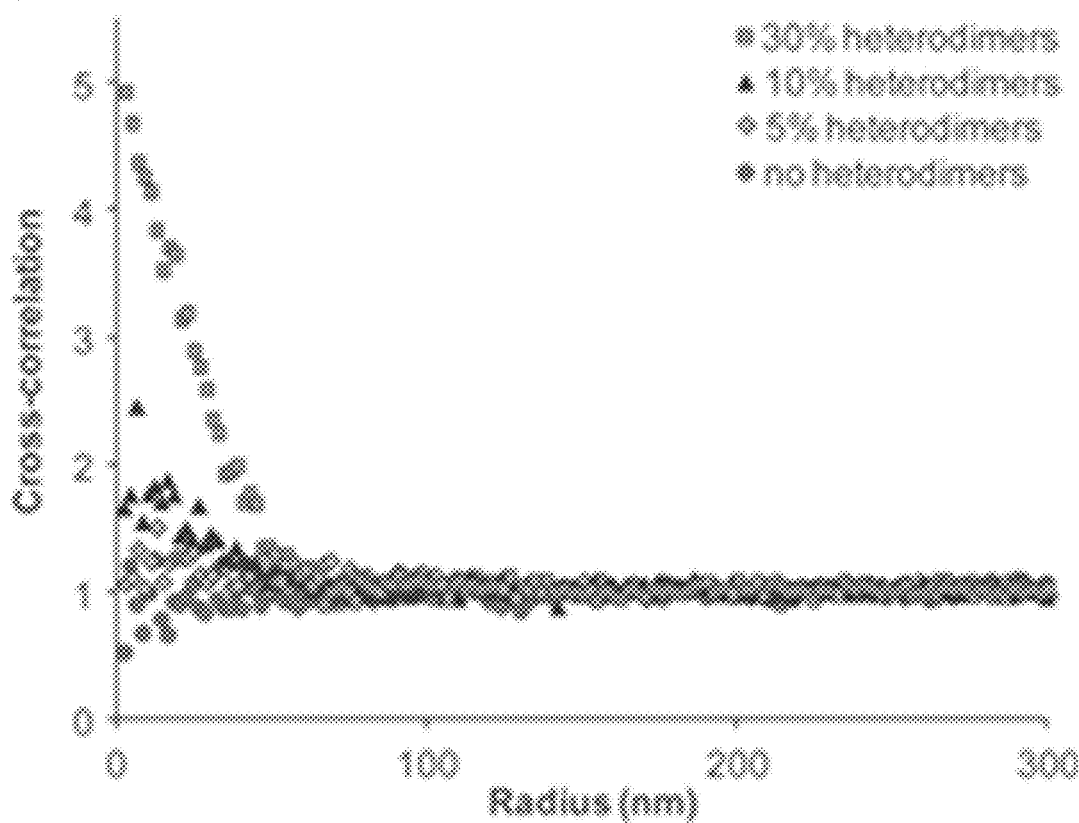
Figure 12E:
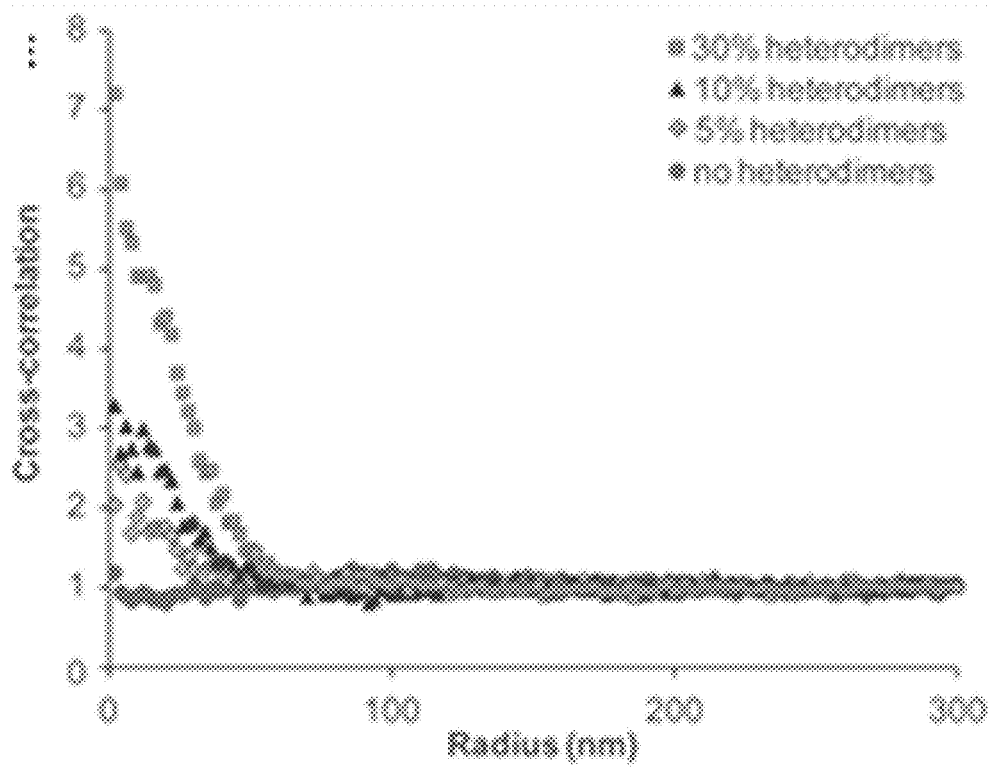
Figure 12F:
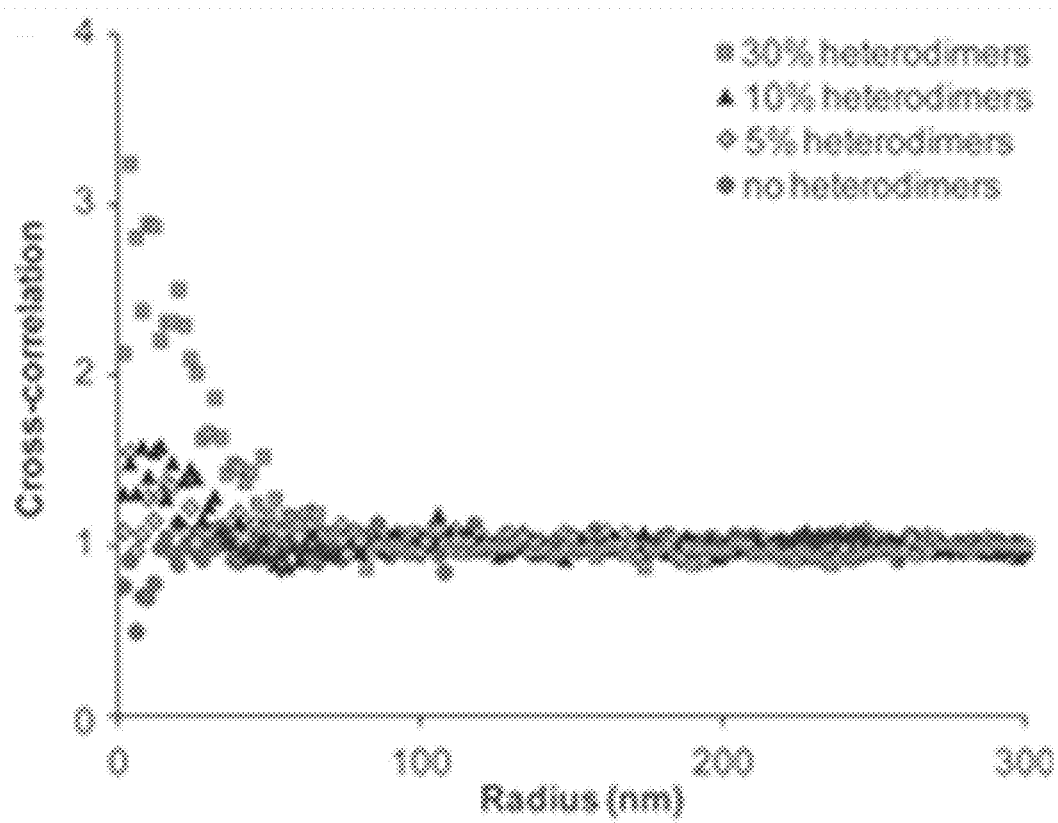
Figure 12G:
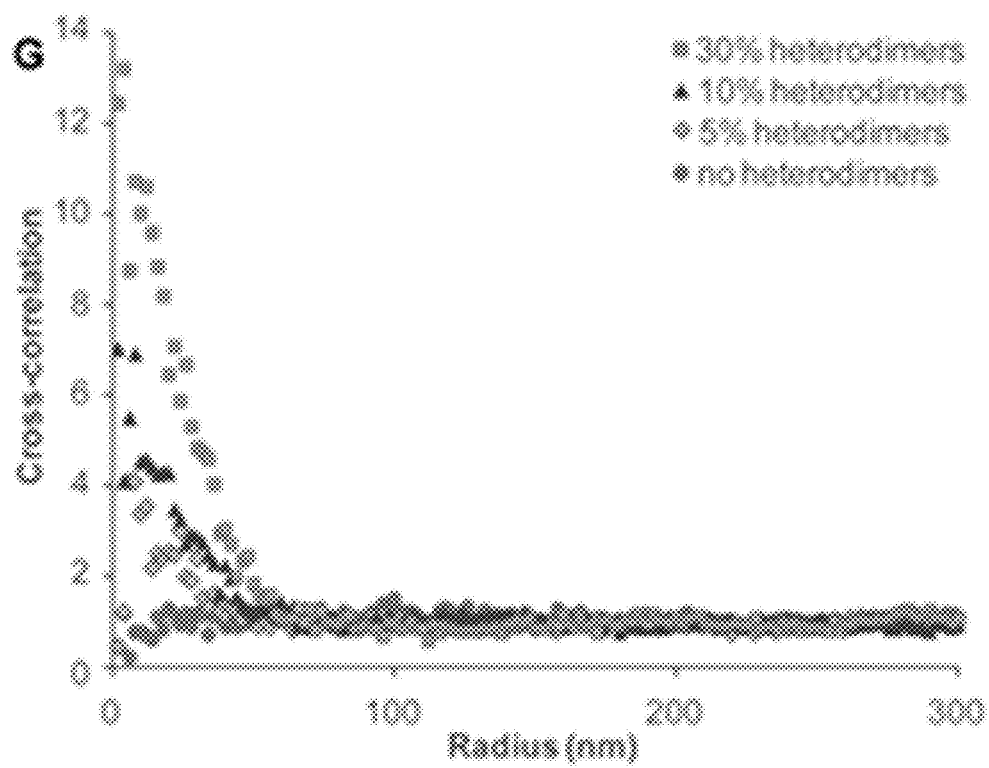
Figure 12H:
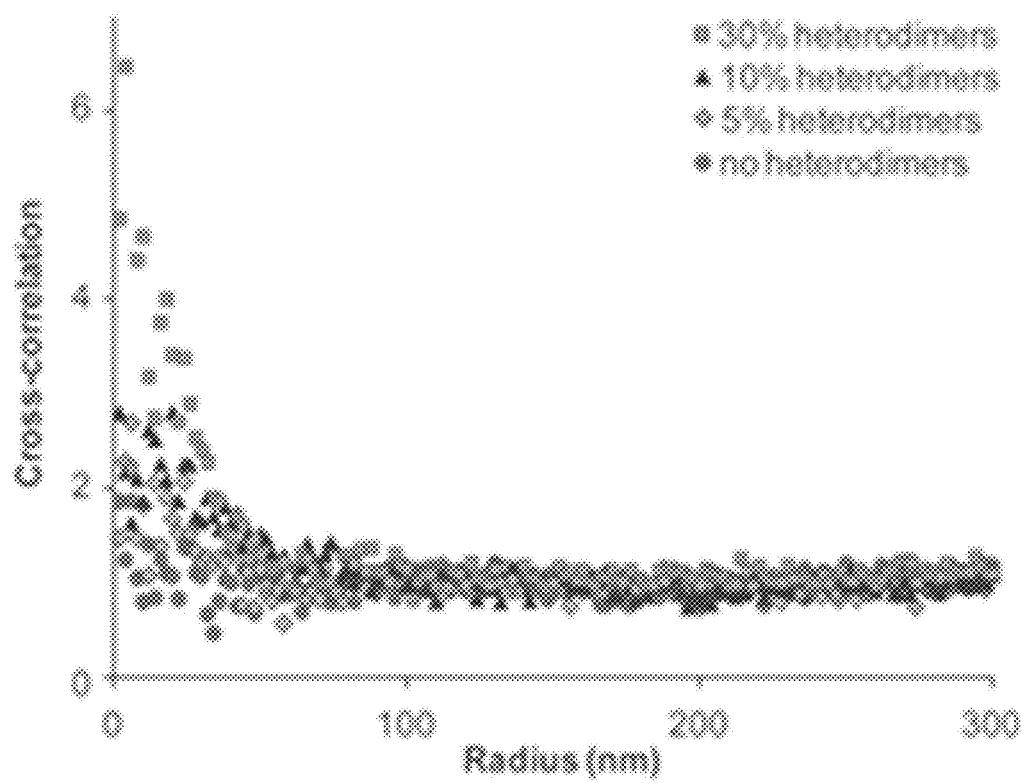

Co-localization between MOR and SSTR2 was confirmed through multiple control experiments. A combination of Atto 488 and Alexa Fluor 647 has been extensively used without issues for two-color super-resolution imaging (Dempsey et al., 2011; Dudok et al., 2015). Consistently, spectral overlap between the two channels was not observed under our acquisition conditions. To investigate whether specific combinations of colors influenced the outcome, first MOR was detected with Atto 488 while SSTR2 was detected with Alexa Fluor 647; next MOR was detected with Alexa Fluor 647 while SSTR2 was detected with Atto 488. As shown in FIG. 11, the choice of labeling scheme did not influence the correlation curve for normal pancreatic cells, PANC-1 cells, and PANC-1 MCTS. Thus the averaged data from both labeling schemes was combined (FIG. 2C and FIG. 10). In addition to these experimental labeling controls, Monte Carlo simulations were used to examine the impact of antibody detection efficiency on the ability to detect heteromers. As provided in FIG. 12, an extensive set of conditions were simulated and evaluated. For example, both 20% and 50% detection efficiencies are capable of detecting as little as 5-10% heteromers. As expected, for a simulated system in which there was no co-localization, detection efficiency was not a relevant parameter. Finally, co-immunoprecipitation experiments were used to further establish co-localization between MOR and SSTR2 in pancreatic cancer cells: MOR co-immunoprecipitated with SSTR2 only in malignant, PANC-1 cells (FIG. 2D).

MOR and CXCR4 do not Co-Localize in Pancreatic Cells and PANC-1 MCTS

Figure 3A:
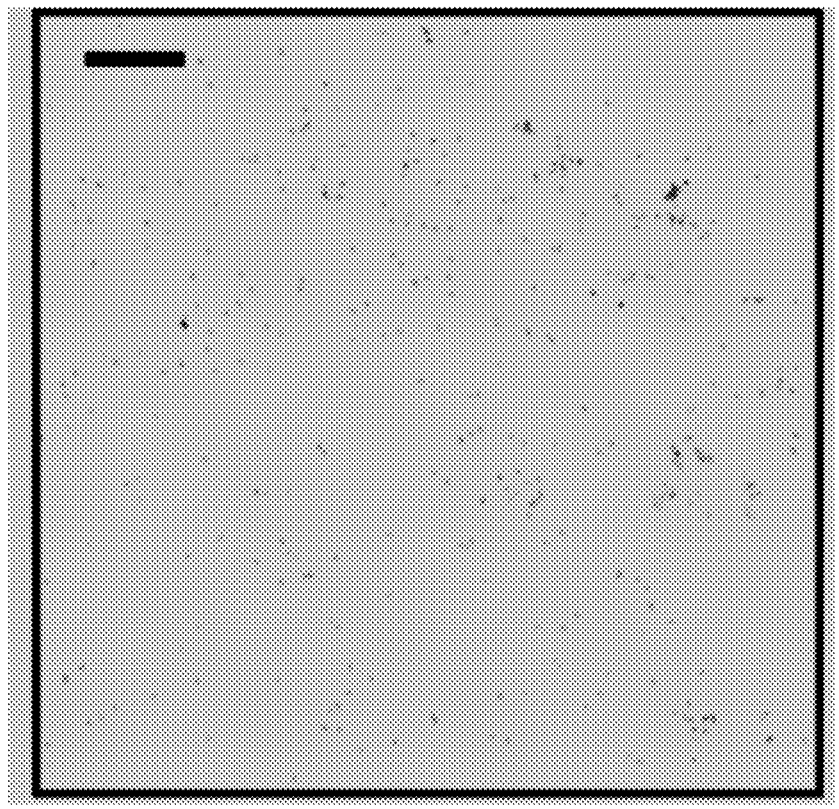
FIG. 3A-3D: There is no co-localization between MOR and CXCR4.
Figure 3B:
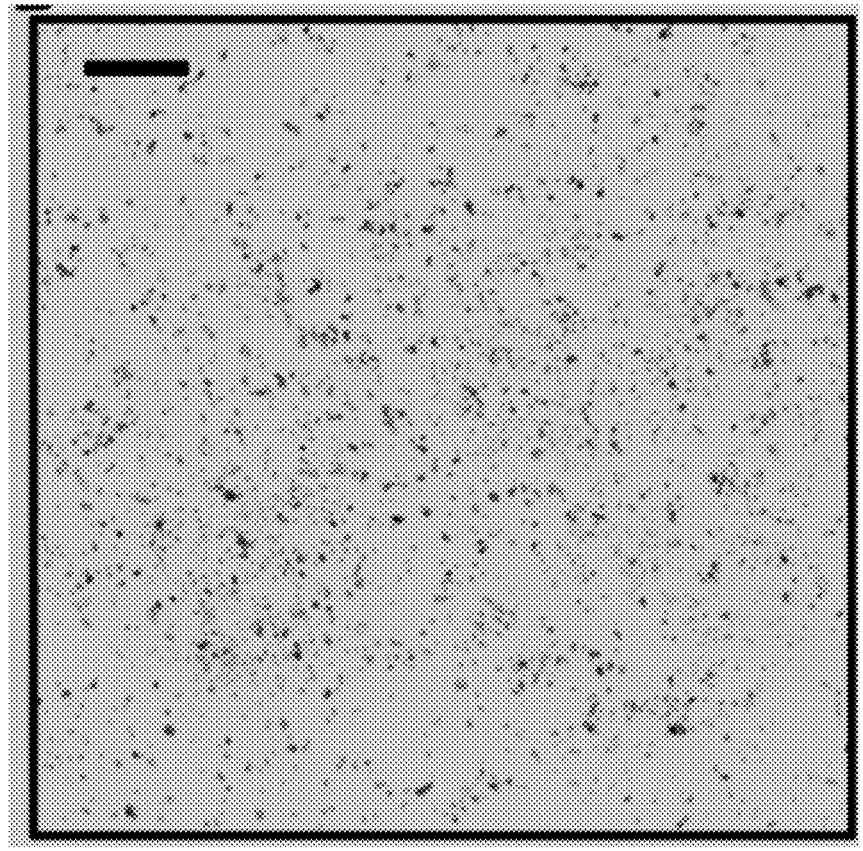
Figure 3C:
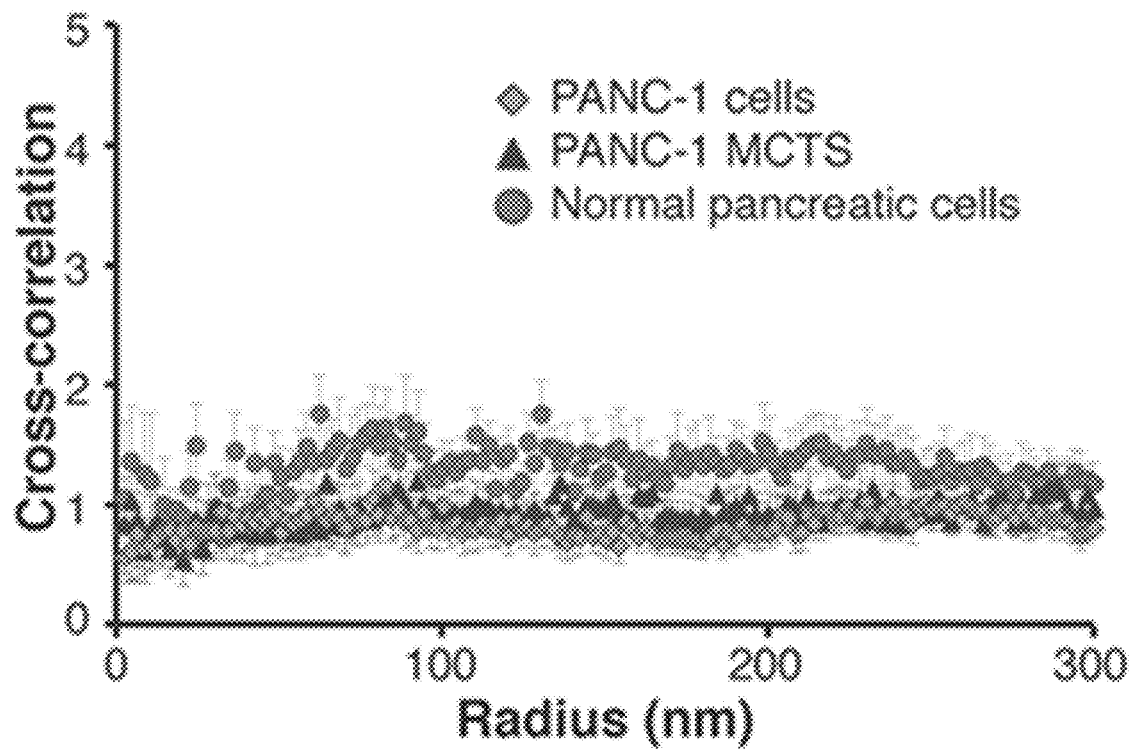
Figure 3D:
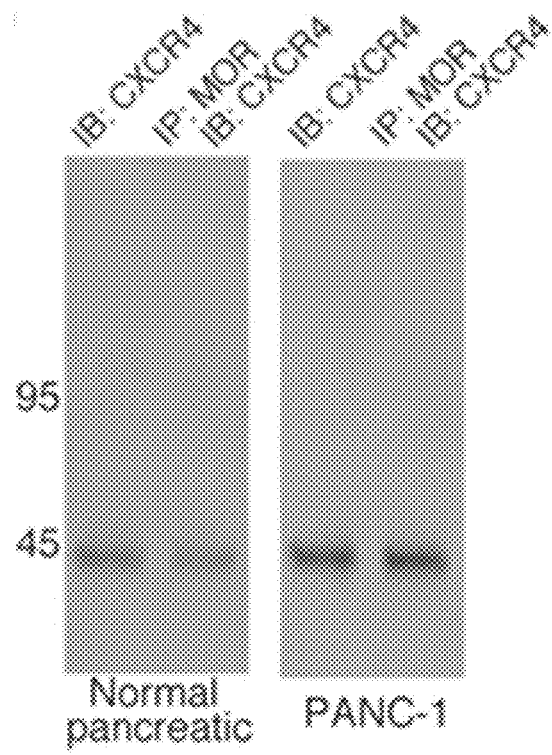
Figure 4A:
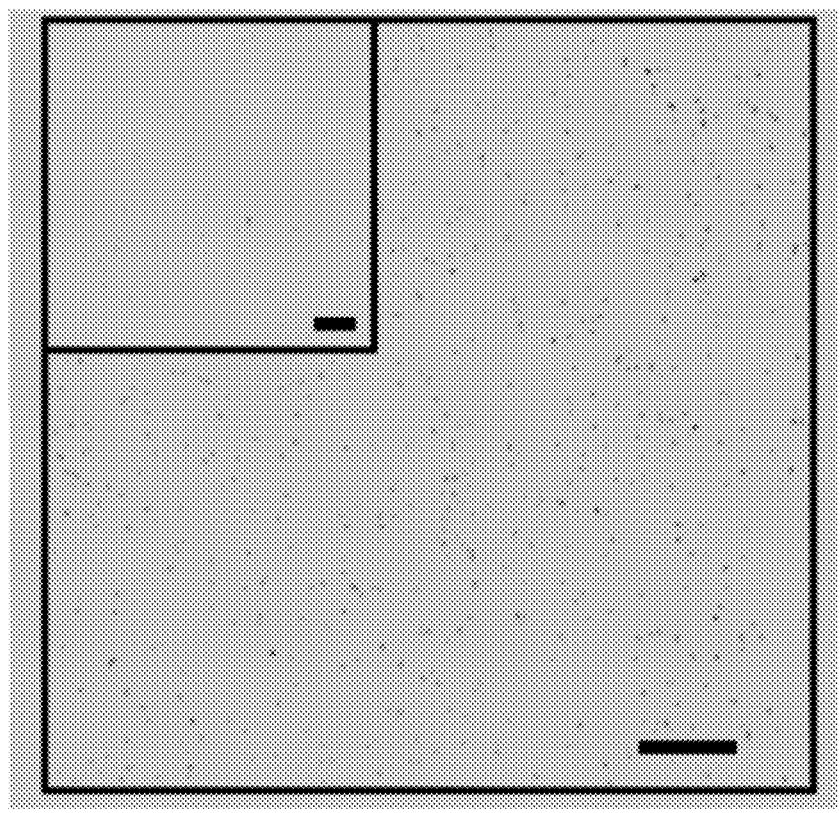
FIG. 4A-4C: Co-localization of MOR and SSTR2 in patient tissues.
Figure 4B:
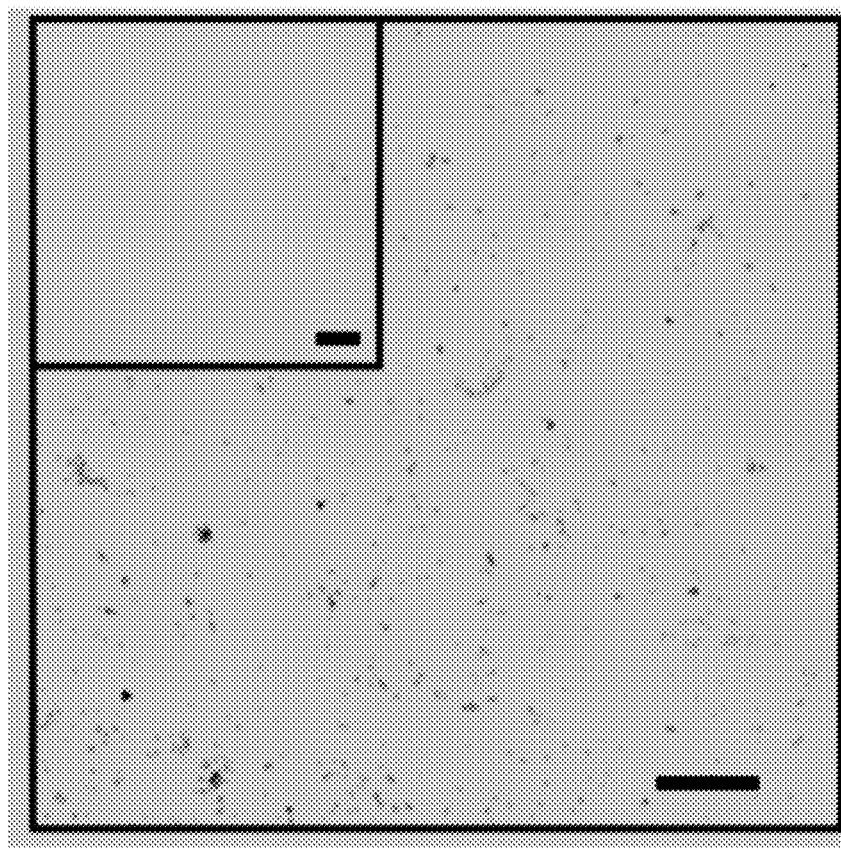
Figure 4C:
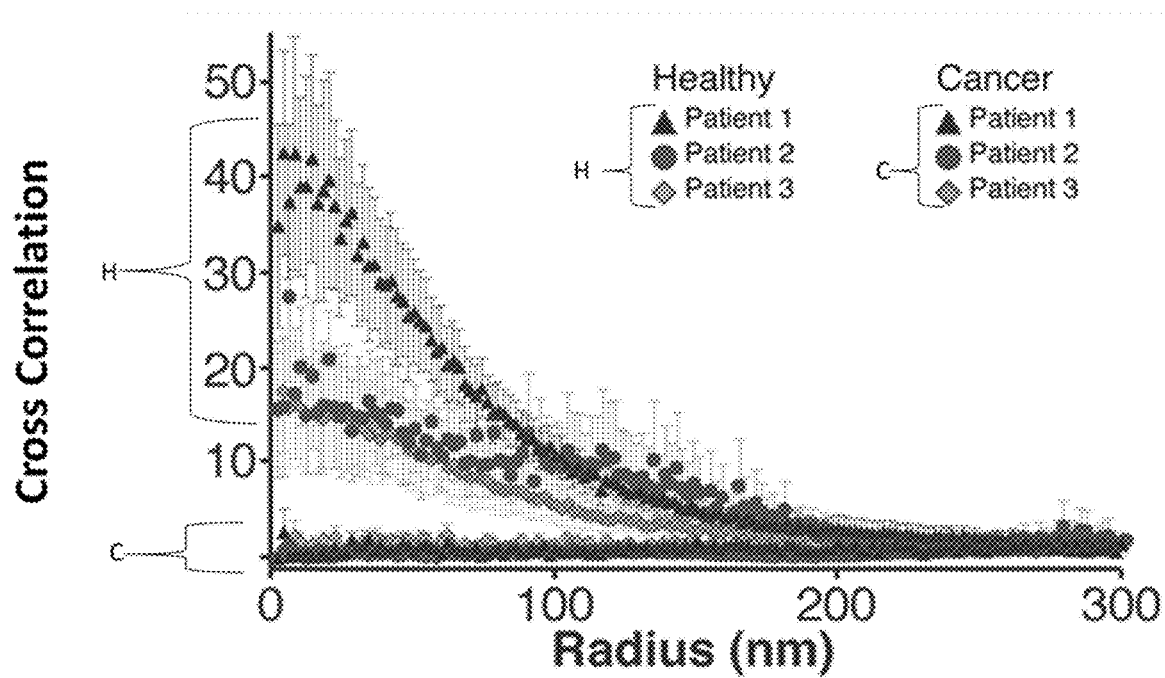
Figure 9B:
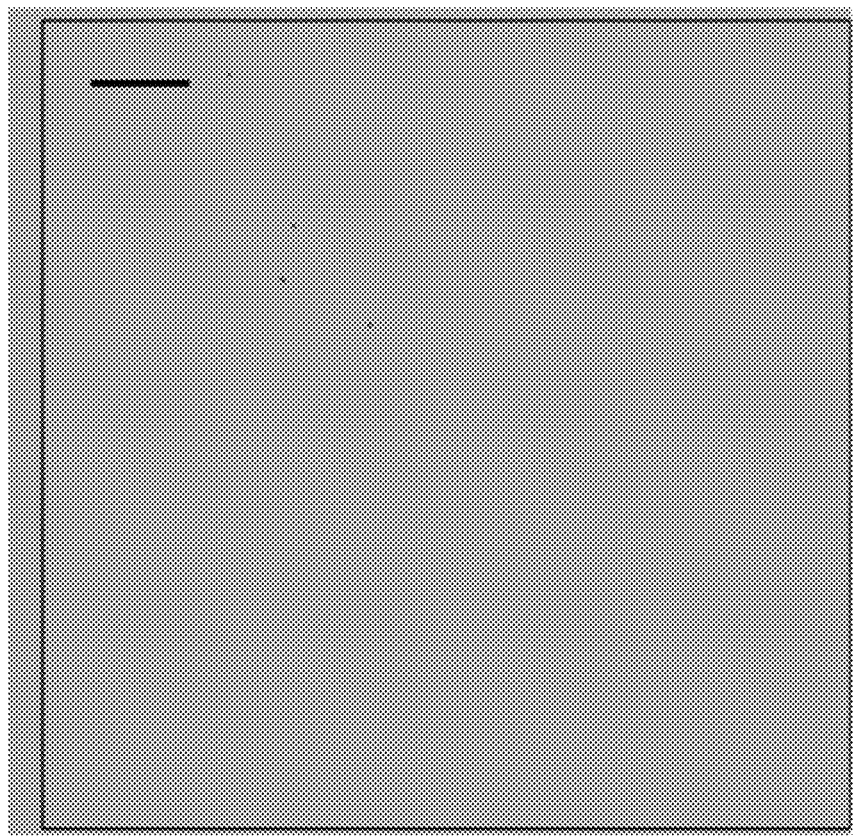
Figure 9C:
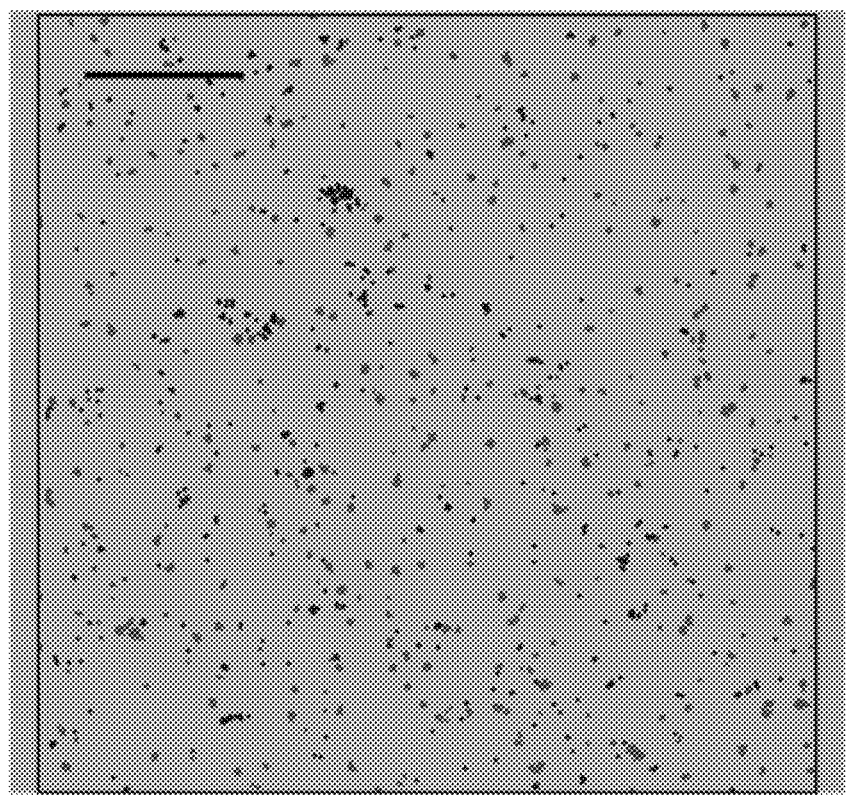
Figure 9D:
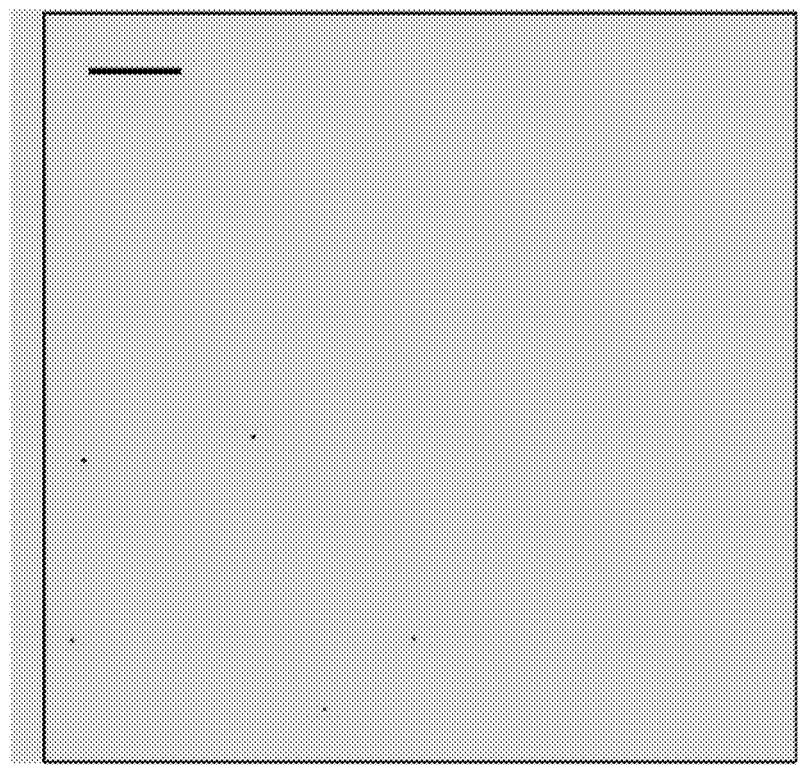
Figure 10A:
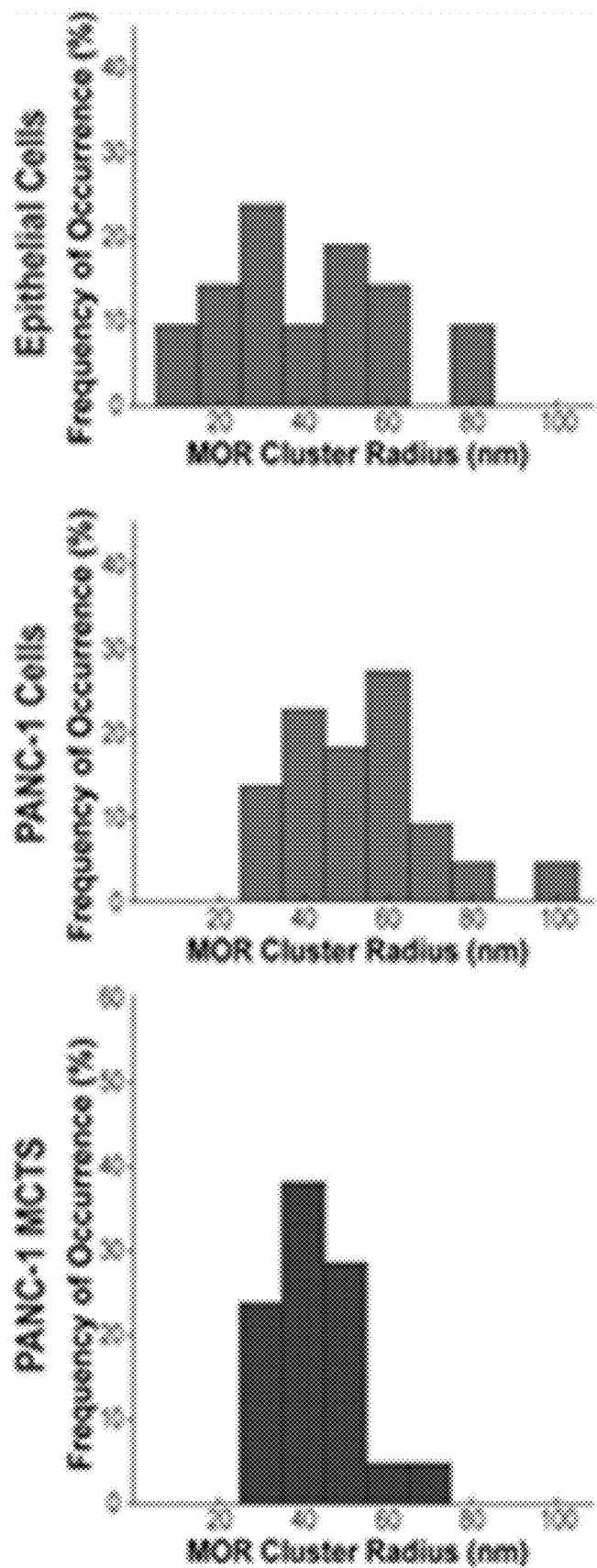
FIG. 10A-10G: GPCR cluster sizes and circularity obtained using SR-Tesseler (Levet et al., 2015).
Figure 10B:
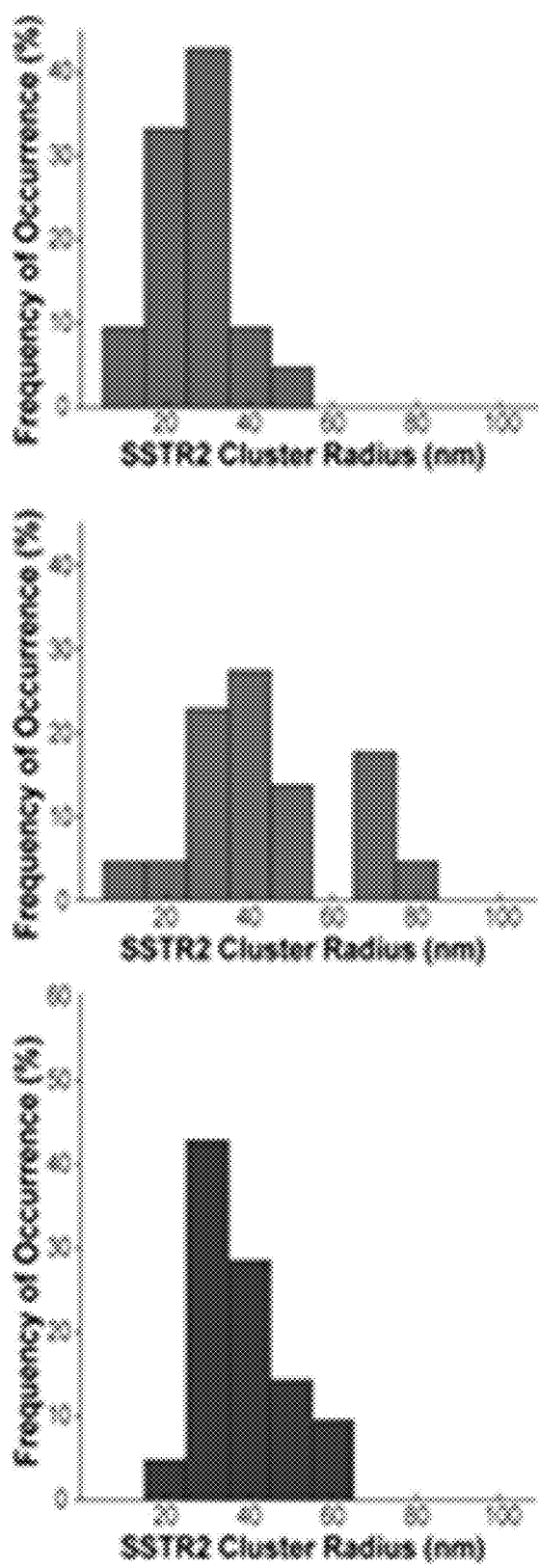
Figure 10C:
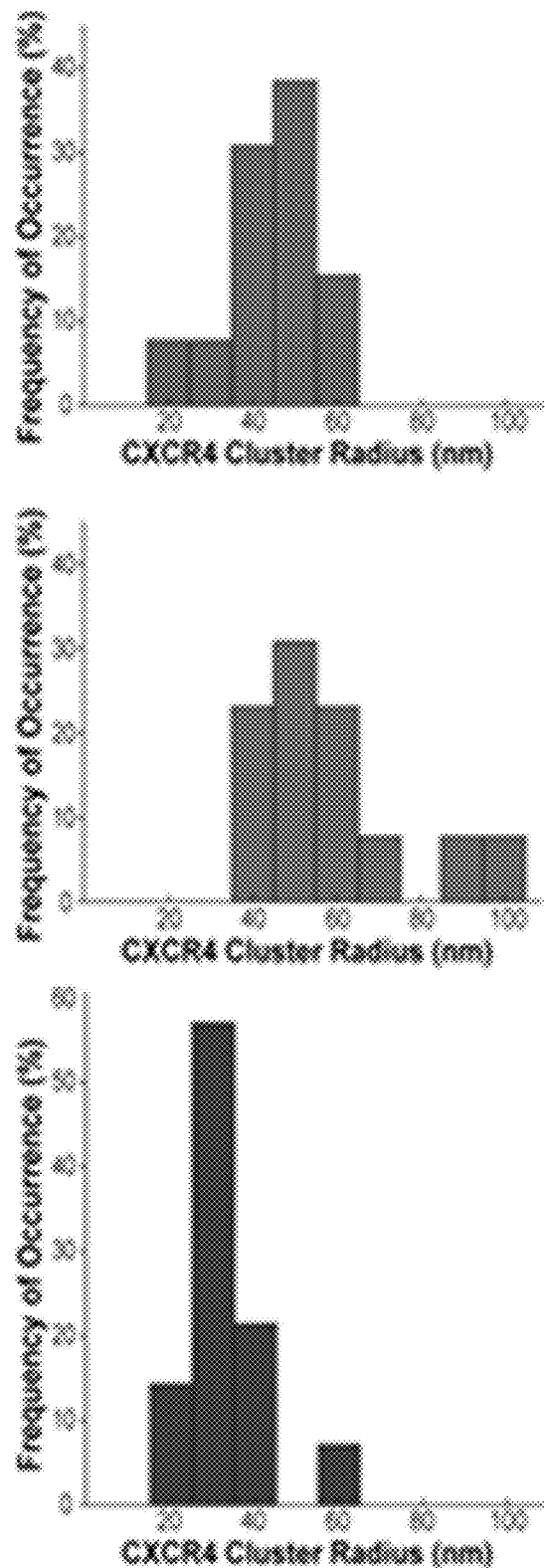
Figure 10D:
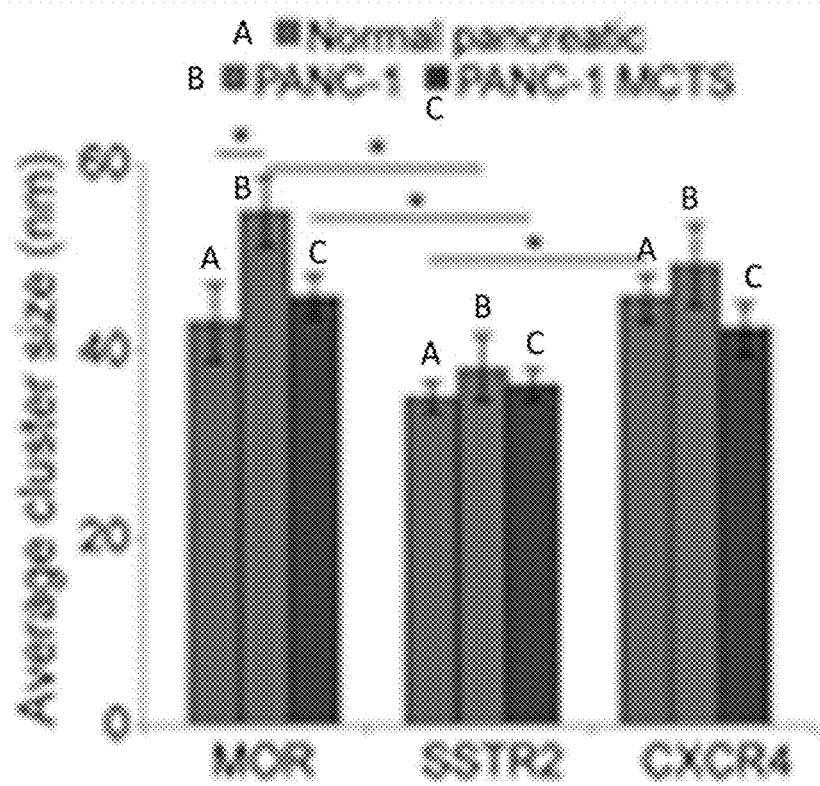
Figure 10D:
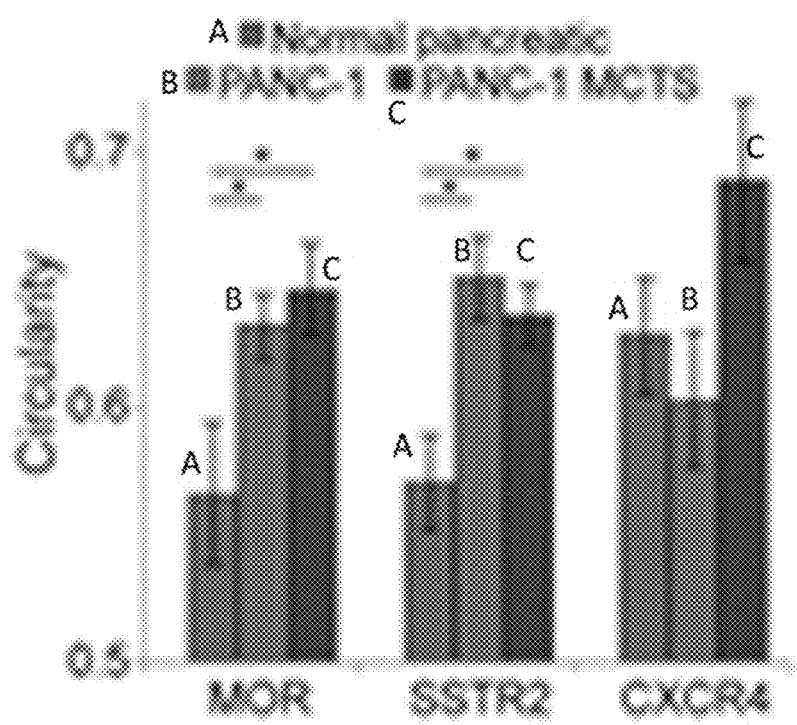
Figure 10E:
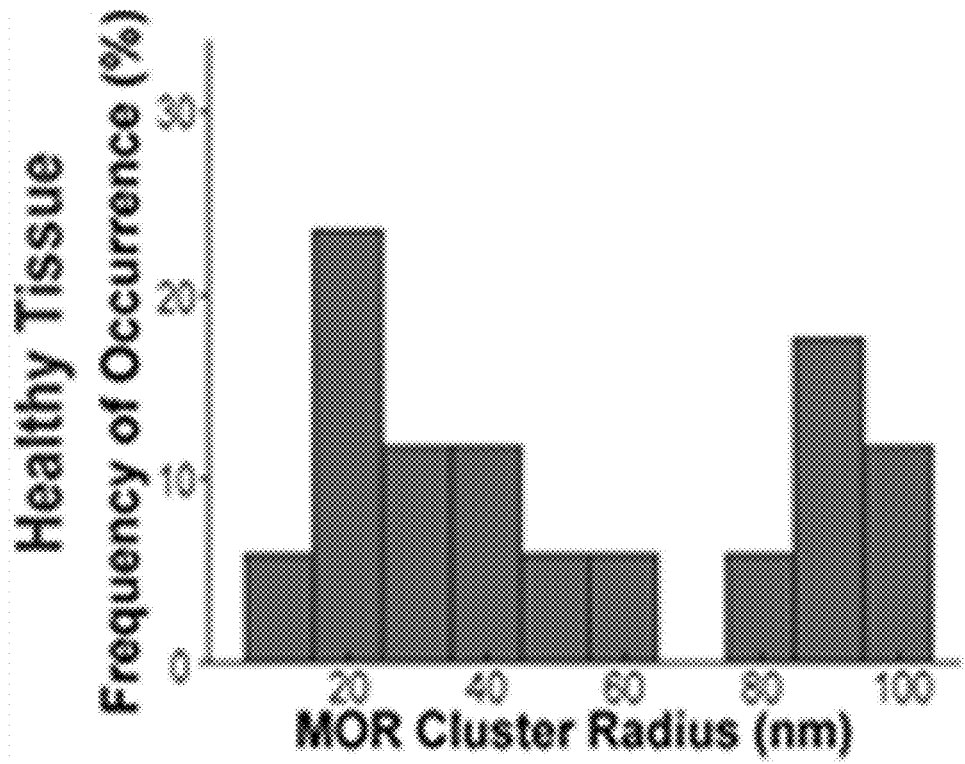
Figure 10E:
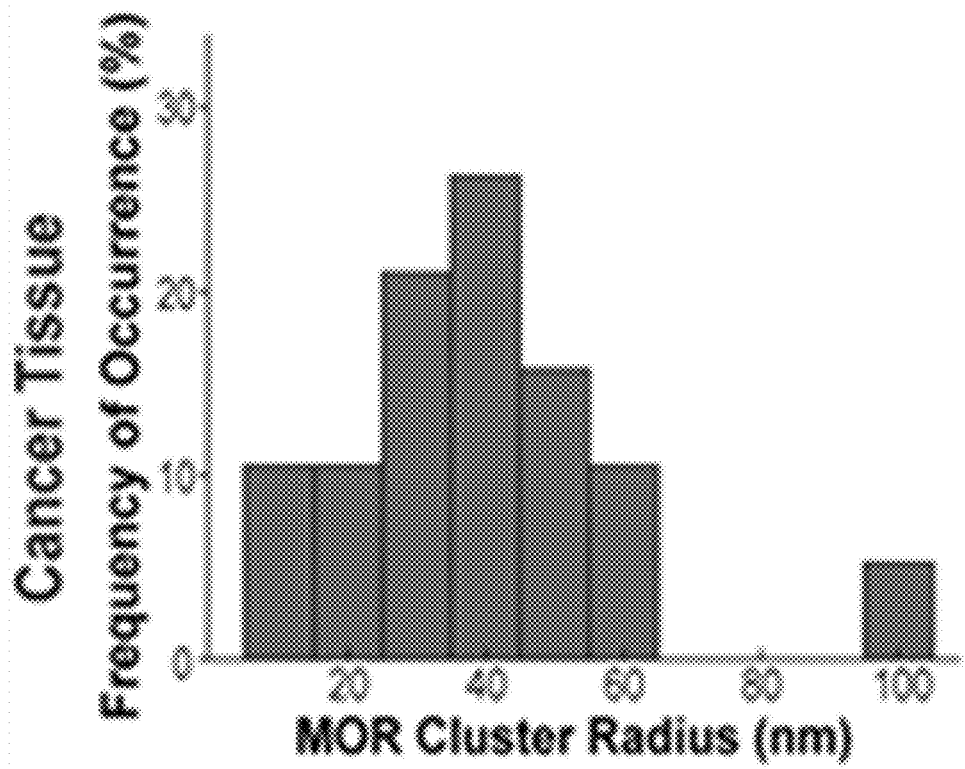
Figure 10F:
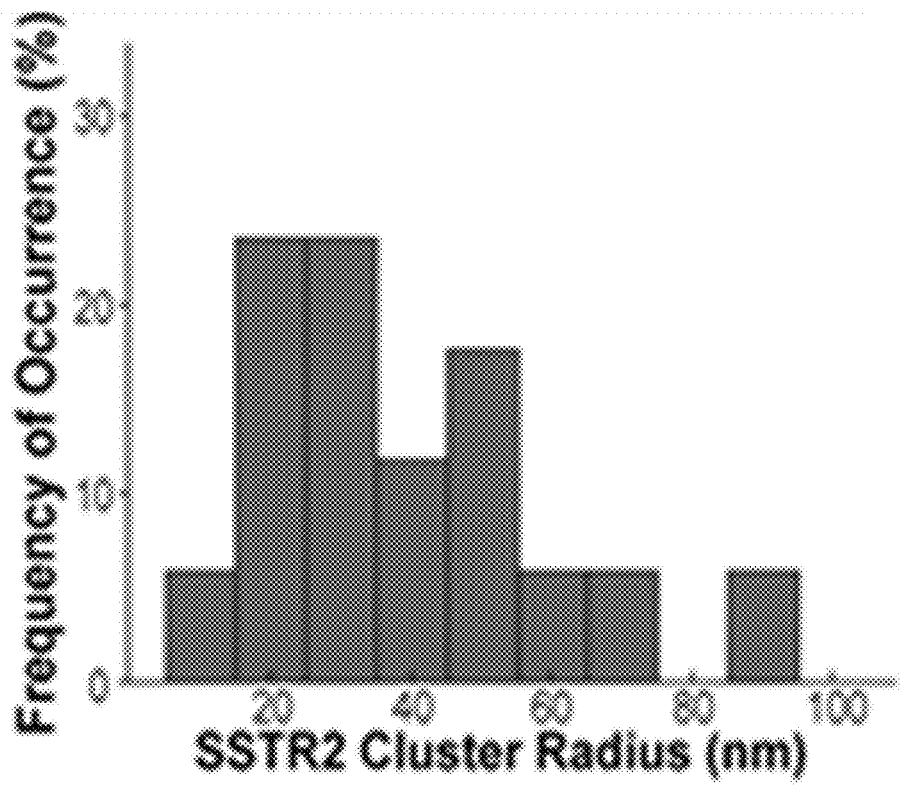
Figure 10F:
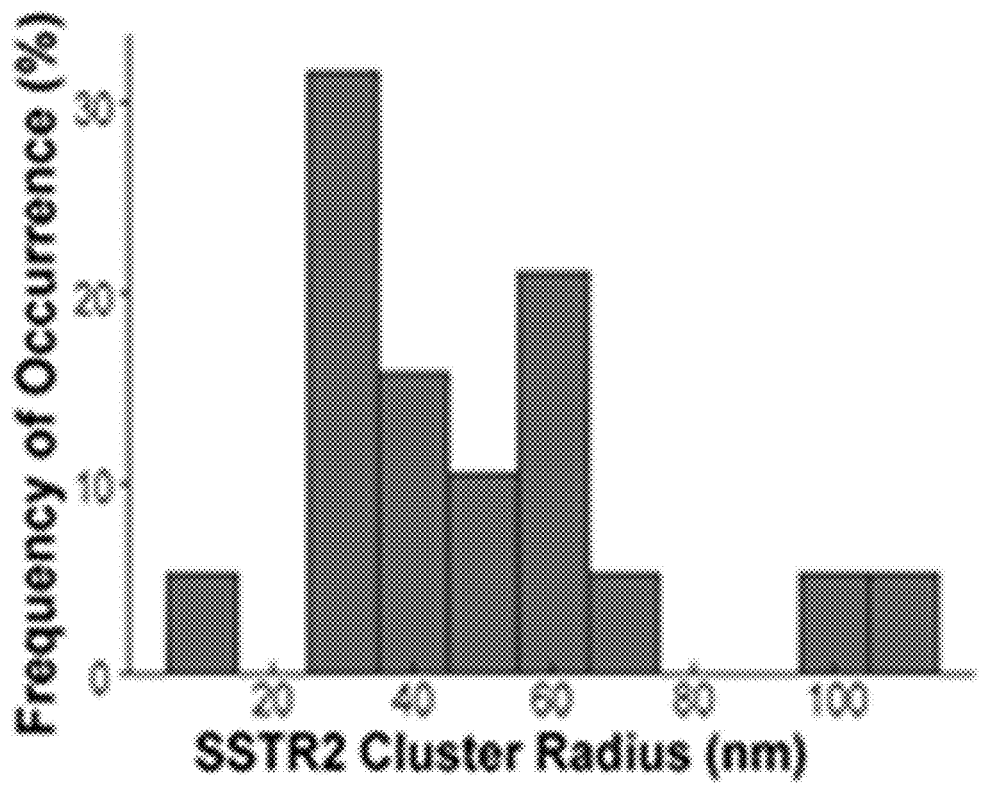
Figure 10G:
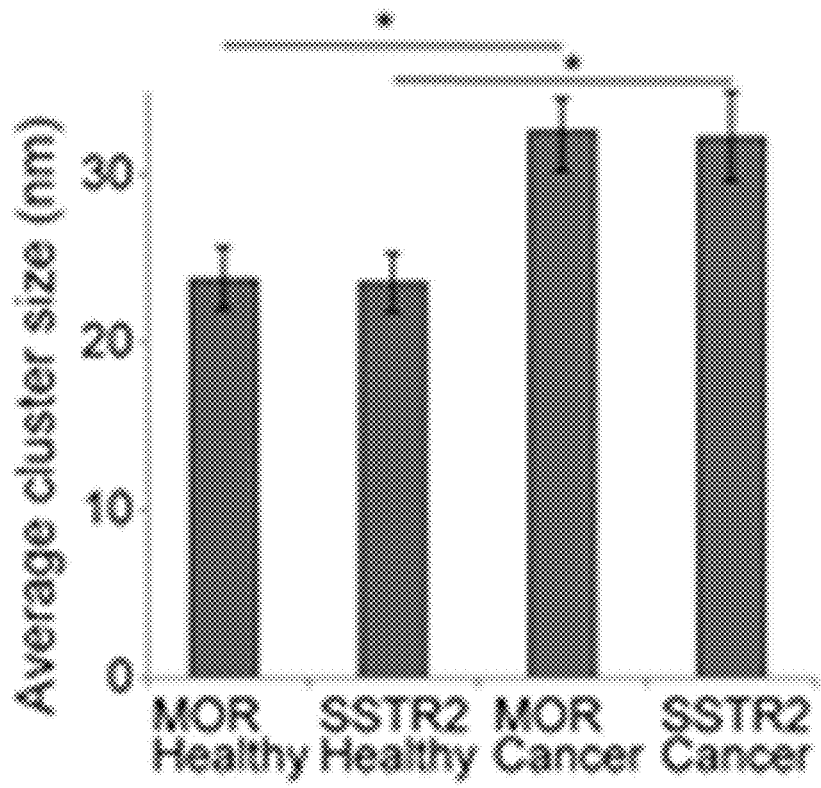
Figure 10G:
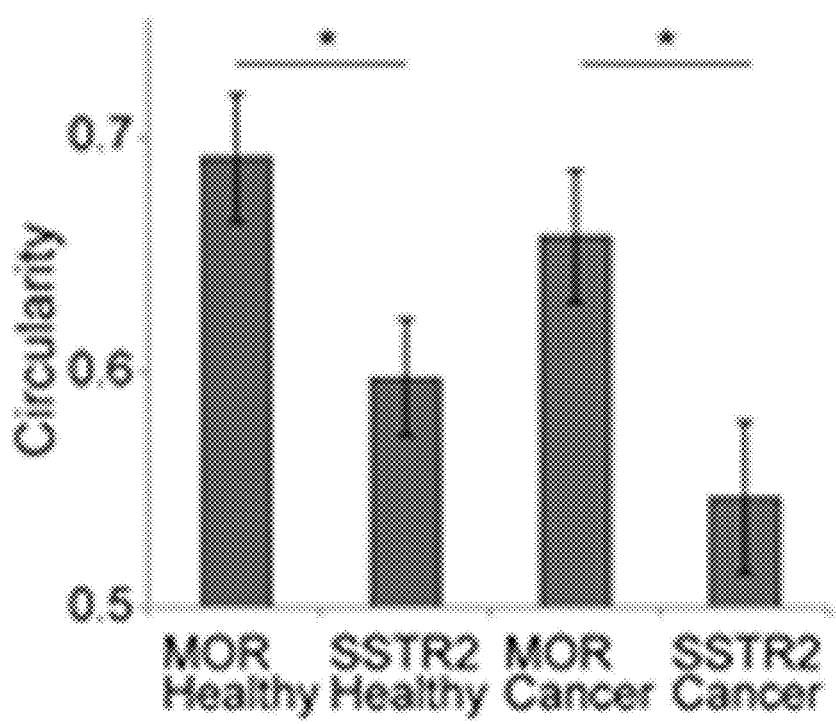
Figure 13:
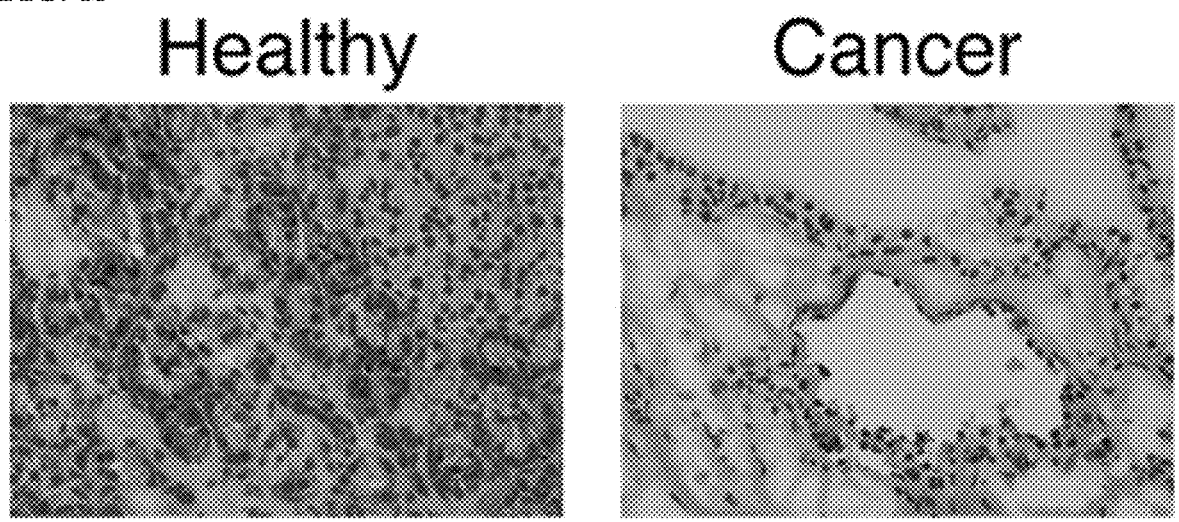
FIG. 13: Representative H&E staining of patient samples (matching healthy and cancer tissue) used for imaging. Experiments were performed at the City of Hope Pathology Core. Magnification, 200×.
Figure 14A:
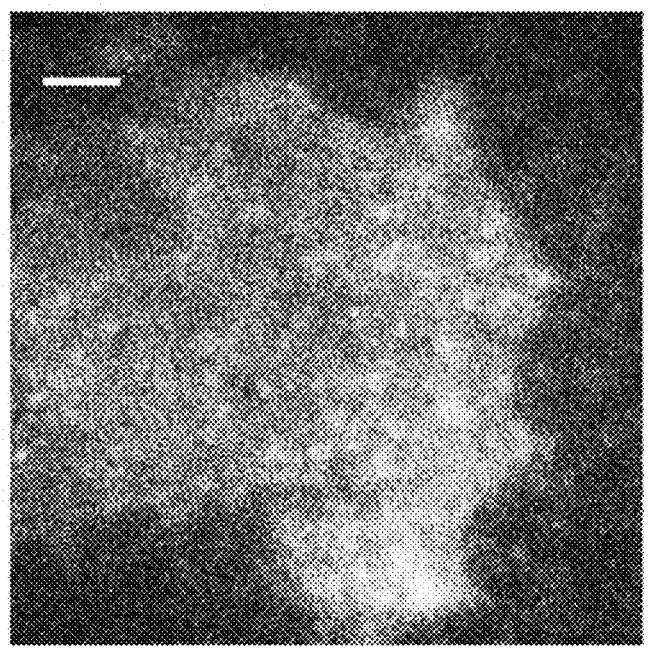
FIG. 14A-14B: Keratin 8 and 18 labels epithelial cells and tissues.
Figure 14B:
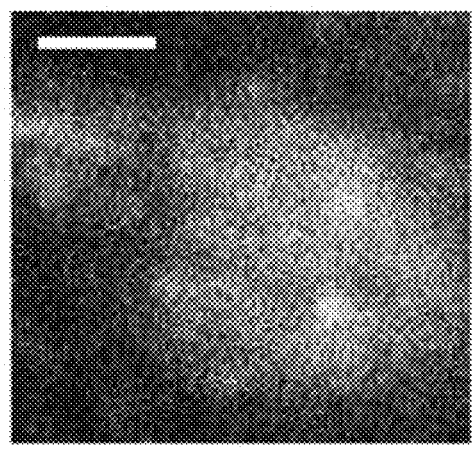
Figure 14B:
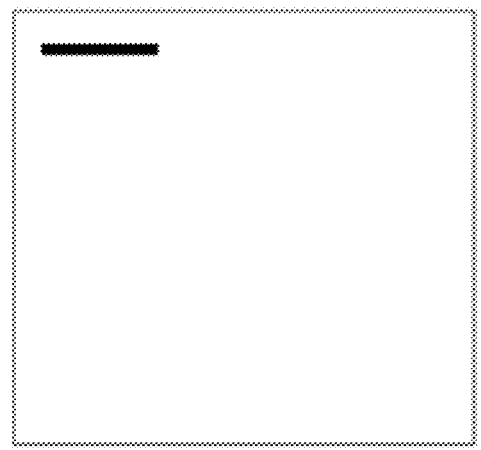

According to reports, CXCR4 is expressed at high levels in PDAC (Billadeau et al., 2006). Consistently, dSTORM revealed a significantly higher surface density of CXCR4 in PANC-1 cells compared to normal pancreatic cells. Interestingly, quantitative data suggests that CXCR4 makes relatively uniform clusters with a radius of approximately 45 nm in both cell lines (FIG. 10). Co-localization of CXCR4 and MOR was next evaluated by PC-dSTORM on the surface of normal pancreatic cells, PANC-1 cells, and PANC-1 MCTS (FIG. 3A, FIG. 3B, and FIG. 9C, respectively). As with MOR and SSTR2 (FIG. 4B), the imaging approach was validated in PANC-1 MCTS using blocking peptide controls to show that the antibodies were specific for MOR and CXCR4 (FIG. 4D). According to the dSTORM imaging results, the two GPCRs do not co-localize in any of the pancreatic environments. This was confirmed by quantitative correlation analyses (FIG. 3C): The correlation curve is approximately equal to 1 in all cases. Additionally, co-immunoprecipitation experiments (FIG. 3D) suggest no association between receptors in both normal pancreatic cells and PANC-1 cells. These findings imply that the density of individual GPCRs is not a sole factor in determining their association.

dSTORM Imaging Quantitatively Detects GPCR Association in Patient Tissue Samples dSTORM was used to assess co-localization between MOR and SSTR2 in patient tissue samples. Both healthy and malignant samples were obtained from three patients during surgical resection. Via H&E staining protocols, the samples were confirmed as being from either the primary PDAC tumor or negative surgical margins (representative images are shown in FIG. 13). For the super-resolution experiments, frozen sections of tissues were prepared, labeled, and imaged. Since PDAC tissue contains both epithelial cells and high levels of stroma (Kleeff et al., 2007), keratin 8 and 18 antibodies (specific for epithelial cells (Moll et al., 1982)) were used to discriminate between these tissue types. An Alexa Fluor 405 tagged antibody was used to detect the keratins and Alexa Fluor 488/647 tagged antibodies were used to detect MOR and SSTR2. In each region, fluorescence in the 405 channel was recorded after imaging in the 488/647 channels. Controls demonstrate that the keratin 8 and 18 antibody binds to epithelial PANC-1 cells and that no cross-talk between 405 and 488/647 channels was observed in tissues (FIG. 14). The distribution of MOR and SSTR2 was determined in representative healthy and cancerous samples (FIG. 4). Negligible signal was detected when blocking peptides were used as controls in tissue samples (inset). Applicants analyzed multiple sections/regions from cancer tissues and healthy tissues of three patients. Tessellation results (FIG. 10E-G) suggest that both MOR and SSTR2 have significantly higher average cluster radii in cancer compared to healthy tissues. Additionally, in both cancer and healthy tissues, MOR formed more circular clusters on average compared to SSTR2 clusters. Importantly, significant overlap between receptors is evident only in cancer samples. Applicants performed PC-dSTORM analysis and the cross-correlation curves are given in FIG. 4C. Results suggest that MOR and SSTR2 co-localize in cancer tissue, where the extent of cross-correlation was patient dependent, but not in healthy margins.

Figure 15A:
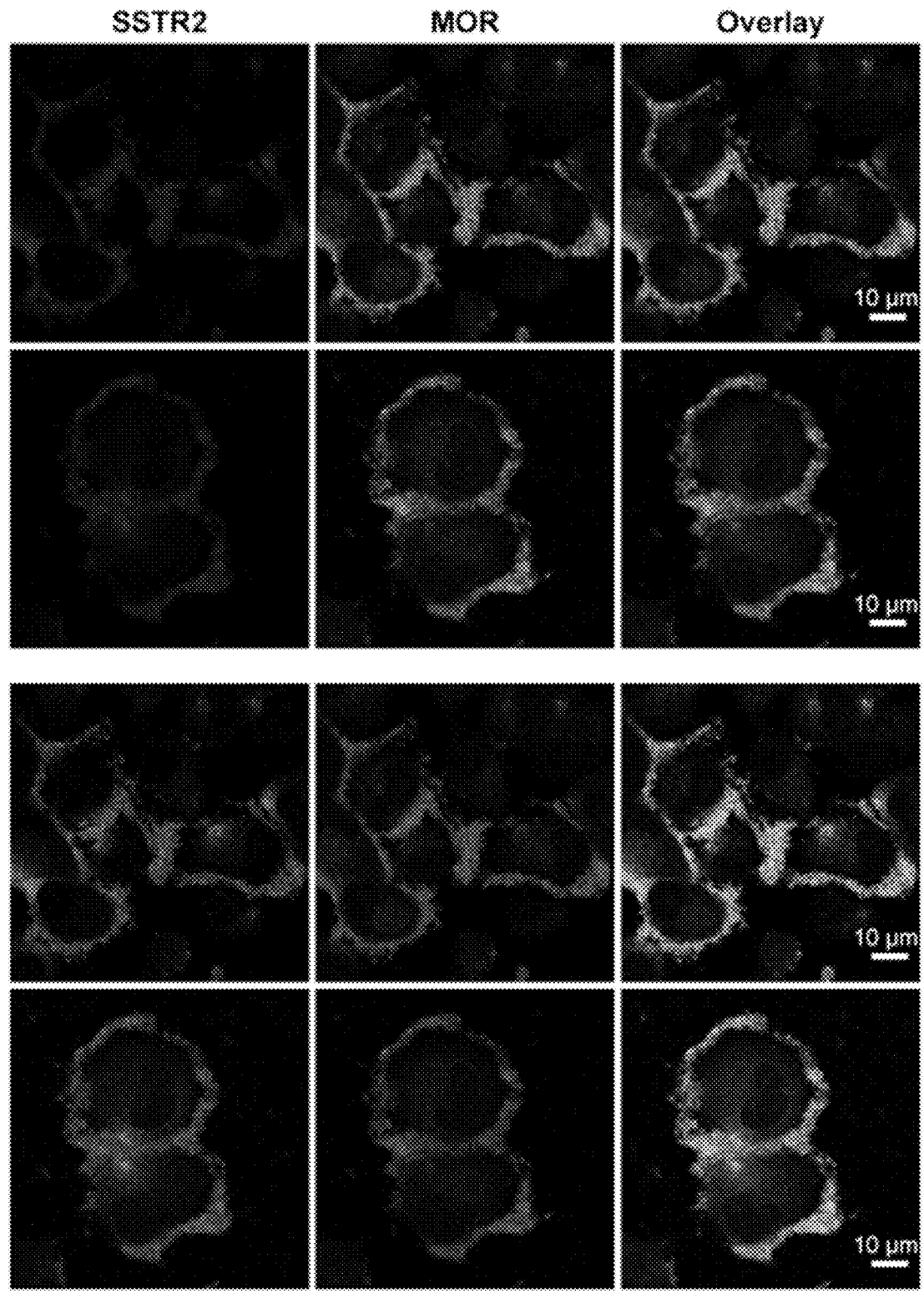
FIG. 15A-15B: Confocal images of MOR and SSTR2 in PANC-1 cells in steady state and upon co-activation with agonists.
Figure 15B:
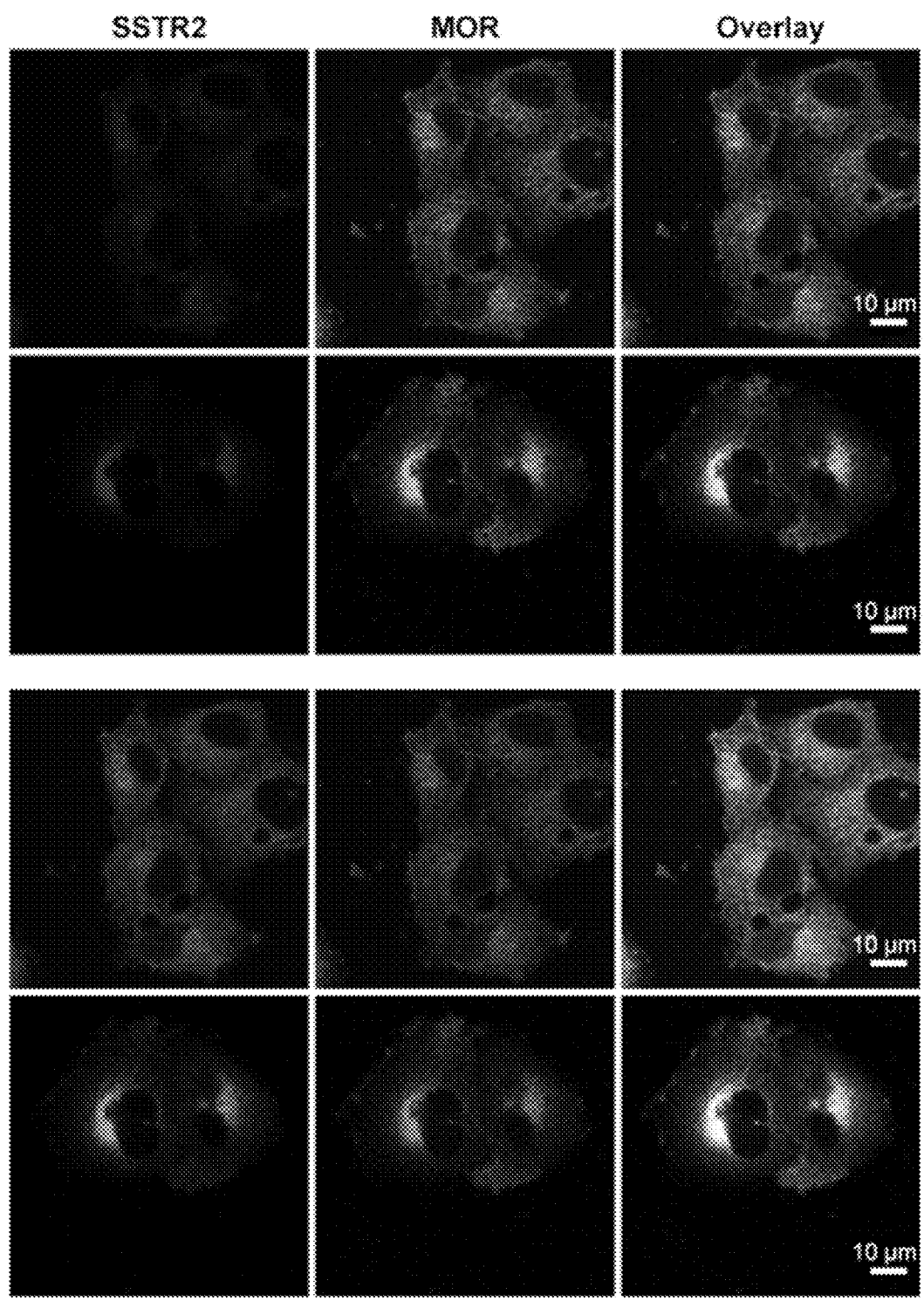
Figure 16A:
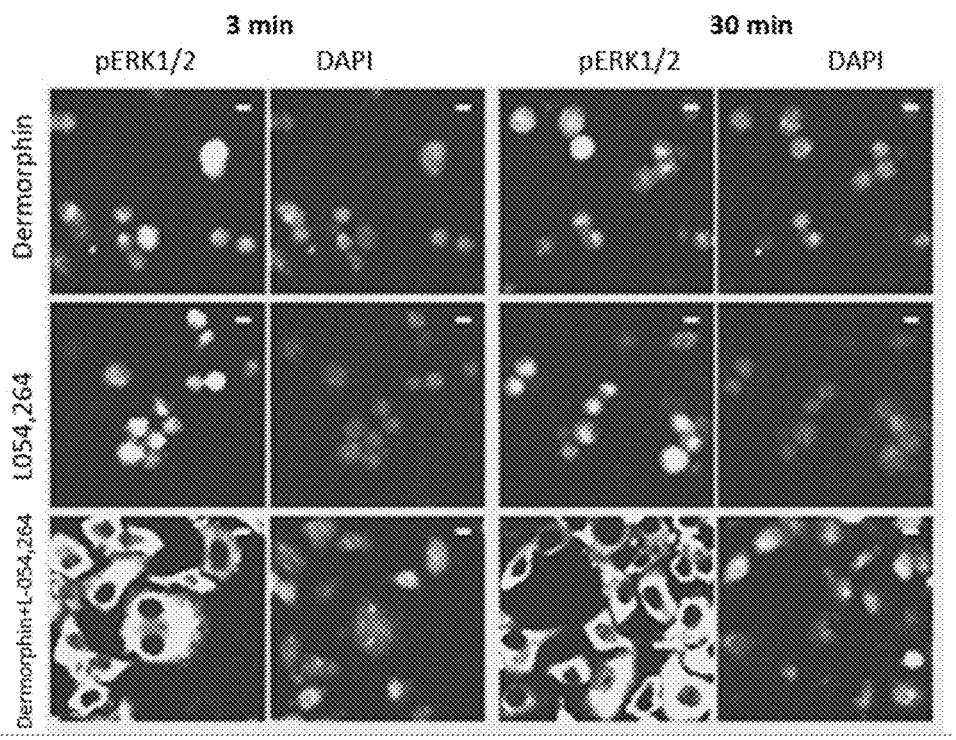
FIG. 16A-16F: Localization of pERK1/2 upon agonist treatment. Confocal imaging was used to determine pERK1/2 localization in cells upon various agonist treatments for the indicated periods of time. pERK1/2 was detected using a selective primary antibody with a labeled secondary antibody while the nucleus was detected with DAPI (two channels are shown separately); scale bars, 10 µm.
Figure 16B:
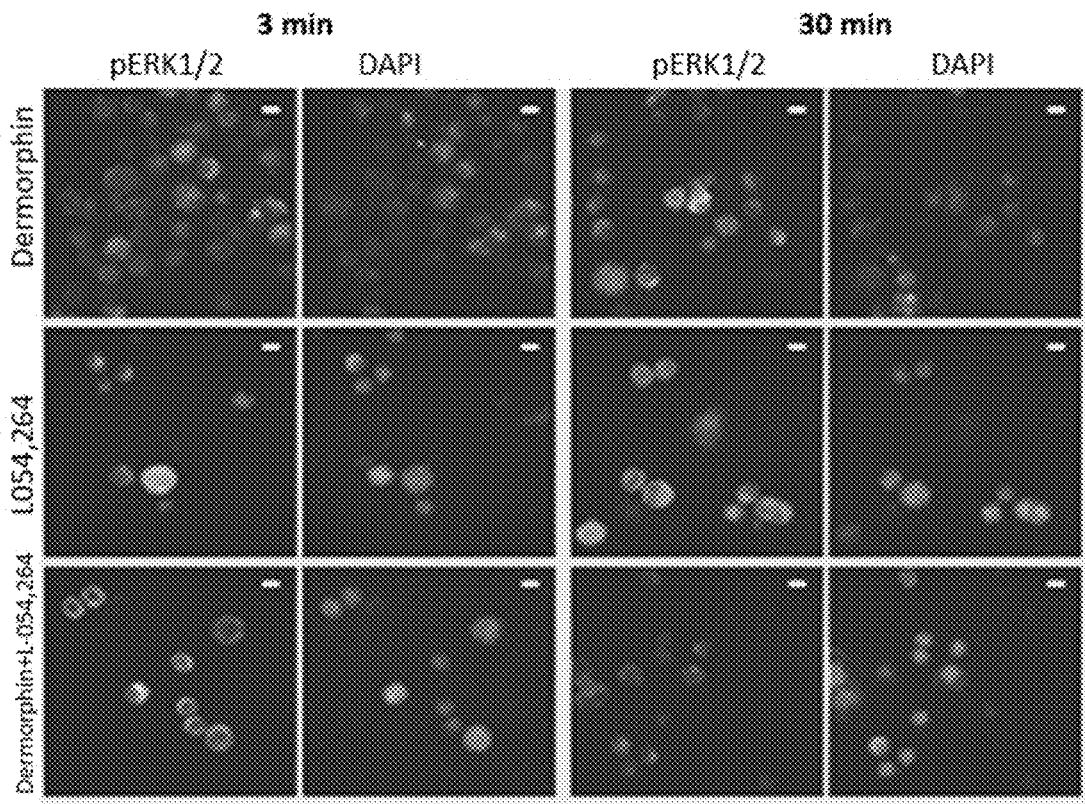
Figure 16C:
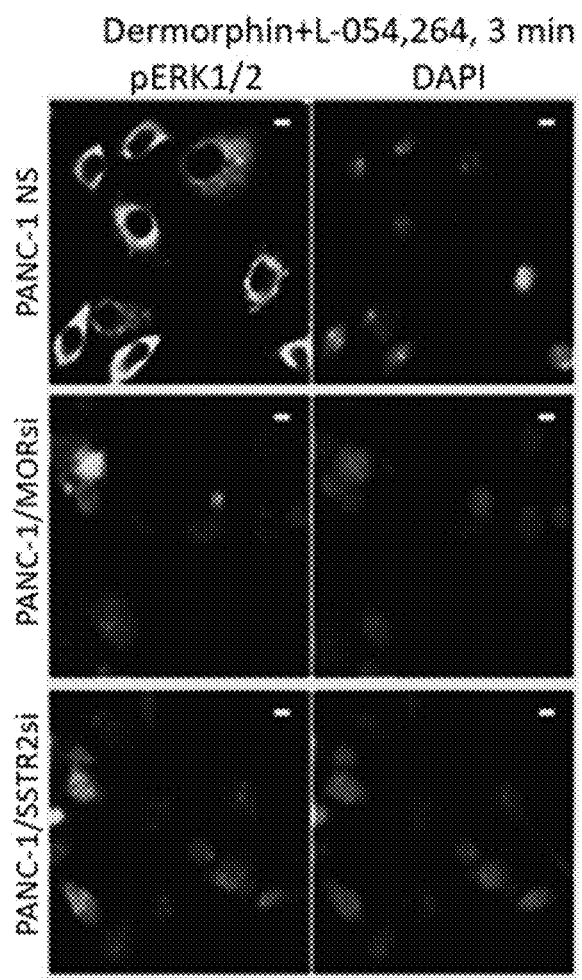
Figure 16D:
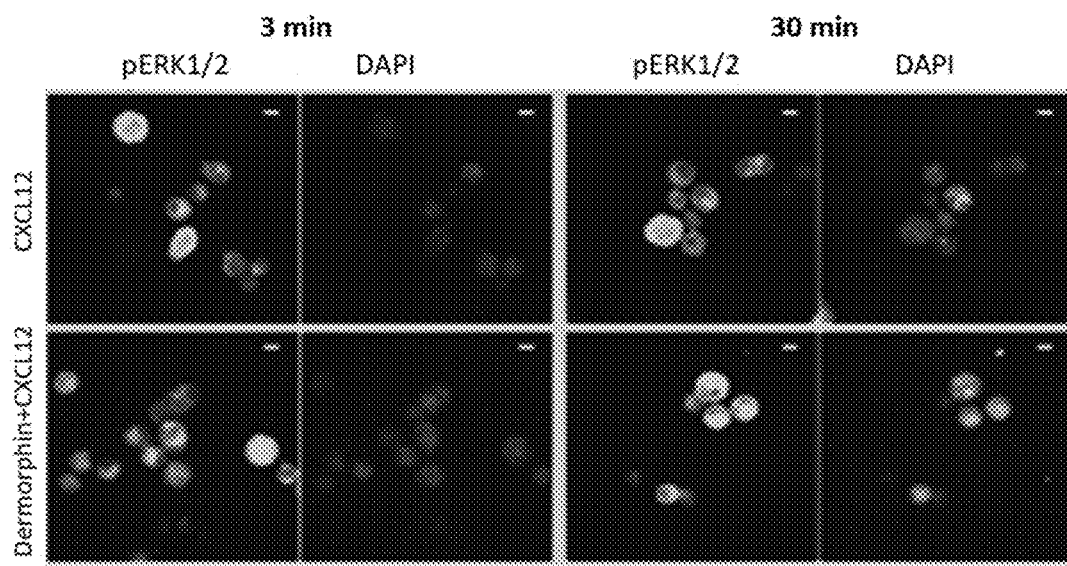
Figure 16E:
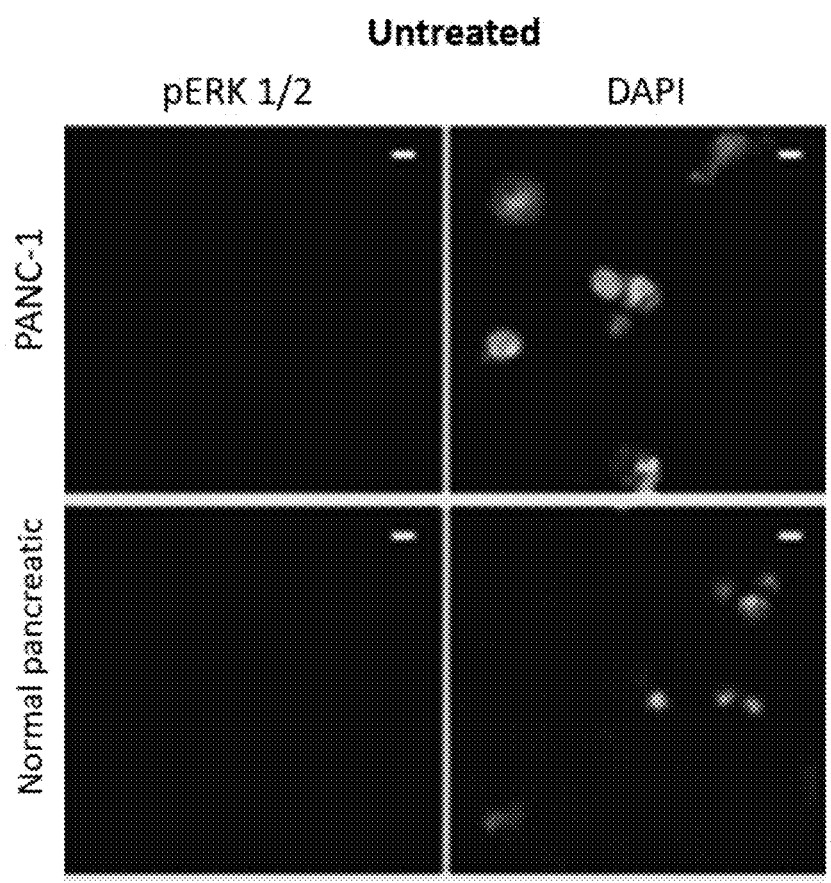
Figure 16F:
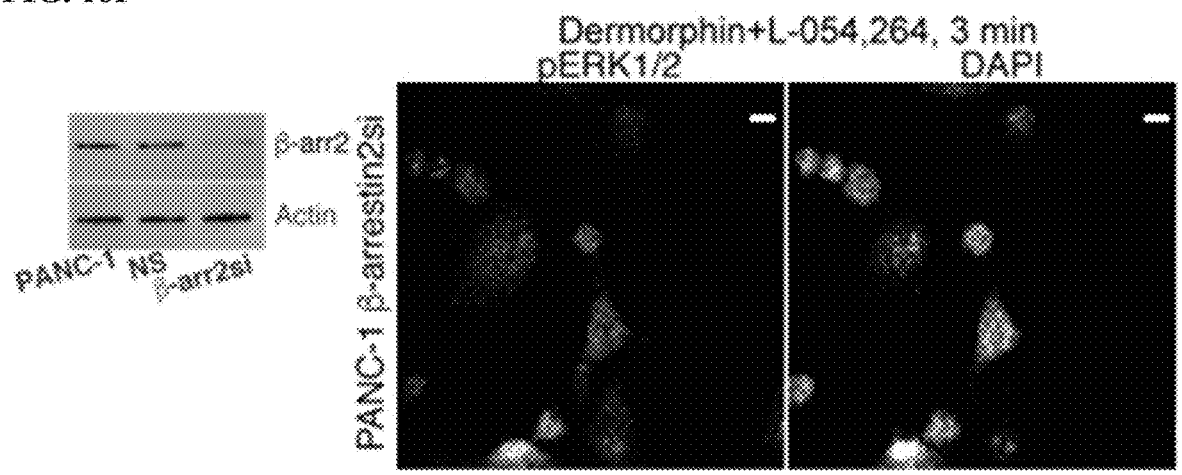

Activation of MOR and SSTR2 with Selective Agonists Leads to Receptor Internalization Given that in pancreatic cancer environments MOR and SSTR2 co-localize on the membrane, Applicants next examined the impact of selective agonists on the cellular localization of these receptors with confocal microscopy. Applicants used a specific MOR agonist, dermorphin (Melchiorri and Negri, 1996) and a specific SSTR2 agonist, L-054,264 (Kailey et al., 2012). These data demonstrate largely membrane localization of MOR and SSTR2 in steady state as expected, and their subsequent internalization upon co-activation with selective agonists in PANC-1 cells (FIG. 15).

Figure 5A:
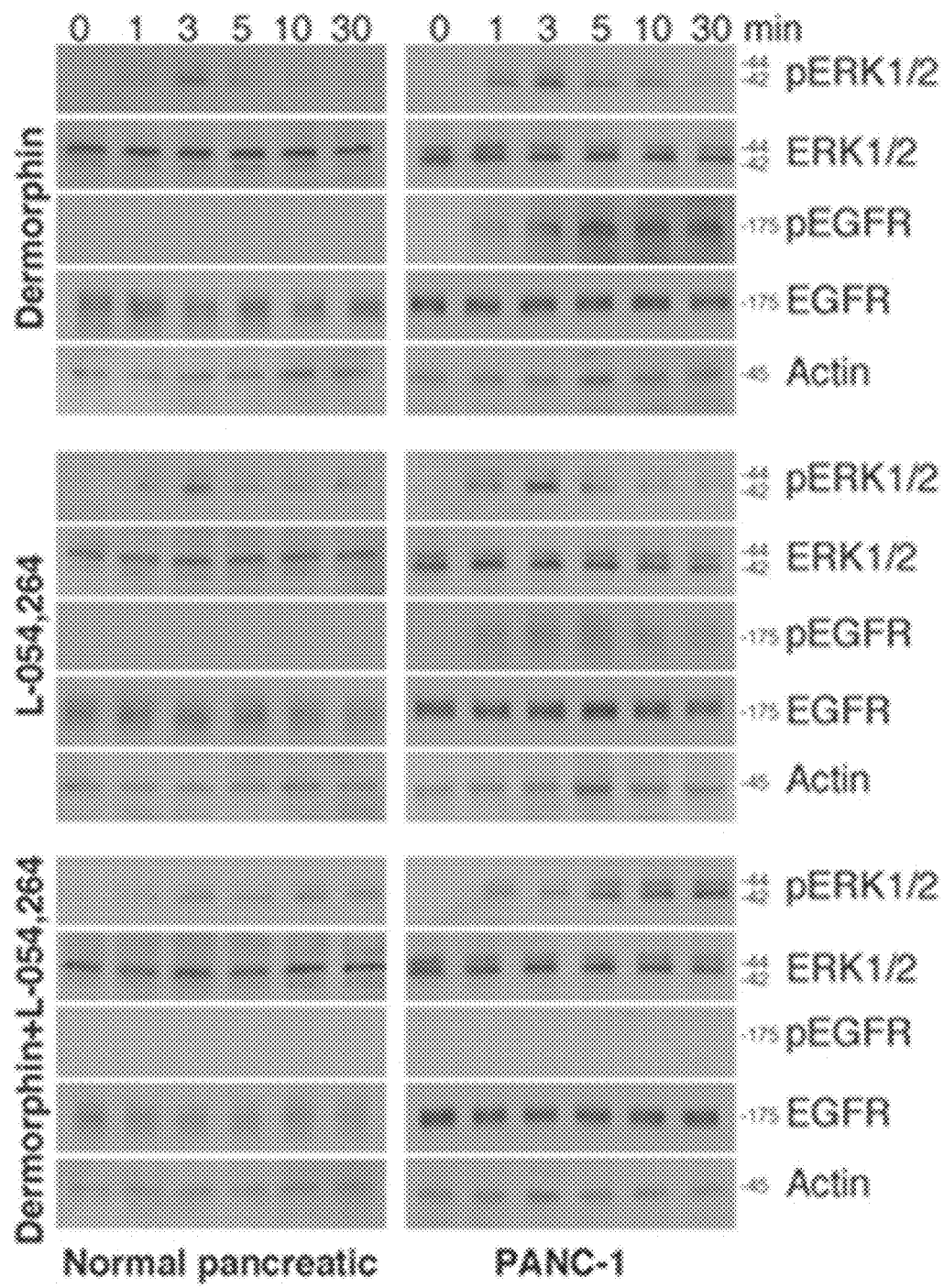
FIG. 5A-5E: Combined MOR and SSTR2 agonists treatment leads to a distinct signaling pathway in PANC-1 cells.
Figure 5B:
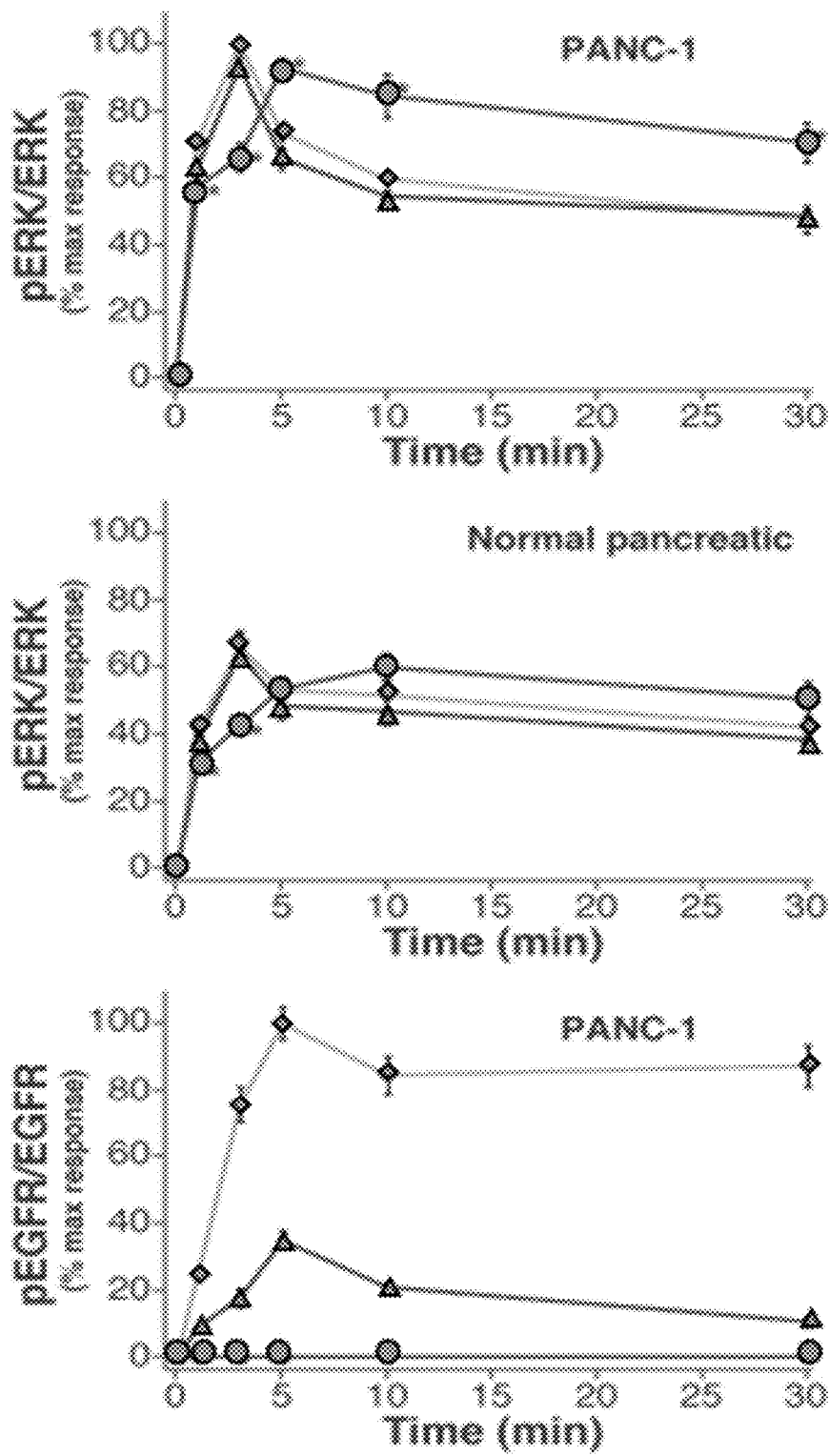

Simultaneous Activation of MOR and SSTR2 Influences Both EGFR and ERK1/2 Phosphorylation in PANC-1 Cells To examine signaling pathways upon activation of MOR and/or SSTR2, Applicants performed downstream phenotypic assays measuring extracellular signal-regulated kinase (ERK1/2) and epidermal growth factor receptor 1 (EGFR) phosphorylation. While their signaling pathways are complex, GPCR activation often converges at ERK1/2; which is critical for cellular proliferation, differentiation, and survival (Marshall, 1995; Bonni et al., 1999). The pathways may additionally involve activation of EGFR (Belcheva et al., 2001; Billadeau et al., 2006) which is often overexpressed in PDAC (Korc et al., 1992). To evaluate potential roles played by associated MOR and SSTR2 in PDAC, these two GPCRs were activated in both normal pancreatic cells and cancerous PANC-1 cells. Using a variety of ligands, the phosphorylation status of ERK1/2 and EGFR were examined. Via Western blot analysis, three treatments were evaluated: 1) a specific MOR agonist, dermorphin, 2) a specific SSTR2 agonist, L-054,264, and 3) a combination of these two agonists (FIG. 5A,B). In normal pancreatic cells, EGFR phosphorylation was not detected with any of these treatments. In PANC-1 cells, however, the MOR agonist dermorphin induced significant EGFR phosphorylation while SSTR2 agonist induced modest EGFR phosphorylation. Importantly, a combination of the two agonists did not induce EGFR phosphorylation in PANC-1 cells. This result is consistent with previous results in breast cancer cells (Kharmate et al., 2013). With regards to ERK1/2, all treatments produced transient phosphorylation of ERK1/2 in both normal and PANC-1 cells, albeit to different extents. Compared to levels observed in normal cells, higher levels of treatment-induced pERK1/2 were observed in PANC-1 cells. While single agonists produced similar kinetic profiles of ERK1/2 phosphorylation in both cell lines with maxima at 3 minutes, the combination of two agonists yielded slower and more sustained (post 3 min) pERK1/2 activation only in PANC-1 cells.

Figure 5C:
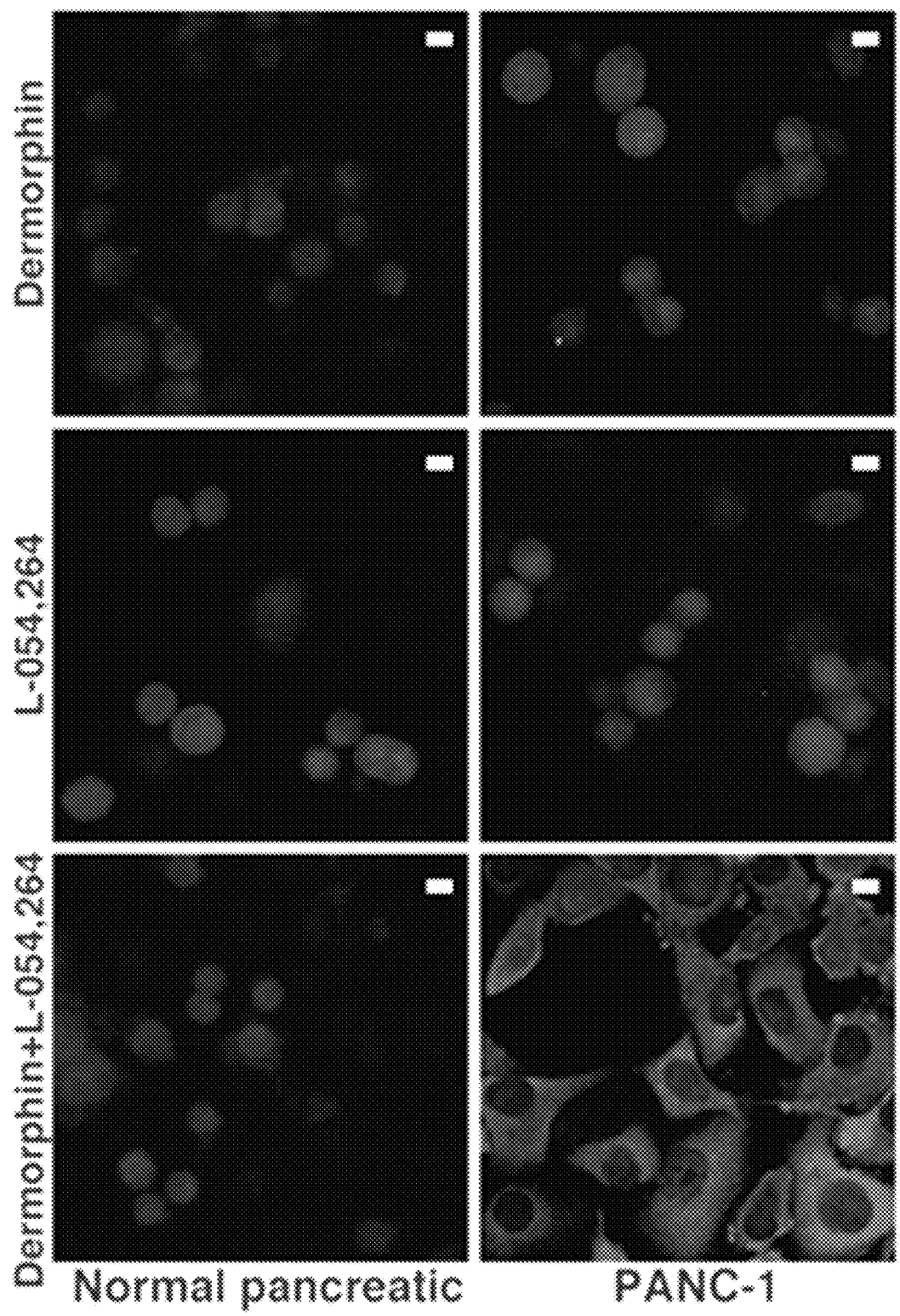
Figure 5D:
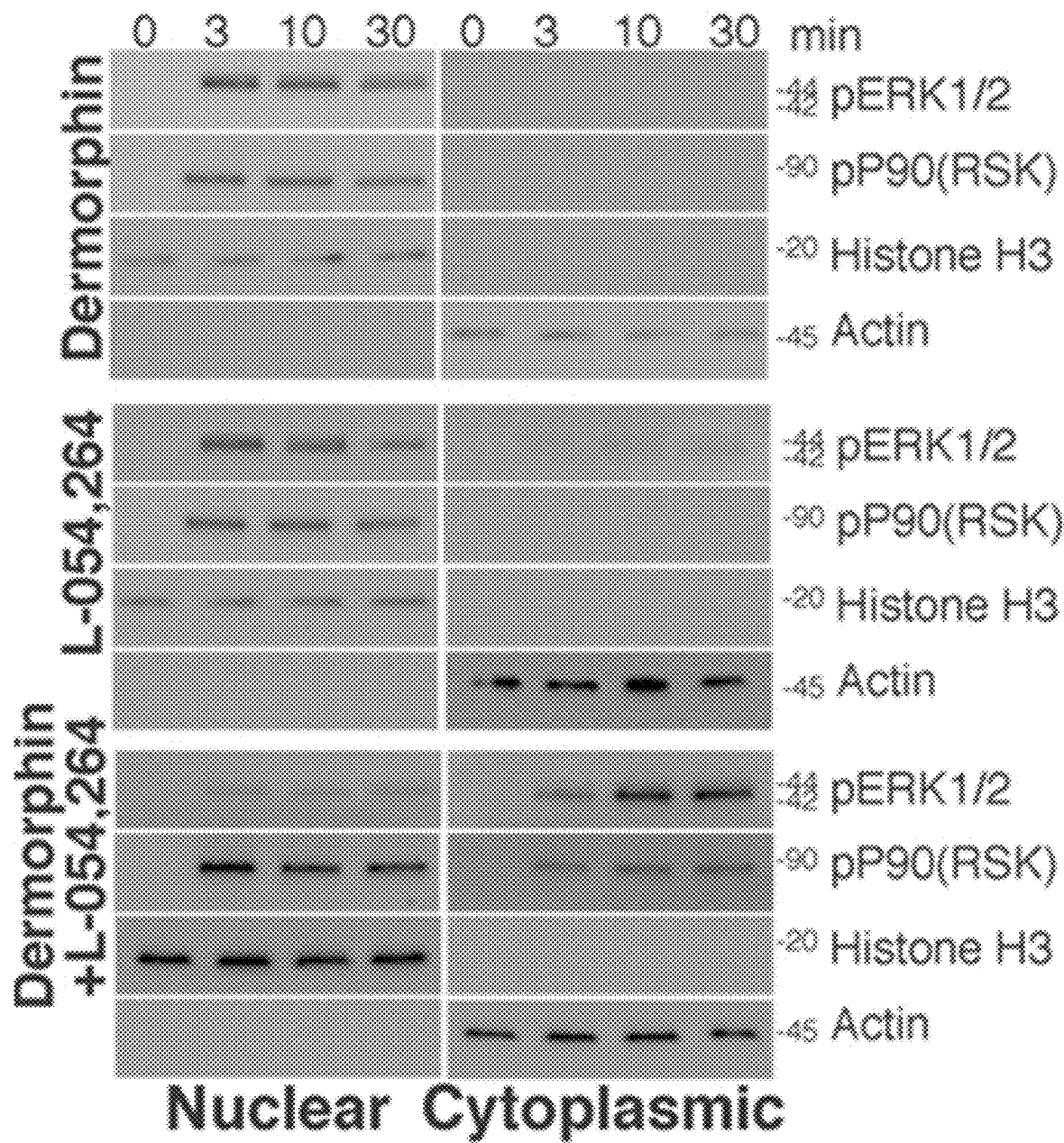

Simultaneous Activation of MOR and SSTR2 Influences the Localization of pERK1/2 and pRSK in PANC-1 Cells Using confocal imaging of cells, Applicants next investigated the effects of single and combined agonists on pERK1/2 localization (FIG. 5C and FIG. 16). For all treatments in normal pancreatic cells, low levels of pERK1/2 were detected in the nucleus. In PANC-1 cells with single agonists, high levels of pERK1/2 were detected, again in the nucleus. Interestingly, treating PANC-1 cells with the combined agonists produced high levels of pERK1/2 located mostly in the cytoplasm. To determine whether this result was a direct function of engaging MOR and SSTR2 simultaneously, the combined treatment was evaluated in PANC-1 knockdown cells. In both PANC-1/MORsi and PANC-1/SSTR2si, treating cells with the combination of agonists resulted in largely nuclear pERK1/2. In PANC-1 NS control cells, largely cytoplasmic pERK1/2 localization was restored (FIG. 16C). Applicants next generated PANC-1/β-arrestin2si cell line and confirmed the knockdown using Western blots (FIG. 16F). Importantly, in PANC-1/β-arrestin2si cells, treatment with the L-054,264/dermorphin combination resulted in largely nuclear pERK1/2 (FIG. 16F). To further confirm this differential pERK1/2 localization in PANC-1 cells, subcellular fractionation experiments were performed, and the purity of fractionation was confirmed using cytoplasmic and nuclear markers (FIG. 5D). Treating with a single agonist quickly led to mostly nuclear pERK1/2, whereas even after prolonged treatment (30 min) with the double agonist combination, mostly cytoplasmic pERK1/2 was observed (FIG. 4D). As a control, the localization of pERK1/2 was evaluated after activating MOR and CXCR4, which do not co-localize according to both dSTORM and co-IP. When PANC-1 cells were treated with a selective CXCR4 agonist (CXCL12) or a combination of CXCL12 and dermorphin, high levels of nuclear pERK1/2 were observed (FIG. 16D). Next, the functional consequence of the cytoplasmic localization of pERK1/2 was evaluated by monitoring the phosphorylation status of one of its cytoplasmic substrates: p90 ribosomal S6 kinase (RSK) (Poon and Seger, 2006), an important factor for cell motility, invasion, and metastasis. In PANC-1 cells, RSK was rapidly phosphorylated in different locations depending on the treatment type. Treatment with individual agonists resulted in nuclear pRSK while treatment with the combination resulted in both cytoplasmic and nuclear pRSK (FIG. 5D). Thus, in PANC-1 cells, co-activation of MOR and SSTR2 appears to uniquely orchestrate phosphorylation of ERK1/2 consistent with β-arrestin2 signaling.

Figure 17A:
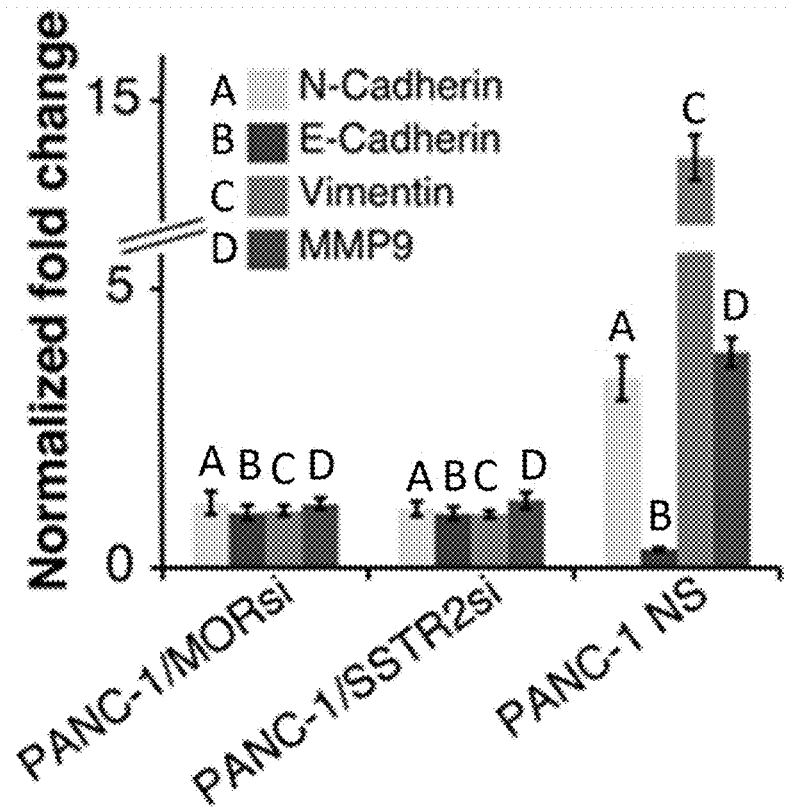
FIG. 17A-17C: Expression of epithelial and mesenchymal markers upon agonist treatment.
Figure 17B:
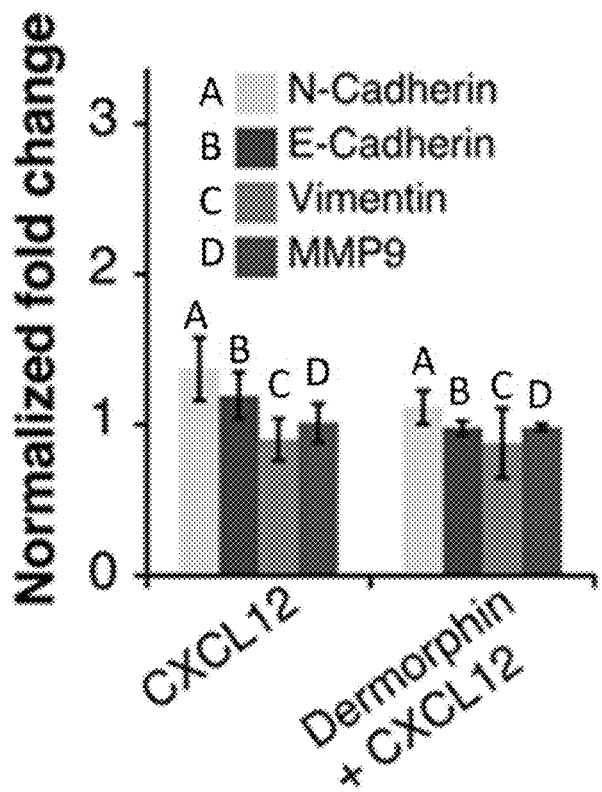
Figure 17C:
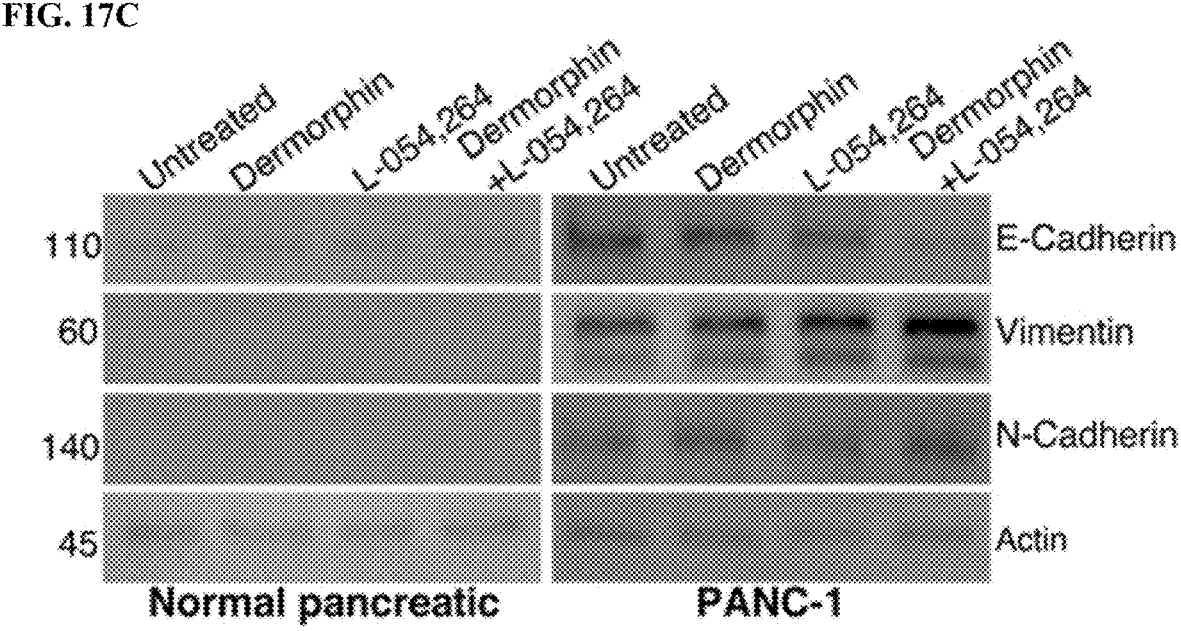

Simultaneous Activation of MOR and SSTR2 Influences the Metastatic Potential of PDAC Cells Co-activation of associating GPCRs could be physiologically relevant for PDAC: Endogenous ligands are able to continuously activate GPCRs (Heasley, 2001) and MOR agonists such as morphine are often used in PDAC palliative treatment (Mercadante et al., 2010). According to clinical studies in PDAC, a strong correlation may exist between aberrant ERK1/2 activation and a process that is important to initiating metastasis, namely, epithelial to mesenchymal transition (EMT) (Javle et al., 2007). Specifically, patient PDAC cells often undergo a switch from E-cadherin to N-cadherin expression (Nakajima et al., 2004; Javle et al., 2007; Berx and van Roy, 2009) and show an increase in vimentin (Javle et al., 2007; Handra-Luca et al., 2011) and MMP9 (Jones et al., 2004). Considering this association between ERK1/2 status and EMT in PDAC, Applicants examined whether MOR-SSTR2 activation changes the metastatic potential of cells. After PANC-1 cells were treated with dermorphin alone, L-054,264 alone, or a combination of the two, expression levels of EMT markers were measured by RT-PCR and Western blots. Importantly, only the combined MOR and SSTR2 agonist treatment (24 h, FIG. 5E) in PANC-1 cells showed features consistent with EMT. Compared to levels found with the single agonist treatments, mRNA levels observed with the combination treatment significantly increased for vimentin, MMP9, and N-cadherin while they decreased for E-cadherin. This effect was not observed in normal pancreatic cells upon all treatments. As a control experiment, the agonist combination treatment was evaluated in PANC-1 knockdown cells. In PANC-1/MORsi and PANC-1/SSTR2si cells, the treatment did not affect mRNA levels of the four EMT markers (FIG. 17B). Moreover, in PANC-1 cells neither a combination of MOR/CXCR4 agonists nor an individual CXCR4 agonist affected the mRNA levels of the four EMT markers (FIG. 17C). In addition to these RT-PCR studies, the selective impact of the combination treatment on EMT markers in PANC-1 cells was also confirmed at the protein level. The combined MOR and SSTR2 agonists increased protein levels of vimentin and N-cadherin and decreased levels of E-cadherin in PANC-1 cells but not in normal pancreatic cells (FIG. 17D).

GPCR Antagonists as Treatment for Pancreatic Cancer

Given that 1) EMT inhibition can sensitize tumors to gemcitabine (first line treatment in PDAC) (Zheng et al., 2015; Wang et al., 2014) and 2) treatment with MOR antagonist reduces mesenchymal marker expression (preliminary data, not shown), we will investigate the effect of MOR and SSTR2 antagonists alone and in combination with gemcitabine on cell survival and metastatic potential.

DISCUSSION

To date, conventional targets in PDAC have not yielded an effective chemotherapeutic agent for a number of reasons: The disease is usually detected at a late stage, when it is more difficult to treat; it progresses aggressively; and it is difficult to deliver PDAC drugs efficiently (Li et al., 2004a; Oberstein and Olive, 2013). The limitations of current approaches are reflected in PDAC's dismal five-year survival rate of 7% (Howlader N, 2014). To develop an orthogonal approach capable of complementing the current clinical regimen, Applicants have focused their attention on GPCR heteromers. Since GPCR heteromers are more commonly observed in pathological cells (AbdAlla et al., 2001; Grant et al., 2008; Azdad et al., 2009; Albizu et al., 2011; Rozenfeld et al., 2011; Bushlin et al., 2012), they are ideal targets for developing a selective pharmacological agent and are under scrutiny for a number of neurological disorders. However, in pancreatic cancer, they remain a relatively untapped resource. The focus has been predominantly on monomeric GPCRs such as SSTR2 (Cascinu et al., 1995) and CXCR4 (Singh et al., 2010). Because such receptors exhibit complex signaling patterns and tend to make heteromers under pathological conditions, Applicants investigated their association in PDAC by coupling classical biochemical experiments with quantitative super-resolution imaging techniques.

Using Western blots and RT-PCR (FIG. 1), pancreatic cells were shown to express MOR, CXCR4, and SSTR2. Pointillistic super-resolution microscopy methods were then applied to obtain details about receptor distribution at the single molecule level. To achieve high spatial resolution, pointillistic techniques such as dSTORM use total internal reflection microscopy illumination and single marker switching to restrict light emission to a single fluorophore in a diffraction-limited spot (Betzig et al., 2006; Hess et al., 2006; Rust et al., 2006; Folling et al., 2008; Wombacher et al., 2010). In this way, a resolution of approximately 10-25 nm is obtained and single-molecule sensitivity is achieved along large spatial areas. Applicants further applied a rigorous quantitative analysis: Voronoï tessellation analysis (Levet et al., 2015) was used to determine receptor shape and size and pair-correlation analysis (Sengupta et al., 2011; Sengupta et al., 2013) was used to obtain information on the extent of co-localization between receptors. The results suggest that MOR, SSTR2, and CXCR4 form clusters with an average radius between 35 and 55 nm. This is consistent with the organization of receptors into signaling domains and possible partial association with lipid rafts (Tobin et al., 2014).

PC-dSTORM was used to define the co-localization of CXCR4, MOR, and SSTR2. The impact of cellular environment was examined by using healthy cells, cancerous cells, and the external layer of MCTS. MCTS can recapitulate 1) cellular interactions and tumor heterogeneity (e.g. contain both quiescent and proliferative cells (Sutherland, 1988)) and 2) histomorphological, functional, and microenvironmental features of human tumor tissue (Hirschhaeuser et al., 2010). According to the results, MOR and SSTR2 co-localize in only malignant samples (FIG. 2). This co-localization largely occurs in clustered regions. Conversely, in all the cases, MOR and CXCR4 did not co-localize (FIG. 3). The data was validated with two important controls: No appreciable signal was detected with 1) blocking peptides (FIGS. 6 and 9B,D) and 2) stable PANC-1 cell knockdowns of the corresponding receptor (FIG. 7). In NS control PANC-1 cells, signals for MOR, SSTR2, and CXCR4 were detected at levels and distributions similar to wild type PANC-1 cells. Additionally, the choice of label (Alexa Fluor 647 vs Atto 488) did not produce significant differences in cross-correlation curves (FIG. 10). As demonstrated by Monte Carlo simulations, antibody detection efficiencies do not significantly influence conclusions obtained from correlation curves (FIG. 11).

To confirm the dSTORM-detected GPCR interactions, Applicants performed immunoprecipitation experiments. The interactions observed in the super-resolution experiments were similar to those observed through the biochemical approach. In both healthy and malignant pancreatic cells, no interactions were observed between MOR and CXCR4, whereas in malignant PANC-1 cells, SSTR2 co-immuno-precipitates with MOR (FIG. 2D and FIG. 3D).

To examine the relevance of MOR-SSTR2 co-localization under native conditions, the study was extended to include patient tissue samples. While super-resolution imaging of patient samples is time intensive and technically challenging (relatively high background, limited labeling options, and sample heterogeneity among others), in the current study this was addressed by optimizing both sample preparation and imaging conditions, and by sampling multiple sections/regions of tissues while selectively labeling epithelial cells. Specifically, typical pathology markers were used for epithelial tissue, keratin 8 and 18 (Moll et al., 1982). Furthermore, the super-resolution data sets from tissue imaging were analyzed quantitatively (FIG. 4). The results suggest GPCR organization is significantly different in normal and malignant tissue samples. The cluster size is larger for both MOR and SSTR2 in cancer tissue compared to healthy margins. Additionally, while they do not co-localize in healthy margins of three patients, MOR-SSTR2 clearly co-localize in cancerous patient tissues. Importantly, this is the first time an association has been described between MOR and SSTR2 in pancreatic cancer.

Given that MOR-SSTR2 is a newly identified associated receptor pair in PDAC, Applicants further investigated the cellular localization of the two receptors upon agonist activation with confocal microscopy. As expected, largely membrane localization of MOR and SSTR2 with appreciable co-localization was seen in the steady state, while co-activation with selective agonists led to receptor internalization.

Applicants further investigated signaling of MOR-SSTR2 in pancreatic environments. GPCR signaling pathways are complex and influenced by both the cellular environment (Schmid and Bohn, 2009) and interactions with other receptors—e.g. receptor tyrosine kinases (RTKs) and/or other GPCRs (Belcheva et al., 2001; Billadeau et al., 2006; Rozenfeld and Devi, 2007; Kenakin, 2011). While signaling pathways proceed by different G-protein subclasses, β-arrestin2, or RTKs (Belcheva et al., 2001; Belcheva et al., 2003; Billadeau et al., 2006; Fujioka et al., 2011), they often converge at ERK1/2. Canonical G-protein mediated signaling leads to rapid and transient phosphorylation of ERK1/2, which is targeted to the nucleus. Likewise, signaling through EGFR can induce fast phosphorylation of ERK1/2, which also leads to nuclear targeting. Conversely, β-arrestin2 mediated signaling produces both slower and more sustained phosphorylation of ERK1/2, which is subsequently targeted to the cytosol and endosomes (Ahn et al., 2004; Gesty-Palmer et al., 2006; Shenoy et al., 2006; Rozenfeld and Devi, 2007; Cervantes et al., 2010). Since a downstream phenotypic assay that quantifies spatio-temporal ERK/1/2 phosphorylation (Ahn et al., 2004) is important for investigating functional-crosstalk between associated GPCRs, Applicants studied how activating MOR and/or SSTR2 affects ERK1/2 and EGFR phosphorylation. The three treatments consisted of 1) a specific MOR agonist-dermorphin, 2) a specific SSTR2 agonist-L-054,264, and 3) a combination of the two. In malignant PANC-1 cells, activating MOR and SSTR2 simultaneously with the combination produced unique downstream effects: 1) Consistent with previous reports in breast cancer cells (Kharmate et al., 2013), the combination failed to induce EGFR phosphorylation; 2) it produced slower and more sustained pERK1/2 activation; and 3) it predominantly promoted cytoplasmic pERK1/2 and resulted in cytoplasmic pRSK component. This is particularly significantly considering that cytoplasmic pERK has been detected in a large number of patient PDAC samples (Pham et al., 2008; Dutruel et al., 2014). Importantly, mostly nuclear pERK1/2 was observed in MOR, SSTR2, and β-arrestin2 knockdown PANC-1 cells upon combination treatment. Taking the results altogether, co-activation of MOR-SSTR2 in PANC-1 cells appears to proceed by a distinct pathway that does not appear to involve EGFR transactivation and is consistent with β-arrestin2 signaling.

Figure 5E:
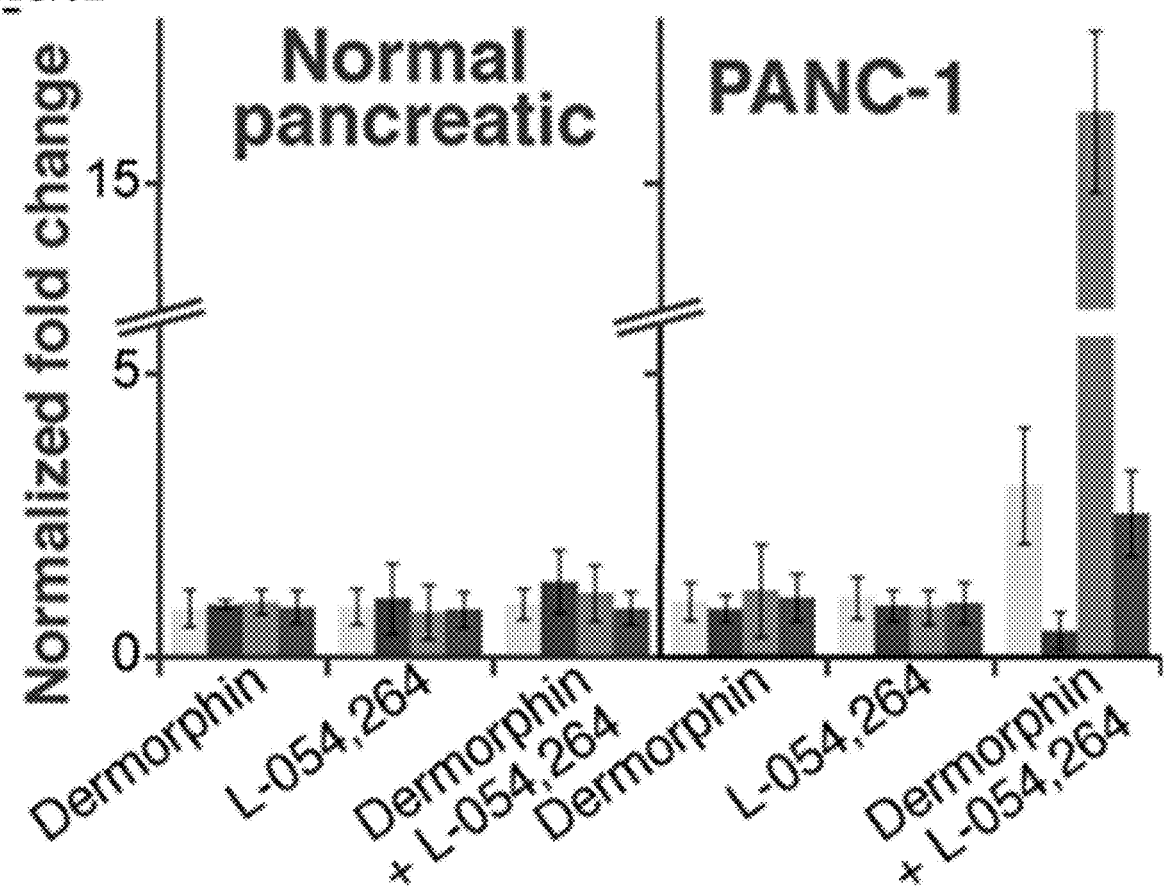

Given that PDAC is characterized by frequent metastasis to remote sites (only about 20% of tumors are discovered in early stages (Li et al., 2004a)), Applicants investigated whether this distinct signaling pathway contributes to the metastatic potential of cells. Expression of mesenchymal proteins in cancer cells is an indicator of aggressive tumor biology for PDAC (Javle et al., 2007) and has been associated with poor patient survival (Javle et al., 2007; Handra-Luca et al., 2011; Jiang et al., 2015), chemo-resistance (Arumugam et al., 2009; Wang et al., 2009), and invasiveness (Nakajima et al., 2004; Javle et al., 2007; Zhang et al., 2012). Upon administration of the three treatments, the expression of EMT markers was quantified. According to the results, co-activation of MOR and SSTR2 in PANC-1 cells leads to increased expression of vimentin, MMP9, and N-cadherin; and decreased expression of E-cadherin (FIG. 5E and FIG. 17). This effect was not observed in normal pancreatic cells PANC-1/MORsi and PANC-1/SSTR2si cells.

By combining quantitative super-resolution analyses with biochemical approaches, a molecular signature unique to pancreatic adenocarcinoma was identified. Two G-protein coupled receptors, MOR and SSTR2, were shown to associate uniquely in PDAC. Moreover, co-activation of MOR and SSTR2 produced a distinct signaling pathway that appears to employ β-arrestin2 signaling and increase the metastatic potential of cells. Thus, MOR-SSTR2 in PDAC may constitute a novel and specific pharmacological target.

Materials and Methods

Coverslip Preparation.

25-mm #1.5 coverslips (Warner Instruments) were cleaned with 1% Hellmanex III (Fisher Scientific) for 3 h at 25° C. and rinsed with distilled water, and placed in acetone at 70° C. for 10 min. This was followed by a secondary cleaning with a mixture of 1:1:5 (v/v) of hydrogen peroxide (30%):ammonium hydroxide:water for 1 h at 70° C. Coverslips were rinsed in distilled water and stored in 100% ethanol. Cleaned coverslips were subsequently flame dried and placed in sterile 35-mm tissue culture dishes. For dSTORM microscopy, cells were grown on coverslips coated with fibronectin-like engineered protein (25 μg/mL in PBS, pH 7.4, Sigma) as described before (Tobin et al., 2014). For tissue imaging, coverslips were coated with 0.03% gelatin for 10 min at room temperature; solution was aspirated, and the coverslips were air-dried just before sample addition.

Cell Culture.

COS-7, HEK293T, PANC-1, BxPC3, SU.86.86, CAPAN-1, and MCF-7 cells (originally obtained from the American Type Culture Collection, ATCC) were cultured in Phenol Red-free DMEM or RPMI-1640 (only for BxPC3 cells) supplemented with 10% fetal bovine serum, 1 mM sodium pyruvate, 100 units/mL penicillin, 100 units/mL streptomycin, and 2 mM L-alanyl-L-glutamine. Human immortalized pancreatic epithelial cells (AddexBio) were grown in Keratinocyte SFM media with defined Keratinocyte SFM supplements (Life Technologies) as per the supplier's suggestion and subsequently cultured in Phenol Red-free Epilife media supplemented with calcium chloride and Epilife supplements (Life Technologies). CHO-S cells (Invitrogen) were cultured per manufacturer' specifications in FreeStyle media.

To obtain a large and reproducible quantity of MCTS, Applicants placed 1000 cells/well into 96 well round bottom plates coated with PolyHema (Sigma). A small amount (~1% of total media) of Phenol Red-free Matrigel (Corning) was included in growth media. MCTS of consistent size (450 μm) generally formed within 4 days. For super-resolution imaging of surface layers, MCTS were placed on fibronectin-like engineered protein coated coverslips for 3 h at 37° C. in the cell incubator to attach, and were subsequently fixed.

Knockdowns. MOR, SSTR2, CXCR4, and β-arrestin2 knockdowns were performed using GIPZ lentivirals shRNAmir constructs specific for each GPCR (GE Dharmacon). The miRNA is a polycistronic RNA with TurboGFP allowing visualization of cells that express the shRNA. The shRNAmir construct was stably integrated in the PANC-1 cells per the manufacturer's instructions. First, the lentivirus was packaged using the Trans-LentiviralshRNA packaging system. The lentivirus system was then transfected into HEK293T cells (ATCC) using calcium phosphate. Packaged lentivirus was concentrated for 48 hours after transfection. The supernatant with lentiviral particles containing shRNAmir was directly transduced into PANC-1 cells. Briefly, approximately $5 \times 10^4$ PANC-1 cells were added to each well in a 24-well plate. A final concentration of 8 µg/mL polybrene and 500 µL of packaged lentivirus were added to the cells. The cells were incubated for 8 h and then the medium was changed. After 48 h, DMEM media supplemented with 10% fetal bovine serum, 1 mM sodium pyruvate, 100 units/mL penicillin, 100 units/mL streptomycin, and 2 mM L-alanyl-L-glutamine supplemented with 2 µg/mL puromycin was added to start selection for stably transduced cells (PANC-1/SSTR2si. PANC-1/MORsi, PANC-1/CXCR4si, and PANC-1/β-arrestin2si). As a control, GIPZ vector containing a non-silencing control was also transfected (PANC-1 NS).

Each shRNA construct has been bioinformatically verified to match NCBI sequence data: shRNA MOR AntiSense sequence of SEQ ID NO:9: TTACTTTATGTGTTACTAC, RefSeq NM_001145279; shRNA SSTR2 AntiSense sequence of SEQ ID NO:10: TAAATGACAAGTGTGTTGC, RefSeq NM_001050. shRNA CXCR4 AntiSense sequence of SEQ ID NO:11: ATCTATGCATAAACAGCTG, RefSeq NM_001008540 and NM_003467 β-arrestin2 Antisense sequence of SEQ ID NO:12: ACCTGGTCATCTTGTTCGA RefSeq NM_199004.

Antibodies and Fluorescent Dye Conjugation.

The following primary antibodies were purchased: anti-MOR (guinea pig polyclonal, Abcam); anti-SSTR2 (rabbit polyclonal, Neuromics); anti-CXCR4 (mouse monoclonal, Neuromics); and anti-cytokeratin 8 & 18 (mouse monoclonal, Cell Marque/Sigma). Purchased purified secondary antibodies include rabbit anti-guinea pig (polyclonal, Abcam); goat anti-rabbit (polyclonal, Abcam); and goat anti-mouse (polyclonal, EMD Millipore). Antibody references are provided below. Secondary antibodies were labeled with Alexa Fluor 405, Alexa Fluor 647 (Life Technologies) or Atto 488 (Sigma) containing an N-hydroxysuccinidimidyl ester (NHS) group for conjugation to proteins. A solution containing a 6-10 molar excess of dye dissolved in dimethyl sulfoxide (DMSO) was mixed with a solution of 1 mg/mL secondary antibody in PBS pH 7.4 with 0.02 M NaHCO$_3$; the resulting solution was allowed to react for 30 min at room temperature. The solution was quenched with 1.5 M hydroxylamine (pH 8.5) for 10 min. Unconjugated dye was removed by passing the solution through a size exclusion chromatography column (Bio-Rad). Prior to the experiment, labeled antibody was passed through a 300 kDa concentrator to remove any potential aggregates. The concentration of labeled secondary antibodies was measured by a NanoDrop 1000 (Thermo) and calculated with respect to the dye's correction factor. Approximately one dye per antibody was obtained in all cases for Atto 488 and Alexa Fluor 647. Secondary antibodies were used freshly labeled.

Primary Antibodies.

The antibodies used in assays reported in the paper have all been well characterized for human reactivity in the antibody profile database Antibodypedia and 1DegreeBio. The antibodies used are available through multiple vendors and the references for these particular reagents have been gathered from the database, original manufacturers' website, and our published work. Primary antibodies include anti-MOR (guinea pig polyclonal, Neuromics, Abcam) (Manzke et al., 2010; Nassirpour et al., 2010; Tobin et al., 2014); anti-SSTR2 (rabbit polyclonal, Neuromics) (Reubi et al., 1998; Reubi et al., 1999); anti-CXCR4 (mouse monoclonal, Neuromics) (Haringman et al., 2006; Pfeiffer et al., 2009); anti-phospho-ERK1/2 (Thr202/Tyr204) (rabbit monoclonal, Cell Signaling) (Mark et al., 2008; Chiron et al., 2009); anti-ERK1/2 (rabbit polyclonal, Abcam) (Gertsch et al., 2008; Chen et al., 2009); anti-phospho-EGFR (Tyr1068) (rabbit monoclonal, Cell Signaling) (Katayama et al., 2012; Yoshikawa et al., 2013); anti-EGFR (rabbit monoclonal, Abcam) (Burga et al., 2011; Giles et al., 2013); anti-β-actin (mouse monoclonal, Cell signaling) (Tarassishin et al., 2011; Zheng et al., 2012); anti-cytokeratin 8 & 18 (mouse monoclonal, Cell Marque/Sigma) (Angus et al., 1987; Sasaki et al., 1998); anti-vimentin (rabbit monoclonal, Cell Signaling) (Lacher et al., 2011; Matsuyama et al., 2013); anti-E-cadherin (rabbit monoclonal, Cell signaling) (Kong et al., 2010; Stairs et al., 2011); anti-N-cadherin (rabbit monoclonal, Cell Signaling) (Chen et al., 2013), anti-phospho-p90RSK (Thr573) (rabbit monoclonal, Cell Signaling) (Zaru et al., 2007; Kosako et al., 2009), anti-Na/K ATPase a1 (D4Y7E) (rabbit monoclonal, Cell Signaling); Histone H3 (rabbit monoclonal, Cell Signaling) (Wang et al., 2011); anti-β-arrestin2 (rabbit polyclonal) was a kind gift from Dr. J. Benovic (Shankar et al., 2010). Secondary antibodies: Goat Anti-Guinea pig IgG H&L (HRP) (Abcam) (Houl et al., 2006), Goat Anti-Mouse IgG H&L (HRP) (Abcam)(Caci et al., 2015), Goat Anti-Rabbit IgG H&L (HRP) (Abcam) (Janiszewska et al., 2015), Goat anti-mouse (polyclonal, Abcam) (Tammachote et al., 2012), Goat anti-rabbit (polyclonal, Abcam) (KA, 2009), Goat anti-guinea pig (polyclonal, Abcam) (Houl et al., 2006).

Immunocytochemistry.

Immunocytochemistry was done according to established protocols. Antibody concentrations and incubation times were individually optimized. Briefly, cells were fixed for 30 min at room temperature with 4% (w/v) paraformaldehyde and 0.2% (w/v) glutaraldehyde and inactivated with 25 mM glycine for 10 min. After washes in PBS, cells were incubated in permeabilization buffer (PB, 0.1-0.5% tween-20, 5% BSA in PBS) for 20 min. After a wash, cells were incubated for 1 h with 2 µg/mL of primary antibody/antibodies. Subsequently, cells were extensively washed and incubated with 2 µg/mL of labeled secondary antibody/antibodies for 45 min. To avoid interaction between goat anti-rabbit and rabbit anti-guinea pig secondary antibodies, Applicants first incubated cells with secondary anti-rabbit antibody, extensively washed and then incubated cells with secondary anti-guinea pig antibody. After PBS wash, cells were post-fixed for 10 min with 4% (w/v) paraformaldehyde and 0.2% (w/v) glutaraldehyde, and inactivated with 25 mM glycine for 10 min at room temperature. For control experiments, 5 molar excess of blocking peptide was pre-incubated at with specific primary antibody/antibodies for 10 min at room temperature; all other steps were done according to the above protocol. Coverslips were imaged immediately after preparation in Attofluor cell chambers (Life Technologies) in 50 mM Tris (pH 8.0), 10 mM NaCl, and 10% glucose imaging buffer containing mercaptoethylamine (MEA, 100 mM) and GLOX (10% v/v) as previously described (Dempsey et al., 2011).

Tissue Samples and Immunohistochemistry.

Fresh frozen tissues in OCT compound (Fisher Scientific) were cut using Cryostat LEICA CM3050S; slice thickness was 8 µm. Glandular tissue was sliced to allow imagining of normal/neoplastic glands. Tissue slices were put on clean coverslips coated with 0.03% gelatin, incubated at room temperature for 5 min and rehydrated with PBS for 10 min. Samples were fixed for 30 min with 4% (w/v) paraformaldehyde and 0.2% (w/v) glutaraldehyde, and inactivated with 25 mM glycine for 10 min at room temperature. Subsequently, samples were incubated with antibodies (as described above in the immunocytochemistry protocol) to detect MOR and SSTR2. After extensive washes, tissues were incubated with 2 µg/mL of cytokeratin antibody 8 & 18 (Cell Marque) in PB buffer for 30 min. Tissues were subsequently washed, and incubated with 2 µg/mL of Alexa Fluor 405 labeled secondary antibody in PB buffer for 15 min. Tissue samples were extensively washed again and post-fixed for 10 min. Samples were immediately imaged on a Nikon N-STORM super-resolution microscope. Images were processed with Nikon Elements N-STORM software to identify peaks. Tissue samples were collected under Institutional Review Board (IRB) number 06129 and informed consent was obtained from all subjects.

Optical Setup and Image Acquisition.

Measurements were performed on a 3D N-STORM super-resolution microscope (Nikon) configured for total internal reflection fluorescence (TIRF). The N-STORM system, Nikon Instruments, consists of a fully automatic Ti-E inverted microscope with piezo stage on a vibration isolation table with a 100×1.49 NA TIRF objective (Apo); an N-STORM lens and λ/4 lens, and a Quad cube C-NSTORM (97355 Chroma) with filters for 405, 488, 561, and 640 nm light. The microscope is equipped with a Perfect Focus Motor to maintain imaging on the desired focal plane; an MLC-MBP-ND laser launch with 405 nm, 488 nm, 561 nm, and 647 nm lasers, (Agilent); and an EM-CCD camera iXon DU897-ultra, (Andor Technology). Data was acquired using NIS Elements 4.3 software with automatic drift correction. Laser powers used to activate and/or image dyes were 120, 60 and 6 mW (measured out of the optical fiber) for 647, 488 and 405 nm respectively. Two-color imaging was done with sequential activation, switching the laser from 488 to 647 for every frame. 20,000 frames were acquired in each channel using an exposure time of 9 ms.

Applicants imaged 2D cultures of cells, outer layer of MCTS, and thin sections of tissue samples. All samples were imaged in total internal reflection fluorescence (TIRF) mode and trans-light was used to observe selected regions. Prior to microscopy, Applicants marked locations of MCTS and tissue samples on the coverslip with the marker to aid in region selection. For tissue imaging, epithelial cells were identified with quick scanning using a low power 405 nm laser. Applicants adjusted the TIRF angle and focus to image tissue regions close to the coverslip with appreciable 488 nm and/or 647 nm signal (appearing in the area that matched Keratin 8 & 18 signal). For tissues, 405 channel imaging of Alexa Fluor 405 was performed after the two-color dSTORM acquisition.

To select flat membrane segments and to avoid artifacts from 3D topology of the membrane projecting into the 2D imaging plane, Applicants imaged the same segments with a slightly shifted focal plane (minimal signal was observed above membrane segments). Additionally, Applicants also examined the photon count distributions for these regions after processing and confirmed that photon counts were in an expected range and did not show bimodal distributions.

Image Analysis.

Peak localization was performed using NIS Elements 4.3 software. Minimum number of photons was set to 700. Settings for peak localization are as follows: minimum peak width 200 nm, maximum peak width 400 nm, max axial ratio 1.3, maximum displacement 1 pixel. Peak height thresholds were set to 8000 and 11000 for Atto 488 and Alexa Fluor 647 respectively. The average localization precision was 17 nm in the 488 channel and 12 nm in the 647 channel, as detected by NIS-Elements. After peak localization, the density of peaks and cross-correlation functions were computed as described previously (Sengupta et al., 2011; Sengupta et al., 2013). Briefly, for two-color imaging, two separate binary images of cells were computed using peak coordinate centers obtained from NIS elements. A value of 1 was assigned for pixels with detected peaks while value of 0 was assigned elsewhere. Next, square regions of interest (ROI) with size of 80 µm² were randomly selected. Cross-correlation was computed using Fast Fourier Transforms with previously published algorithm in MATLAB (Sengupta et al., 2013). In all cases, error bars represent standard error of the mean, calculated individually for each data point. All presented images were color inverted for clarity. No other modifications were done. Image tessellation was performed using SR-Tesseler software as previously described (Levet et al., 2015).

MOR, SSTR2, and CXCR4 Tessellation Cluster Analysis.

Peak localization data (prepared as described in Materials and Methods) was imported to the freely available SR-Tesseler software (Levet et al., 2015). All cell images were analyzed using the same segmentation settings in SR-Tesseler (each color channel data was loaded separately). Steps to identify clusters in each cell image were carried out as described in the software manual. Briefly, Voronoï diagrams were first applied to the data. Object segmentation was then performed by using a combination of adjusted and default parameters, including the minimum object area (set to 0.01 pixels²), the minimum number of localizations per object (set to 5), and the density factor (set at the default of 2). Receptor cluster data was subsequently extracted from object data using the same parameters. Finally, the cluster data was exported from SR-Tesseler and, using custom code in Matlab, averages were prepared for the results shown in FIG. 10.

Protein Extracts and Immunoblotting.

To prepare protein extracts, cells were pelleted by centrifugation and washed twice in PBS. The pellet was resuspended in lysis buffer (50 mM Tris, pH 8.0, 150 mM sodium chloride, 1% NP-40, supplemented Protease and Phosphatase Inhibitor Mini Tablets, Pierce) and incubated on a rotator for 30 min at 4° C. Subsequently, the cells were pelleted by centrifugation at 10,000 rpm for 20 min at 4° C. The protein lysate (supernatant) was used immediately or stored at −80° C. Membrane proteins were isolated using the Mem-Per Plus Membrane protein isolation kit (Thermo Scientific) per the manufacturer' instructions. Briefly, adherent cells were scraped and centrifuged for 5 min at 300×g. The cell pellet was washed 2 times using Cell Wash solution and centrifuged for 5 min at 300×g. The cell pellet was permeabilized using Permeabilization Buffer and incubated at 4° C. for 10 mins on a rotator. The permeabilized cells were then centrifuged at 16000×g for 15 min. The supernatant containing the cytosolic proteins was removed and stored at −80° C. The remaining cell pellet was resuspended in Solubilization Buffer and incubated for 30 min on a rotator at 4° C. After centrifugation at 16000×g for 15 min at 4° C., the supernatant containing the fractionated membrane proteins were removed at stored at −80° C. The lysates were subjected to SDS-polyacrylamide gel electrophoresis and Western blotting using standard procedures. Primary antibodies included anti-phospho-ERK1/2 (Thr202/Tyr204) (rabbit monoclonal, Cell Signaling); anti-ERK1/2 (rabbit polyclonal, Abcam); anti-EGFR (rabbit monoclonal, Abcam); anti-phospho EGFR (Tyr1068) (rabbit monoclonal, Cell Signaling); anti-MOR (guinea pig polyclonal, Abcam); anti-SSTR2 (rabbit polyclonal, Neuromics); anti-CXCR4 (mouse monoclonal, Neuromics); and anti-O-actin (mouse monoclonal, Cell signaling); anti-Na/K ATPase (rabbit monoclonal, Cell Signaling). Proteins were detected with Pierce ECL detection reagents (Pierce). The blots were imaged using the Chemi-Doc™ Touch Imaging system or film developer.

Epithelial and Mesenchymal Markers Western Blots.

PANC-1 cells were treated with 1) 10 nM dermorphin [Y(D-ALA)FGYPKC; Genscript], 2) 10 nM (1R,1'S,3'R/1R,1'R,3'S)-L-054,264 (Tocris) individually and in combination for 24 hrs. Cells were lysed as described above for immunoblotting with EMT marker antibodies (Vimentin rabbit monoclonal, E-Cadherin rabbit monoclonal, N-Cadherin rabbit monoclonal, Epithelial-Mesenchymal Transition Antibody Sample Kit, Cell Signaling) according to the manufacturer's protocol. Blots were imaged using the Image Lab software (Biorad).

Kinetic Study.

Cells were treated with 10 nM Dermorphin [Y(D-ALA)FGYPKC; Genscript], 10 nM (1R,1'S,3'R/1R,1'R,3'S)-L-054,264 (Tocris) individually and in combination for the indicated times. Cells were lysed for immunoblotting with phospho-ERK1/2, total ERK1/2, phospho-EGFR and total EGFR. Blots were imaged on film and quantified using the Image Lab software (Biorad). ERK1/2 and EGFR phosphorylation at each time point was quantified and normalized by calculating the ratio of pERK1/2 over total ERK1/2 and pEGFR over total EGFR in each lane. The data represents the percentage of maximum response to dermorphin treatment. P values were obtained using the single tail T-test for the same time point between dermorphin activation and either L-054,264 or combined L-054,264 and dermorphin activation.

Cell Fractionation.

Nuclear and cytoplasmic extracts were made according to previously published protocols (Smith et al., 2004; Rozenfeld and Devi, 2007). Briefly, PANC-1 cells were treated with 10 nM dermorphin [Y(D-ALA)FGYPKC; Genscript], 10 nM (1R,1'S,3'R/1R,1'R,3'S)-L-054,264 (Tocris) individually and in combination for the indicated times. Following the treatment, cells were washed in ice-cold PBS three times and scraped into lysis buffer (10 mM Tris, pH 7.4, 10 mM NaCl, 3 mM $MgCl_2$, 1 mM EGTA, 1 mM sodium orthovanadate, and a protease phosphatase inhibitor tablet; Pierce) and incubated on ice for 10 min. The lysate was then homogenized and centrifuged at 375×g for 5 min. The pellet consisting of the nuclear fraction was washed 5 times with lysis buffer containing 0.1% NP-40 to remove any non-nuclear contamination and resuspended in lysis buffer containing NP-40. The soluble fraction was centrifuged twice at 375×g to remove nuclear contamination and was used as the cytosolic fraction. Fractions were then used for immunoblotting for anti-phospho-ERK1/2, anti-phospho-p90RSK (Thr573) (rabbit polyclonal; Cell Signaling), anti-β-actin as a loading control for the cytoplasmic fraction, and Histone H3 antibody (rabbit monoclonal; Cell Signaling) was used as a loading control for the nuclear fraction.

Extraction of RNA, cDNA Synthesis, and RT-PCR.

RNA was isolated using the RNAeasy Plus Kit (Qiagen) according to the manufacturer's protocol. For the EMT markers assay, cells were first treated with appropriate agonists where indicated for 24 hours followed by cell lysis and RNA extraction. cDNA was synthesized from 2 μg RNA using Bioline cDNA synthesis kit according to the manufacturer's protocol. The synthesized cDNAs were used as templates for PCRs with primers as described below. RT-PCR was performed using 5×RT Mastermix (Applied Biosystems). The reactions were analyzed on the CFX96 Real time instrument (Biorad). Themocycler conditions were 95° C. for 10 min for 1 cycle, 95° C. for 15 sec and 60° C. for 1 min for 50 cycles. GAPDH was used as an internal control. For GPCR assays, COS-7 cells were used as negative and MCF-7 cells as positive controls. For EMT marker assays, fold change was calculated as a ratio of treated to untreated control.

RT-PCR Primer Selection.

For RT-PCR Applicants used:

```
SSTR2-forward
(5'-AAGTCCTCTGGAATCCGAGT-3')
and

SSTR2-reverse
(5'-GAGGACATTCTGGAAGCTCT-3')
primers (Fujita et al., 1994);

MOR-forward
(5'-TCTGGCTCCAAAGAAAAGGA-3')
and

MOR-reverse
(5'-CAATGCAGAAGTGCCAAGAA-3')
primers (Lu et al., 2013);

CXCR4-forward
(5'-GACGCCAACATAGACCACCT-3')
and

CXCR4-reverse
(5'-CCGTGGCAAACTGGTACTTT-3')
primers (Sun et al., 2014);

Vimentin-forward
(5'-TACAGGAAGCTGCTGGAAGG-3')
and

Vimentin-reverse
(5'-ACCAGAGGGAGTGAATCCAG-3')
primers (Ma et al., 2016);

E-cadherin-forward
(5'-GGCCAGGAAATCACATCCTA-3')
and

E-cadherin-reverse
(5'-GGCAGTGTCTCTCCAAATCC-3')
primers (Li et al., 2015),

N-Cadherin-forward
(5'-CTCCATGTGCCGGATAGC-3')
and

N-cadherin-reverse
(5'-CGATTTCACCAGAAGCCTCTAC-3')
primers (Woods et al., 2014);

MMP9-forward
(5'-GAACCAATCTCACCGACAGG-3')
and

MMP9-reverse
(5'-GCCACCCGAGTGTAACCATA-3')
primers (Sai et al., 2015)
```

-continued

β-arrestin2-forward
(5' GTCGAGCCCTAACTGCAAG 3')
and

β-arrestin2-reverse
(5' ACAAACACTTTGCGGTCCTTC 3')
primers (Jing et al., 2015)

Co-Immunoprecipitation.

Co-immunoprecipitation was performed using the co-immunoprecipitation kit (Pierce) per the manufacturer's protocol. Briefly, MOR antibody was immobilized using a coupling resin. PANC-1 or normal pancreatic epithelial cells were lysed using buffer containing 1% Nonidet P-40, 10% glycerol, 50 mM Tris-Cl, pH 7.4, 300 mM NaCl, 1.5 mM $MgCl_2$, 1 mM $CaCl_2$) and protease inhibitor tablets (Pierce) similarly as described before (Rozenfeld and Devi, 2007), pre-cleared and added to the antibody coupled resin and incubated with gentle shaking overnight at 4° C. After thorough washes, the protein sample co-immunoprecipitate was eluted and used for Western blotting with SSTR2 or CXCR4 antibodies. Actin was used as a loading control.

Sample Preparation for Confocal Microscopy.

For all studies, cells were plated and grown on coverslips in full media. For internalization studies, PANC-1 cells were treated with 1) 10 nM dermorphin; 2) 10 nM L-054,264; 3) 10 nM dermorphin plus 10 nM L-054,264 for 30 min. Untreated or agonist(s) treated cells were then fixed and immunostained for MOR and SSTR2 detection as described above. Images were acquired using a Zeiss LSM880 microscope and LD C-Apochromat 40x/1.1 W Corr M27 objective.

For pERK1/2 activation studies, after 24 hours, normal pancreatic and/or PANC-1 cells were treated with 1) 10 nM dermorphin; 2) 10 nM L-054,264; 3) 10 nM dermorphin plus 10 nM L-054,264; 4) 100 ng/ml CXCL12; and 5) 10 nM dermorphin plus 100 ng/ml CXCL12 for either 3 min or 30 min as indicated. PANC-1 NS, PANC-1/β arreatin2, PANC-1/SSTR2si and PANC-1/MORsi cells were treated with 10 nM dermorphin with 10 nM L-054,264 for 3 min. Following treatment, cells were washed and fixed with 4% (w/v) paraformaldehyde and 0.2% (w/v) glutaraldehyde for 30 min and inactivated with 25 mM glycine for 10 min. Cells were then washed in PBS and subsequently permeabilized on ice using 0.5% tween-20 in PBS for 20 min similarly as before (Smith et al., 2004). Cells were washed with PBS and blocked with 5% BSA in PBS for 10 min. Cells were incubated for 1 h at 37° C. with 2 µg/mL of primary antibody (anti-pERK1/2). Subsequently, cells were washed 3 times with 0.5% tween-20 in PBS for 5 min each and incubated with 2 µg/mL of Alexa Fluor 647 labeled secondary antibody in PB for 45 min. Following incubation with secondary antibody, cells were washed 3 times with 0.5% tween-20 in PBS. Cells were covered with mounting media DAPI (Vector Labs), mounted on slides, and imaged on a Zeiss LSM700 confocal microscope.

Monte Carlo Simulations.

Applicants detected on average ~2000 receptors in normal cells and ~6000 receptors in PANC-1 cells. While this is consistent with previously reported values for GPCRs (Jonas et al., 2015), Applicants wanted to investigate if antibody binding efficiency significantly influences the discovery of heterodimerization via cross-correlation curves. Applicants thus simulated super-resolution images of receptors with specified dimerization fractions at different receptor densities and antibody binding efficiencies. Applicants assumed detected densities of approximately 4 and 10 receptors per $µm^2$, representing lower and higher expressing cells on average, respectively. Applicants generated images with random receptor positions, and randomly assigned each receptor to either be a monomer (red or green, denoted R or G), homodimer (RR or GG), or heterodimer (RG) in specified ratio. Applicants assumed that receptor sizes were small enough that excluded area effects were negligible (forbidding two molecules to be less than 1 receptor diameter apart).

Using those randomly generated images, specified detection efficiency and the known photophysical properties of the fluorescent labels from experimental data (mean localization precision, average photon count, distribution of photon counts) Applicants generated sets of localizations in the red and green channels, which were translated into images. These localization maps were in the same format as the processed experimental data. Finally, this simulation data was passed to the same analysis software as the experimental data, and the cross-correlation between the red and green channels was computed.

In our simulations, the key variables were:
1) The number of red and green receptors per square micron.
2) The relative probabilities of the red and green receptors appearing as monomers or as homodimers and heterodimers.
3) The labeling probabilities for red and green receptors (corresponding to the antibody detection efficiency). Applicants allowed for the possibility of incomplete labeling, so that only a predefined fraction of the receptors were labeled red or green. Applicants did not assume a priori that the labeling probabilities were the same for both receptors.
4) The mean number of times a receptor turned on and produced a usable image during the experiment.
5) The mean localization precision and mean photon count for each label (2,500 and 1,500 for red and green respectively). The photon counts were assumed to be exponentially distributed, with a minimum threshold of 1000 photons for an image to be analyzed.

After randomly generating receptor positions, and randomly picking a subset of the receptors as fluorescently labeled, Applicants randomly generated a number of appearances from a geometric distribution for labeled receptors. Applicants first investigated the effect of average number of appearances of a fluorophore on data; Applicants did not observe significant variability for tested conditions. For the majority of the simulations Applicants thus used an average of 4 appearances for both channels. Applicants next generated a series of photon counts (from an exponential distribution with specified mean and minimum); the photon counts were used to determine the precision (standard deviation) of each position estimate, based on the assumption that the localization precision is inversely proportional to the square root of the photon count. For each receptor appearance, Applicants generated position estimates. Each estimate was drawn from a Gaussian (normal) distribution with a mean equal to the true position of the receptor and standard deviation equal to the localization precision. These position estimates were then used to construct a high resolution map of estimated receptor positions, and this image map was subsequently analyzed by the same Matlab program used to compute the cross-correlation function of the experimental data. All image simulations were performed in Python on a laptop computer. A simulation of a 16×16 µm field of view, containing approximately 5,000 receptors, could be conducted and the output rendered into a high resolution image (125 Mb) in less than 5 minutes.

TABLE 1

Exemplary SSTR2 antagonists useful for the compositions and methods provided herein
(peptide antagonists and small molecule antagonists are shown).

SSTR2 Antagonist Structure

H$_2$N-4-NO$_2$-Phe-c[D-Cys-Tyr-D-Trp-Lys-Val-Cys]-Tyr-NH$_2$
AcNH-4-NO$_2$-Phe-c[D-Cys-Tyr-D-Trp-Lys-Thr-Cys]-Tyr-NH$_2$
p-Cl-Phe-cyclo(D-Cys-Tyr-D-4-amino-Phe(carbamoyl)-Lys-Thr-Cys)D-Tyr-NH$_2$ (LM3):
(4-fluoro-Phe-c[D-Cys-(3-pyridyl)Ala-D-Trp-Lys-Val-Cys]-3-(2-naphthyl)ala-NH$_2$ (PRL-2882); (4-fluoro)Phe-c[D-Cys-(3-pyridyl)Ala-D-Trp-Lys-tert-Leu-Cys]-3-(2-naphthyl)Ala-NH$_2$ (PRL-2903); (4-chloro)Phe-c[D-Cys-(3-pyridyl)Ala-D-Trp-Lys-tert-Leu-Cys]-3-(2-naphthyl)Ala-NH$_2$ (PRL-2915)
Ac-DHis-DPhe-DIle-DArg-DTrp-DPhe-NH$_2$ (AC-178,335)
Ac-His-Phe-Ile-Arg-Trp-Phe-NH$_2$ (AC-178,335); H-Fpa-cyclo[DCys-Pal-DTrp-Lys-Ile-Cys]-Nal-NH$_2$ (PRL-2903); H-p-Chloro-DPhe-cyclo[DCys-Pal-Trp-Lys-Val-Cys]-2-Nal-NH$_2$ (BIM-23,627); H-Cpa-Cys-Pal-Trp-Lys-Val-Cys-Nal-NH$_2$ (BIM-23,454); Ac-4-NO$_2$-Phe-cyclo[D-Cys-Tyr-DTrp-Lys-Thr-Cys]-DTyr-NH$_2$ (D-Tyr8-CYN); Ac-4-NO$_2$-Phe-cyclo[Cys-Tyr-DTrp-Lys-Thr-Cys]-LTyr-NH$_2$ (L-Tyr8-CYN); H-Cpa-cyclo[Cys-Pal-DTrp-Lys-Ile-Cys]-Nal-NH$_2$ (PRL-2915); H-Cpa-cyclo[DCys-Tyr-DTrp-Lys-Thr-Cys]-Nal-NH$_2$ (PRL-2970)
H-Nal-cyclo[DCys-Pal-DTrp-Lys-Val-Cys]-Nal-NH$_2$ (DC-38-48)
DOTA-f-cyclo(CYwKTC)-TK (cypate)-NH$_2$ (LS172)
AcNH-4-NO$_2$-Phe-c[D-Cys-Tyr-D-Trp-Lys-Thr-Cys]-L-Tyr-NH$_2$ (L Cyanamid 154806)
AcNH-4-NO$_2$-Phe-c[D-Cys-Tyr-D-Trp-Lys-Thr-Cys]-D-Tyr-NH$_2$ (D Cyanamid 154806)
c[(R)-βMeNphe-Phe-DTrp-Lys-Thr-Phe]
Nal-cyclo[Cys-Thr-NMeLys-DTrp-Tyr-DCys]-Cpa-7-aminoheptanoic acid-Cpa-cyclo[DCys-Tyr-DTrp-NMeLys-Thr-Cys]-Nal-NH$_2$
H-Cpa-c[DCys-Aph(Cbm)-DTrp-Lys-Thr-Cys]-2Nal-NH$_2$; AcNH-4-NO$_2$-Phe-c[D-Cys-Tyr-D-Trp-Lys-Thr-Cys]-DTyr-NH$_2$; H-Cpa-c[DCys-LAgl(NMe,benzoyl)-DTrp-Lys-Thr-Cys]-2Nal-NH$_2$; H-Cpa-c[DCys-Tyr-DAph(Cbm)-Lys-Thr-Cys]-Nal-NH$_2$; DOTA-Cpa-c[DCys-Tyr-DAph(Cbm)-Lys-Thr-Cys]-Nal-NH$_2$; Cbm-Phe-c[DCys-Aph(Cbm)-DTrp-Lys-Thr-Cys]-Nal-NH$_2$; Cbm-Phe-c[DCys-Aph(Cbm)-DTrp-Lys-Thr-Cys]-Thr-NH$_2$

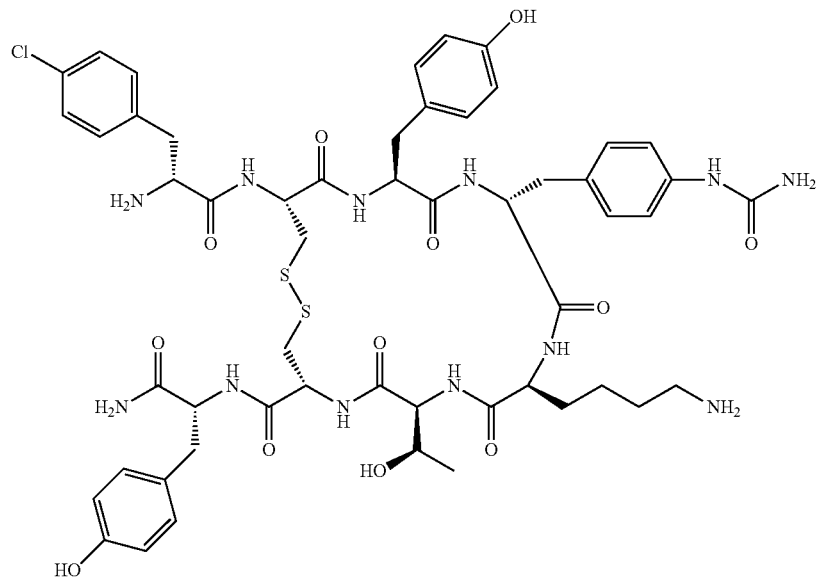 [SMILES: C[C@@H](O)[C@@H]1NC(=O)[C@H](CCCCN)NC(=O)[C@@H](Cc2ccc(NC(N)=O)cc2)NC(=O)[C@H](Cc2ccc(O)cc2)NC(=O)[C@@H](NC(=O)[C@H](N)Cc2ccc(Cl)cc2)CSSC[C@@H](C(=O)N[C@H](Cc2ccc(O)cc2)C(N)=O)NC1=O]

REFERENCES

AbdAlla, S., Lother, H., el Massiery, A., and Quitterer, U. (2001). Increased AT(1) receptor heterodimers in preeclampsia mediate enhanced angiotensin II responsiveness. Nat. Med. 7, 1003-1009.

Ahn, S., Shenoy, S. K., Wei, H., and Lefkowitz, R. J. (2004). Differential kinetic and spatial patterns of beta-arrestin and G protein-mediated ERK activation by the angiotensin II receptor. J Biol Chem 279, 35518-35525.

Albizu, L., Cottet, M., Kralikova, M., Stoev, S., Seyer, R., Brabet, I., Roux, T., Bazin, H., Bourrier, E., Lamarque, L., Breton, C., Rives, M. L., Newman, A., Javitch, J., Trinquet, E., Manning, M., Pin, J. P., Mouillac, B., and Durroux, T. (2010). Time-resolved FRET between GPCR ligands reveals oligomers in native tissues. Nat Chem Biol 6, 587-594.

Albizu, L., Holloway, T., Gonzalez-Maeso, J., and Sealfon, S. C. (2011). Functional crosstalk and heteromerization of serotonin 5-HT2A and dopamine D2 receptors. Neuropharmacology 61, 770-777.

Allavena, P., Garlanda, C., Borrello, M. G., Sica, A., and Mantovani, A. (2008). Pathways connecting inflammation and cancer. Current Opinion in Genetics & Development 18, 3-10.

Arumugam, T., Ramachandran, V., Fournier, K. F., Wang, H., Marquis, L., Abbruzzese, J. L., Gallick, G. E., Logsdon, C. D., McConkey, D. J., and Choi, W. (2009). Epithelial to mesenchymal transition contributes to drug resistance in pancreatic cancer. Cancer Res 69, 5820-5828.

Azdad, K., Gall, D., Woods, A. S., Ledent, C., Ferre, S., and Schiffmann, S. N. (2009). Dopamine D2 and adenosine A2A receptors regulate NMDA-mediated excitation in accumbens neurons through A2A-D2 receptor heteromerization. Neuropsychopharmacology 34, 972-986.

Balkwill, F. (2004). Cancer and the chemokine network. Nature reviews. Cancer 4, 540-550.

Belcheva, M. M., Szucs, M., Wang, D. X., Sadee, W., and Coscia, C. J. (2001). mu-opioid receptor-mediated ERK activation involves calmodulin-dependent epidermal growth factor receptor transactivation. J. Biol. Chem. 276, 33847-33853.

Belcheva, M. M., Tan, Y., Heaton, V. M., Clark, A. L., and Coscia, C. J. (2003). mu opioid transactivation and downregulation of the epidermal growth factor receptor in astrocytes: Implications for mitogen-activated protein kinase signaling. Mol. Pharmacol. 64, 1391-1401.

Berg, K. A., Rowan, M. P., Gupta, A., Sanchez, T. A., Silva, M., Gomes, I., McGuire, B. A., Portoghese, P. S., Hargreaves, K. M., Devi, L. A., and Clarke, W. P. (2012). Allosteric interactions between delta and kappa opioid receptors in peripheral sensory neurons. Mol Pharmacol 81, 264-272.

Berx, G., and van Roy, F. (2009). Involvement of members of the cadherin superfamily in cancer. Cold Spring Harbor perspectives in biology 1, a003129.

Betzig, E., Patterson, G. H., Sougrat, R., Lindwasser, O. W., Olenych, S., Bonifacino, J. S., Davidson, M. W., Lippincott-Schwartz, J., and Hess, H. F. (2006). Imaging intracellular fluorescent proteins at nanometer resolution. Science 313, 1642-1645.

Billadeau, D. D., Chatterjee, S., Bramati, P., Sreekumar, R., Shah, V., Hedin, K., and Urrutia, R. (2006). Characterization of the CXCR4 signaling in pancreatic cancer cells. International journal of gastrointestinal cancer 37, 110-119.

Bonni, A., Brunet, A., West, A. E., Datta, S. R., Takasu, M. A., and Greenberg, M. E. (1999). Cell survival promoted by the Ras-MAPK signaling pathway by transcription-dependent and -independent mechanisms. Science 286, 1358-1362.

Bushlin, I., Gupta, A., Stockton, S. D., Jr., Miller, L. K., and Devi, L. A. (2012). Dimerization with cannabinoid receptors allosterically modulates delta opioid receptor activity during neuropathic pain. PLoS One 7, e49789.

Call, T. R., Jedrzkiewicz, J., Tripp, S. R., Wilson, A. J., Chortkoff, B., and Witt, B. L. (2013). Mu Opioid Receptor Expression in Various Tumor Types: Creating a Mu Scoring System. In: American Society of Anesthesiologists (ASA) 2013 Annual Meeting, San Francisco, Calif., A4225.

Cascinu, S., Del Ferro, E., and Catalano, G. (1995). A randomised trial of octreotide vs best supportive care only in advanced gastrointestinal cancer patients refractory to chemotherapy. British journal of cancer 71, 97-101.

CCTU-Cancer Theme. To assess the safety of continuous IV administration of Plerixafor in patients with advanced pancratic, ovarian, and colorectal cancers (CAM-PLEX). In: ClinicalTrials.gov[Internet]. Bethesda (Md.): National Library of Medicine (US). 2000-[cited 2016 Sep. 26]. Available from: https://clinicaltrials.gov/show/NCT02179970 NLM Identified: NCT0217997.

Cervantes, D., Crosby, C., and Xiang, Y. (2010). Arrestin orchestrates crosstalk between G protein-coupled receptors to modulate the spatiotemporal activation of ERK MAPK. Circ Res 106, 79-88.

Chen, L., Fan, J., Chen, H., Meng, Z., Chen, Z., Wang, P., and Liu, L. (2014). The IL-8/CXCR1 axis is associated with cancer stem cell-like properties and correlates with clinical prognosis in human pancreatic cancer cases. Sci Rep 4, 5911.

Daniels, D. J., Lenard, N. R., Etienne, C. L., Law, P. Y., Roerig, S. C., and Portoghese, P. S. (2005). Opioid-induced tolerance and dependence in mice is modulated by the distance between pharmacophores in a bivalent ligand series. Proc Natl Acad Sci USA 102, 19208-19213.

Dempsey, G. T., Vaughan, J. C., Chen, K. H., Bates, M., and Zhuang, X. W. (2011). Evaluation of fluorophores for optimal performance in localization-based super-resolution imaging. Nat. Methods 8, 1027-1036.

Donaldson, J. M., Zer, C., Avery, K. N., Bzymek, K. P., Home, D. A., and Williams, J. C. (2013). Identification and grafting of a unique peptide-binding site in the Fab framework of monoclonal antibodies. Proc Natl Acad Sci USA 110, 17456-17461.

Dudok, B., Barna, L., Ledri, M., Szabo, S. I., Szabadits, E., Pinter, B., Woodhams, S. G., Henstridge, C. M., Balla, G. Y., Nyilas, R., Varga, C., Lee, S. H., Matolcsi, M., Cervenak, J., Kacskovics, I., Watanabe, M., Sagheddu, C., *Melis*, M., Pistis, M., Soltesz, I., and Katona, I. (2015). Cell-specific STORM super-resolution imaging reveals nanoscale organization of cannabinoid signaling. Nature neuroscience 18, 75-86.

Dutruel, C., Bergmann, F., Rooman, I., Zucknick, M., Weichenhan, D., Geiselhart, L., Kaffenberger, T., Rachakonda, P. S., Bauer, A., Giese, N., Hong, C., Xie, H., Costello, J. F., Hoheisel, J., Kumar, R., Rehli, M., Schirmacher, P., Werner, J., Plass, C., Popanda, O., and Schmezer, P. (2014). Early epigenetic downregulation of WNK2 kinase during pancreatic ductal adenocarcinoma development. Oncogene 33, 3401-3410.

Ferre, S., Baler, R., Bouvier, M., Caron, M. G., Devi, L. A., Durroux, T., Fuxe, K., George, S. R., Javitch, J. A., Lohse, M. J., Mackie, K., Milligan, G., Pfleger, K. D. G., Pin, J.-P., Volkow, N. D., Waldhoer, M., Woods, A. S., and Franco, R. (2009). Building a new conceptual framework for receptor heteromers. Nat. Chem. Biol. 5, 131-134.

Finley, M. J., Chen, X., Bardi, G., Davey, P., Geller, E. B., Zhang, L., Adler, M. W., and Rogers, T. J. (2008). Bi-directional heterologous desensitization between the major HIV-1 co-receptor CXCR4 and the kappa-opioid receptor. J Neuroimmunol 197, 114-123.

Folling, J., Bossi, M., Bock, H., Medda, R., Wurm, C. A., Hein, B., Jakobs, S., Eggeling, C., and Hell, S. W. (2008). Fluorescence nanoscopy by ground-state depletion and single-molecule return. Nat. Methods 5, 943-945.

H. Lee Moffitt Cancer Center and Research Insitute. SOM 230 and Gemcitabine in advanced pancreatic cancer. In: ClinicalTrials.gov[Internet]. Bethesda (Md.): National Library of Medicine (US). 2000—[cited 2016 Sep. 26]. Available from: http://clinicaltrials.gov/show/NCT01385956 NLM Identifier: NCT01385956.

Fujioka, N., Nguyen, J., Chen, C. S., Li, Y. F., Pasrija, T., Niehans, G., Johnson, K. N., Gupta, V., Kratzke, R. A., and Gupta, K. (2011). Morphine-Induced Epidermal Growth Factor Pathway Activation in Non-Small Cell Lung Cancer. Anesthesia and Analgesia 113, 1353-1364.

Gesty-Palmer, D., Chen, M., Reiter, E., Ahn, S., Nelson, C. D., Wang, S., Eckhardt, A. E., Cowan, C. L., Spurney, R. F., Luttrell, L. M., and Lefkowitz, R. J. (2006). Distinct beta-arrestin- and G protein-dependent pathways for parathyroid hormone receptor-stimulated ERK1/2 activation. J Biol Chem 281, 10856-10864.

Gomes, I., Ayoub, M. A., Fujita, W., Jaeger, W. C., Pfleger, K. D., and Devi, L. A. (2016). G Protein-Coupled Receptor Heteromers. Annu Rev Pharmacol Toxicol 56, 403-425.

Gomes, I., Fujita, W., Chandrakala, M. V., and Devi, L. A. (2013). Disease-specific heteromerization of G-protein-coupled receptors that target drugs of abuse. Progress in molecular biology and translational science 117, 207-265.

Gomes, I., Gupta, A., Filipovska, J., Szeto, H. H., Pintar, J. E., and Devi, L. A. (2004). A role for heterodimerization of mu and delta opiate receptors in enhancing morphine analgesia. Proc Natl Acad Sci USA 101, 5135-5139.

Gradiz, R., Silva, H. C., Carvalho, L., Botelho, M. F., and Mota-Pinto, A. (2016). MIA PaCa-2 and PANC-1—pancreas ductal adenocarcinoma cell lines with neuroendocrine differentiation and somatostatin receptors. Sci Rep 6, 21648.

Grant, M., Alturaihi, H., Jaquet, P., Collier, B., and Kumar, U. (2008). Cell growth inhibition and functioning of human somatostatin receptor type 2 are modulated by receptor heterodimerization. Molecular endocrinology (Baltimore, Md.) 22, 2278-2292.

Gupta, A., Mulder, J., Gomes, I., Rozenfeld, R., Bushlin, I., Ong, E., Lim, M., Maillet, E., Junek, M., Cahill, C. M., Harkany, T., and Devi, L. A. (2010). Increased abundance of opioid receptor heteromers after chronic morphine administration. Sci Signal 3, ra54.

Hanahan, D., and Weinberg, R. A. (2011). Hallmarks of Cancer: The Next Generation. Cell 144, 646-674.

Handra-Luca, A., Hong, S. M., Walter, K., Wolfgang, C., Hruban, R., and Goggins, M. (2011). Tumour epithelial vimentin expression and outcome of pancreatic ductal adenocarcinomas. British journal of cancer 104, 1296-1302.

Heasley, L. E. (2001). Autocrine and paracrine signaling through neuropeptide receptors in human cancer. Oncogene 20, 1563-1569.

Hess, S. T., Girirajan, T. P. K., and Mason, M. D. (2006). Ultra-high resolution imaging by fluorescence photoactivation localization microscopy. Biophys. J. 91, 4258-4272.

Hirschhaeuser, F., Menne, H., Dittfeld, C., West, J., Mueller-Klieser, W., and Kunz-Schughart, L. A. (2010). Multicellular tumor spheroids: an underestimated tool is catching up again. J Biotechnol 148, 3-15.

Howlader N, N. A., Krapcho M, Garshell J, Neyman N, Altekruse S F, Kosary C L, Yu M, Ruhl J, Tatalovich Z, Cho H, Mariotto A, Lewis D R, Chen H S, Feuer E J, Cronin K A (eds). (2014). SEER Cancer Statistics Review, 1975-2011, National Cancer Institute. Bethesda, Md. Based on November 2013 SEER data submission, posted to the SEER web site, April 2014.

Jaquet, P., Gunz, G., Saveanu, A., Dufour, H., Taylor, J., Dong, J., Kim, S., Moreau, J. P., Enjalbert, A., and Culler, M. D. (2005). Efficacy of chimeric molecules directed towards multiple somatostatin and dopamine receptors on inhibition of GH and prolactin secretion from GH-secreting pituitary adenomas classified as partially responsive to somatostatin analog therapy. European journal of endocrinology/European Federation of Endocrine Societies 153, 135-141.

Javle, M. M., Gibbs, J. F., Iwata, K. K., Pak, Y., Rutledge, P., Yu, J., Black, J. D., Tan, D., and Khoury, T. (2007). Epithelial-mesenchymal transition (EMT) and activated extracellular signal-regulated kinase (p-Erk) in surgically resected pancreatic cancer. Annals of surgical oncology 14, 3527-3533.

Jiang, J. H., Liu, C., Cheng, H., Lu, Y., Qin, Y., Xu, Y. F., Xu, J., Long, J., Liu, L., Ni, Q. X., and Yu, X. J. (2015). Epithelial-mesenchymal transition in pancreatic cancer: Is it a clinically significant factor? Biochimica et biophysica acta 1855, 43-49.

Jonas, K. C., Fanelli, F., Huhtaniemi, I. T., and Hanyaloglu, A. C. (2015). Single Molecule Analysis of Functionally Asymmetric GPCR Oligomers reveals Diverse Spatial and Structural Assemblies. J Biol Chem 290, 3875-3892.

Jones, L. E., Humphreys, M. J., Campbell, F., Neoptolemos, J. P., and Boyd, M. T. (2004). Comprehensive analysis of matrix metalloproteinase and tissue inhibitor expression in pancreatic cancer: increased expression of matrix metalloproteinase-7 predicts poor survival. Clinical cancer research: an official journal of the American Association for Cancer Research 10, 2832-2845.

Kailey, B., van de Bunt, M., Cheley, S., Johnson, P. R., MacDonald, P. E., Gloyn, A. L., Rorsman, P., and Braun, M. (2012). SSTR2 is the functionally dominant somatostatin receptor in human pancreatic beta- and alpha-cells. American journal of physiology. Endocrinology and metabolism 303, E1107-1116.

Kan, Z., Jaiswal, B. S., Stinson, J., Janakiraman, V., Bhatt, D., Stern, H. M., Yue, P., Haverty, P. M., Bourgon, R., Zheng, J., Moorhead, M., Chaudhuri, S., Tomsho, L. P., Peters, B. A., Pujara, K., Cordes, S., Davis, D. P., Carlton, V. E., Yuan, W., Li, L., Wang, W., Eigenbrot, C., Kaminker, J. S., Eberhard, D. A., Waring, P., Schuster, S. C., Modrusan, Z., Zhang, Z., Stokoe, D., de Sauvage, F. J., Faham, M., and Seshagiri, S. (2010). Diverse somatic mutation patterns and pathway alterations in human cancers. Nature 466, 869-873.

Kenakin, T. (2011). Functional selectivity and biased receptor signaling. The Journal of pharmacology and experimental therapeutics 336, 296-302.

Kharmate, G., Rajput, P. S., Lin, Y. C., and Kumar, U. (2013). Inhibition of tumor promoting signals by activation of SSTR2 and opioid receptors in human breast cancer cells. Cancer Cell International 13.

Kleeff, J., Beckhove, P., Esposito, I., Herzig, S., Huber, P. E., Lohr, J. M., and Friess, H. (2007). Pancreatic cancer microenvironment. International journal of cancer 121, 699-705.

Korc, M., Chandrasekar, B., Yamanaka, Y., Friess, H., Buchier, M., and Beger, H. G. (1992). Overexpression of the epidermal growth factor receptor in human pancreatic cancer is associated with concomitant increases in the levels of epidermal growth factor and transforming growth factor alpha. J Clin Invest 90, 1352-1360.

Koshiba, T., Hosotani, R., Miyamoto, Y., Ida, J., Tsuji, S., Nakajima, S., Kawaguchi, M., Kobayashi, H., Doi, R., Hori, T., Fujii, N., and Imamura, M. (2000). Expression of stromal cell-derived factor 1 and CXCR4 ligand receptor system in pancreatic cancer: a possible role for tumor progression. Clinical cancer research: an official journal of the American Association for Cancer Research 6, 3530-3535.

Kuszak, A. J., Pitchiaya, S., Anand, J. P., Mosberg, H. I., Walter, N. G., and Sunahara, R. K. (2009). Purification and functional reconstitution of monomeric mu-opioid receptors: allosteric modulation of agonist binding by Gi2. J Biol Chem 284, 26732-26741.

Laklai, H., Laval, S., Dumartin, L., Rochaix, P., Hagedorn, M., Bikfalvi, A., Le Guellec, S., Delisle, M. B., Schally, A. V., Susini, C., Pyronnet, S., and Bousquet, C. (2009). Thrombospondin-1 is a critical effector of oncosuppressive activity of sst2 somatostatin receptor on pancreatic cancer. Proc Natl Acad Sci USA 106, 17769-17774.

Levet, F., Hosy, E., Kechkar, A., Butler, C., Beghin, A., Choquet, D., and Sibarita, J. B. (2015). SR-Tesseler: a method to segment and quantify localization-based super-resolution microscopy data. Nat Methods 12, 1065-1071.

Lewis, S. M., Wu, X., Pustilnik, A., Sereno, A., Huang, F., Rick, H. L., Guntas, G., Leaver-Fay, A., Smith, E. M., Ho, C., Hansen-Estruch, C., Chamberlain, A. K., Truhlar, S. M., Conner, E. M., Atwell, S., Kuhlman, B., and Demarest, S. J. (2014). Generation of bispecific IgG antibodies by structure-based design of an orthogonal Fab interface. Nat Biotechnol 32, 191-198.

Li, D., Xie, K., Wolff, R., and Abbruzzese, J. L. (2004a). Pancreatic cancer. Lancet 363, 1049-1057.

Li, M., Li, W., Kim, H. J., Yao, Q., Chen, C., and Fisher, W. E. (2004b). Characterization of somatostatin receptor expression in human pancreatic cancer using real-time RT-PCR. The Journal of surgical research 119, 130-137.

Lieber, M., Mazzetta, J., Nelson-Rees, W., Kaplan, M., and Todaro, G. (1975). Establishment of a continuous tumor-cell line (panc-1) from a human carcinoma of the exocrine pancreas. International journal of cancer. Journal international du cancer 15, 741-747.

Marshall, C. J. (1995). Specificity of receptor tyrosine kinase signaling: transient versus sustained extracellular signal-regulated kinase activation. Cell 80, 179-185.

Melchiorri, P., and Negri, L. (1996). The dermorphin peptide family. General pharmacology 27, 1099-1107.

M. D. Anderson Cancer Center. Dasatinib. Bevacizumab, Paclitaxel in patients with advanced malignancies. In: ClinicalTrials.gov [Internet]. Bethesda (Md.): National Library of Medicine (US). 2000—[cited 2016 Sep. 26]. Available from: http://clinicaltrials.gov/show/NCT01015222 NLM Identifier: NCT01015222.

Mercadante, S., Tirelli, W., David, F., Arcara, C., Fulfaro, F., Casuccio, A., and Gebbia, V. (2010). Morphine versus oxycodone in pancreatic cancer pain: a randomized controlled study. The Clinical journal of pain 26, 794-797.

Moll, R., Franke, W. W., Schiller, D. L., Geiger, B., and Krepler, R. (1982). The catalog of human cytokeratins: patterns of expression in normal epithelia, tumors and cultured cells. Cell 31, 11-24.

Moore, M. J., Goldstein, D., Hamm, J., Figer, A., Hecht, J. R., Gallinger, S., Au, H. J., Murawa, P., Walde, D., Wolff, R. A., Campos, D., Lim, R., Ding, K., Clark, G., Voskoglou-Nomikos, T., Ptasynski, M., and Parulekar, W. (2007). Erlotinib plus gemcitabine compared with gemcitabine alone in patients with advanced pancreatic cancer: a phase III trial of the National Cancer Institute of Canada Clinical Trials Group. Journal of clinical oncology: official journal of the American Society of Clinical Oncology 25, 1960-1966.

Moreno, E., Andradas, C., Medrano, M., Caffarel, M. M., Perez-Gomez, E., Blasco-Benito, S., Gomez-Canas, M., Pazos, M. R., Irving, A. J., Lluis, C., Canela, E. I., Fernandez-Ruiz, J., Guzman, M., McCormick, P. J., and Sanchez, C. (2014). Targeting CB2-GPR55 receptor heteromers modulates cancer cell signaling. J Biol Chem 289, 21960-21972.

Nakajima, S., Doi, R., Toyoda, E., Tsuji, S., Wada, M., Koizumi, M., Tulachan, S. S., Ito, D., Kami, K., Mori, T., Kawaguchi, Y., Fujimoto, K., Hosotani, R., and Imamura, M. (2004). N-cadherin expression and epithelial-mesenchymal transition in pancreatic carcinoma. Clinical cancer research: an official journal of the American Association for Cancer Research 10, 4125-4133.

Oberstein, P. E., and Olive, K. P. (2013). Pancreatic cancer: why is it so hard to treat? Therapeutic advances in gastroenterology 6, 321-337.

Pello, O. M., Martinez-Munoz, L., Parrillas, V., Serrano, A., Rodriguez-Frade, J. M., Toro, M. J., Lucas, P., Monterrubio, M., Martinez, A. C., and Mellado, M. (2008). Ligand stabilization of CXCR4/delta-opioid receptor heterodimers reveals a mechanism for immune response regulation. European journal of immunology 38, 537-549.

Pfeiffer, M., Koch, T., Schroder, H., Laugsch, M., Hollt, V., and Schulz, S. (2002). Heterodimerization of somatostatin and opioid receptors cross-modulates phosphorylation, internalization, and desensitization. J Biol Chem 277, 19762-19772.

Pham, N. A., Schwock, J., Iakovlev, V., Pond, G., Hedley, D. W., and Tsao, M. S. (2008). Immunohistochemical analysis of changes in signaling pathway activation downstream of growth factor receptors in pancreatic duct cell carcinogenesis. BMC Cancer 8, 43.

Reubi, J. C., Waser, B., Friess, H., Buchler, M., and Laissue, J. (1998). Neurotensin receptors: a new marker for human ductal pancreatic adenocarcinoma. Gut 42, 546-550.

Rozenfeld, R., and Devi, L. A. (2007). Receptor heterodimerization leads to a switch in signaling: beta-arrestin2-mediated ERK activation by mu-delta opioid receptor heterodimers. FASEB journal: official publication of the Federation of American Societies for Experimental Biology 21, 2455-2465.

Rozenfeld, R., Gupta, A., Gagnidze, K., Lim, M. P., Gomes, I., Lee-Ramos, D., Nieto, N., and Devi, L. A. (2011). AT1R-CB(1)R heteromerization reveals a new mechanism for the pathogenic properties of angiotensin II. EMBO J 30, 2350-2363.

Rust, M. J., Bates, M., and Zhuang, X. W. (2006). Sub-diffraction-limit imaging by stochastic optical reconstruction microscopy (STORM). Nat. Methods 3, 793-795.

Sams, M., Silye, R., Gohring, J., Muresan, L., Schilcher, K., and Jacak, J. (2014). Spatial cluster analysis of nanoscopically mapped serotonin receptors for classification of fixed brain tissue. Journal of biomedical optics 19, 011021.

Scarselli, M., Annibale, P., and Radenovic, A. (2012). Cell-type-specific (32 adrenergic receptor clusters identified using photo-activated localization microscopy are not lipid raft related, but depend on actin cytoskeleton integrity. The Journal of Biological chemistry 287, 16768-16780.

Schmid, C. L., and Bohn, L. M. (2009). Physiological and pharmacological implications of beta-arrestin regulation. Pharmacol Ther 121, 285-293.

Sengupta, P., Jovanovic-Talisman, T., and Lippincott-Schwartz, J. (2013). Quantifying spatial organization in point-localization superresolution images using pair correlation analysis. Nature Protocols 8, 345-354.

Sengupta, P., Jovanovic-Talisman, T., Skoko, D., Renz, M., Veatch, S. L., and Lippincott-Schwartz, J. (2011). Probing protein heterogeneity in the plasma membrane using PALM and pair correlation analysis. Nat. Methods 8, 969-975.

Shahbaz, M., Ruliang, F., Xu, Z., Benjia, L., Cong, W., Zhaobin, H., and Jun, N. (2015). mRNA expression of somatostatin receptor subtypes SSTR-2, SSTR-3, and SSTR-5 and its significance in pancreatic cancer. World journal of surgical oncology 13, 46.

Shenoy, S. K., Drake, M. T., Nelson, C. D., Houtz, D. A., Xiao, K., Madabushi, S., Reiter, E., Premont, R. T., Lichtarge, O., and Lefkowitz, R. J. (2006). beta-arrestindependent, G protein-independent ERK1/2 activation by the beta2 adrenergic receptor. J Biol Chem 281, 1261-1273.

Singh, S., Srivastava, S. K., Bhardwaj, A., Owen, L. B., and Singh, A. P. (2010). CXCL12-CXCR4 signalling axis confers gemcitabine resistance to pancreatic cancer cells: a novel target for therapy. British journal of cancer 103, 1671-1679.

Singleton, P. A., Mirzapoiazova, T., Hasina, R., Salgia, R., and Moss, J. (2014). Increased mu-opioid receptor expression in metastatic lung cancer. Br J Anaesth.

Smith, E. R., Smedberg, J. L., Rula, M. E., and Xu, X. X. (2004). Regulation of Ras-MAPK pathway mitogenic activity by restricting nuclear entry of activated MAPK in endoderm differentiation of embryonic carcinoma and stem cells. J Cell Biol 164, 689-699.

Soria, G., and Ben-Baruch, A. (2009). The CCL5/CCR5 Axis in Cancer. In: Chemokine Receptors in Cancer, ed. A. M. Fulton: Humana Press, 109-130.

Stone, M. B., and Veatch, S. L. (2015). Steady-state cross-correlations for live two-colour super-resolution localization data sets. Nature communications 6, 7347.

Sutherland, R. M. (1988). Cell and environment interactions in tumor microregions: the multicell spheroid model. Science 240, 177-184.

Szende, B., Srkalovic, G., Schally, A. V., Lapis, K., and Groot, K. (1990). Inhibitory effects of analogs of luteinizing hormone-releasing hormone and somatostatin on pancreatic cancers in hamsters. Events that accompany tumor regression. Cancer 65, 2279-2290.

Tobin, S. J., Cacao, E. E., Hong, D. W., Terenius, L., Vukojevic, V., and Jovanovic-Talisman, T. (2014). Nanoscale effects of ethanol and naltrexone on protein organization in the plasma membrane studied by photoactivated localization microscopy (PALM). PLoS One 9, e87225.

Von Hoff, D. D., Ervin, T., Arena, F. P., Chiorean, E. G., Infante, J., Moore, M., Seay, T., Tjulandin, S. A., Ma, W. W., Saleh, M. N., Harris, M., Reni, M., Dowden, S., Laheru, D., Bahary, N., Ramanathan, R. K., Tabernero, J., Hidalgo, M., Goldstein, D., Van Cutsem, E., Wei, X., Iglesias, J., and Renschler, M. F. (2013). Increased survival in pancreatic cancer with nab-paclitaxel plus gemcitabine. The New England journal of medicine 369, 1691-1703.

Wang, D., Sun, X., Bohn, L. M., and Sadee, W. (2005). Opioid receptor homo- and heterodimerization in living cells by quantitative bioluminescence resonance energy transfer. Mol Pharmacol 67, 2173-2184.

Wang, R. et al. Gemcitabine resistance is associated with epithelial-mesenchymal transition and induction of HIF-1alpha in pancreatic cancer cells. Current cancer drug targets 14, 407-417 (2014).

Wang, Z., Li, Y., Kong, D., Banerjee, S., Ahmad, A., Azmi, A. S., Ali, S., Abbruzzese, J. L., Gallick, G. E., and Sarkar, F. H. (2009). Acquisition of epithelial-mesenchymal transition phenotype of gemcitabine-resistant pancreatic cancer cells is linked with activation of the notch signaling pathway. Cancer Res 69, 2400-2407.

Whorton, M. R., Bokoch, M. P., Rasmussen, S. G., Huang, B., Zare, R. N., Kobilka, B., and Sunahara, R. K. (2007). A monomeric G protein-coupled receptor isolated in a high-density lipoprotein particle efficiently activates its G protein. Proc Natl Acad Sci USA 104, 7682-7687.

Wombacher, R., Heidbreder, M., van de Linde, S., Sheetz, M. P., Heilemann, M., Cornish, V. W., and Sauer, M. (2010). Live-cell super-resolution imaging with trimethoprim conjugates. Nat. Methods 7, 717-719.

Yoon, S., and Seger, R. (2006). The extracellular signal-regulated kinase: multiple substrates regulate diverse cellular functions. Growth Factors 24, 21-44.

Yuan, Y., Arnatt, C. K., El-Hage, N., Dever, S. M., Jacob, J. C., Selley, D. E., Hauser, K. F., and Zhang, Y. (2013). A Bivalent Ligand Targeting the Putative Mu Opioid Receptor and Chemokine Receptor CCR5 Heterodimers: Binding Affinity versus Functional Activities. Medicinal Chemistry Communications 4, 847-851.

Zhang, Y., Wei, J., Wang, H., Xue, X., An, Y., Tang, D., Yuan, Z., Wang, F., Wu, J., Zhang, J., and Miao, Y. (2012). Epithelial mesenchymal transition correlates with CD24+ CD44+ and CD133+ cells in pancreatic cancer. Oncology reports 27, 1599-1605.

Zheng, X. et al. Epithelial-to-mesenchymal transition is dispensable for metastasis but induces chemoresistance in pancreatic cancer. Nature 527, 525-530 (2015).

Zylla, D., Gourley, B. L., Vang, D., Jackson, S., Boatman, S., Lindgren, B., Kuskowski, M. A., Le, C., Gupta, K., and Gupta, P. (2013). Opioid Requirement, Opioid Receptor Expression, and Clinical Outcomes in Patients With Advanced Prostate Cancer. Cancer 119, 4103-4110.

Informal Sequence Listing

Abbreviations. Chemical abbreviations disclosed herein have the following meanings. "DOTA" refers, in the usual and customary sense, to 1,4,7,10-tetraazacyclododecane-1, 4,7,10-tetraacetic acid. "Cbm" refers, in the usual and customary sense, to carbamoyl. "Aph" refers, in the usual and customary sense, to (2-,3- or 4-amino)phenylalanine, e.g., 2-aminophenylalanine, 3-aminophenylalanine, or 4-aminophenylalanine. "Pal" refers, in the usual and customary sense, to β-(2-,3- or 4-pyridyl)alanine, e.g., β-(2-pyridyl)alanine, β-(3-pyridyl)alanine, or β-(4-pyridyl)alanine. "Nal" refers, in the usual and customary sense, to b-(1- or 2-naphthyl)alanine, e.g., b-(1-naphthyl)alanine or b-(2-naphthyl)alanine.

---

INFORMAL SEQUENCE LISTING

Mu-type opioid receptor (Homo sapiens):
(Uniprot P35372.2, SEQ ID NO: 1)
MDSSAAPTNASNCTDALAYSSCSPAPSPGSWVNLSHLDGNLSDPCGP

NRTDLGGRDSLCPPTGSPSMITAITIMALYSIVCVVGLFGNFLVMYV

IVRYTKMKTATNIYIFNLALADALATSTLPFQSVNYLMGTWPFGTIL

CKIVISIDYYNMFTSIFTLCTMSVDRYIAVCHPVKALDFRTPRNAKI

INVCNWILSSAIGLPVMFMATTKYRQGSIDCTLTFSHPTWYWENLLK

ICVFIFAFIMPVLIITVCYGLMILRLKSVRMLSGSKEKDRNLRRITR

MVLVVVAVFIVCWTPIHIYVIIKALVTIPETTFQTVSWHFCIALGYT

NSCLNPVLYAFLDENFKRCFREFCIPTSSNIEQQNSTRIRQNTRDHP

STANTVDRTNHQLENLEAETAPLP

Somatostatin receptor type 2 (Homo sapiens):
(Uniprot P30874.1, SEQ ID NO: 2)
MDMADEPLNGSHTWLSIPFDLNGSVVSTNTSNQTEPYYDLTSNAVLT

FIYFVVCIIGLCGNTLVIYVILRYAKMKTITNIYILNLAIADELFML

GLPFLAMQVALVHWPFGKAICRVVMTVDGINQFTSIFCLTVMSIDRY

LAVVHPIKSAKWRRPRTAKMITMAVWGVSLLVILPIMIYAGLRSNQW

INFORMAL SEQUENCE LISTING

GRSSCTINWPGESGAWYTGFIIYTFILGFLVPLTIICLCYLFIIIKV
KSSGIRVGSSKRKKSEKKVTRMVSIVVAVFIFCWLPFYIFNVSSVSM
AISPTPALKGMFDFVVVLTYANSCANPILYAFLSDNFKKSFQNVLCL
VKVSGTDDGERSDSKQDKSRLNETTETQRTLLNGDLQTSI.

(SEQ ID NO: 3)
MDSSAAPTNASNCTDALAYSSCSPAPSPGSWVNLSHLDGNLSDPCGP
NRTDLGGRDSLCP.

(SEQ ID NO: 4)
MDMADEPLNGSHTWLSIPFDLNGSVVSTNTSNQTEP.

(SEQ ID NO: 5)
MEGISIYTSDNYTEEMGSGDYDSMKEPCFREENAN.

(SEQ ID NO: 6)
FCIPTSSNIEQQNSTRIRQNTRDHPSTANTVDRTNHQLENLEAETAP
LP.

(SEQ ID NO: 7)
LCLVKVSGTDDGERSDSKQDKSRLNETTETQRTLLNGDLQTSI.

(SEQ ID NO: 8)
LTSVSRGSSLKILSKGKRGGHSSVSTESESSSFHSS

P EMBODIMENTS

Embodiment 1

A G protein-coupled receptor (GPCR)-ligand conjugate comprising: (i) a Mu opoid receptor (MOR) polypeptide bound to a MOR antagonist; and (ii) a somatostatin receptor 2 (SSTR2) polypeptide bound to a SSTR2 antagonist; wherein said MOR polypeptide and said SSTR2 polypeptide are bound together.

Embodiment 2

The conjugate of embodiment 1, wherein said MOR polypeptide comprises the sequence of SEQ ID NO:1.

Embodiment 3

The conjugate of embodiment 1 or 2, wherein said SSTR2 polypeptide comprises the sequence of SEQ ID NO:2.

Embodiment 4

The conjugate of one of embodiments 1-3, wherein said MOR polypeptide is the sequence of SEQ ID NO:1.

Embodiment 5

The conjugate of one of embodiments 1-4, wherein said SSTR2 polypeptide is the sequence of SEQ ID NO:2.

Embodiment 6

The conjugate of one of embodiments 1-5, wherein said MOR antagonist is a small molecule or a peptide.

Embodiment 7

The conjugate of one of embodiments 1-6, wherein said MOR antagonist is a small molecule.

Embodiment 8

The conjugate of one of embodiments 1-7, wherein said MOR antagonist is [3H]diprenorphine, [3H]naloxone, naloxonazine, diprenorphine, quadazocine, naltrexone, nalmefene, alvimopan, diprenorphine, levallorphan, naloxone, nalorphine, BNTX, AT-076, methylnaltrexone, CTAP, naloxone benzoylhydrazone, naltrindole, naltriben, nor-binaltorphimine, LY2456302 or zyklophin.

Embodiment 9

The conjugate of one of embodiments 1-8, wherein said MOR antagonist is methylnaltrexone.

Embodiment 10

The conjugate of one of embodiments 1-9, wherein said SSTR2 antagonist is a small molecule or a peptide.

Embodiment 11

The conjugate of one of embodiments 1-10, wherein said SSTR2 antagonist is a small molecule.

Embodiment 12

The conjugate of one of embodiments 1-10, wherein said SSTR2 antagonist is a peptide.

Embodiment 13

The conjugate of one of embodiments 1-10 or 12, wherein said SSTR2 antagonist is a peptide of formula (cyclo 3-14) DOTA-pNO$_2$-Phe-cyclo[DCys-Tyr-D-4Aph(Cbm)-Lys-Thr-Cys]-DTyr-NH2 or NH2-pNO2-Phe-cyclo[DCys-Tyr-D-4Aph(Cbm)-Lys-Thr-Cys]-DTyr-NH$_2$.

Embodiment 14

The conjugate of one of embodiments 1-13, wherein said conjugate forms part of a cell.

Embodiment 15

The conjugate of one of embodiments 1-14, wherein said conjugate forms part of a cell membrane.

Embodiment 16

The conjugate of one of embodiments 1-14, wherein said conjugate forms part of a lipid raft.

Embodiment 17

The conjugate of one of embodiments 1-14, wherein said conjugate forms part of a cytoplasm.

Embodiment 18

The conjugate of embodiments 15-17, wherein said cell is a cancer cell.

Embodiment 19

The conjugate of embodiment 18, wherein said cell is a pancreatic cancer cell.

Embodiment 20

The conjugate of embodiment 18 or 19, wherein said cell is a pancreatic ductal adenocarcinoma cell.

Embodiment 21

A method of treating pancreatic cancer in a subject in need thereof, said method comprising administering to a subject a therapeutically effective amount of a SSTR2 antagonist, thereby treating pancreatic cancer in said subject.

Embodiment 22

The method of embodiment 21, further comprising administering to said subject a therapeutically effective amount of an anti-cancer agent.

Embodiment 23

The method of embodiment 21 or 22, further comprising administering to said subject a therapeutically effective amount of a MOR antagonist.

Embodiment 24

The method of embodiment 23, wherein said MOR antagonist is a small molecule.

Embodiment 25

The method of embodiment 23 or 24, wherein said MOR antagonist is [3H]diprenorphine, [3H]naloxone, naloxonazine, diprenorphine, quadazocine, naltrexone, nalmefene, alvimopan, diprenorphine, levallorphan, nalorphine, naloxone, BNTX, AT-076, methylnaltrexone, CTAP, naloxone benzoylhydrazone, naltrindole, naltriben, nor-binaltorphimine, LY2456302 or zyklophin.

Embodiment 26

The method of one of embodiments 23-25, wherein said MOR antagonist is methylnaltrexone.

Embodiment 27

The method of one of embodiments 21-26, wherein said SSTR2 antagonist is a small molecule or a peptide.

Embodiment 28

The method of one of embodiments 21-27, wherein said SSTR2 antagonist is a small molecule.

Embodiment 29

The method of one of embodiments 21-27, wherein said SSTR2 antagonist is a peptide.

Embodiment 30

The method of one of embodiments 21-27 or 29, wherein said SSTR2 antagonist is a peptide of formula (cyclo 3-14) DOTA-pNO2-Phe-cyclo[DCys-Tyr-D-4Aph(Cbm)-Lys-Thr-Cys]-DTyr-NH2 or NH2-pNO2-Phe-cyclo[DCys-Tyr-D-4Aph(Cbm)-Lys-Thr-Cys]-DTyr-NH2.

Embodiment 31

The method of one of embodiments 21-30, wherein said SSTR2 antagonist binds a SSTR2 polypeptide in said subject and wherein said SSTR2 polypeptide is bound to a MOR polypeptide.

Embodiment 32

The method of one of embodiments 23-31, wherein said MOR antagonist binds a MOR polypeptide in said subject and wherein said MOR polypeptide is bound to a SSTR2 polypeptide.

Embodiment 33

A method of inhibiting metastasis in a subject in need thereof, said method comprising administering to a subject a therapeutically effective amount of a SSTR2 antagonist, thereby inhibiting metastasis in said subject.

Embodiment 34

The method of embodiment 33, further comprising administering to said subject a therapeutically effective amount of a MOR antagonist.

Embodiment 35

The method of embodiment 33 or 34, wherein said subject suffers from pancreatic cancer.

---

What is claimed is:

1. A method of treating pancreatic cancer in a subject in need thereof, said method comprising administering to a subject a therapeutically effective amount of a somatostatin receptor 2 (SSTR2) antagonist and a therapeutically effective amount of a μ-opioid receptor (MOR) antagonist, thereby treating pancreatic cancer in said subject, wherein said pancreatic cancer is an exocrine pancreatic cancer, wherein said MOR antagonist is naloxonazine, quadazocine, naltrexone, nalmefene, alvimopan, levallorphan, naloxone, AT-076, methylnaltrexone, D-Phe-Cys-Tyr-D-Trp-Arg-Thr-Pen-Thr-NH$_2$, naltriben, or 4-[4-[[(2S)-2-(3,5-dimethylphenyl)pyrrolidin-1-yl]methyl]phenoxy]-3-fluorobenzamide; and wherein said SSTR2 antagonist is a peptide of (cyclo 3-14)DOTA-pNO2-Phe-cyclo[D-Cys-Tyr-D-4Aph(Cbm)-Lys-Thr-Cys]-D-Tyr-NH2 or NH2-pNO2-Phe-cyclo[D-Cys-Tyr-D-4Aph(Cbm)-Lys-Thr-Cys]-D-Tyr-N H2.

2. The method of claim 1, wherein the effective amount of a SSTR2 antagonist and the effective amount of a MOR antagonist are a combined synergistic amount.

3. The method of claim 1, wherein said SSTR2 antagonist and said MOR antagonist are administered sequentially or concurrently.

4. The method of claim 1, wherein said MOR antagonist is methylnaltrexone.

5. The method of claim 1, wherein said MOR antagonist is methylnaltrexone and said SSTR2 antagonist is the compound BIM-23627.

6. The method of claim 1, wherein said SSTR2 antagonist binds a SSTR2 polypeptide in said subject and wherein said SSTR2 polypeptide is bound to a MOR polypeptide.

7. The method of claim 1, wherein said MOR antagonist binds a MOR polypeptide in said subject and wherein said MOR polypeptide is bound to a SSTR2 polypeptide.

8. The method of claim 1, wherein said exocrine pancreatic cancer is a pancreatic ductal adenocarcinoma (PDAC).

* * * * *

SEQUENCE LISTING

```
<160> NUMBER OF SEQ ID NOS: 28

<210> SEQ ID NO 1
<211> LENGTH: 400
<212> TYPE: PRT
<213> ORGANISM: Homo sapiens

<400> SEQUENCE: 1

Met Asp Ser Ser Ala Ala Pro Thr Asn Ala Ser Asn Cys Thr Asp Ala
1               5                   10                  15
```

Leu Ala Tyr Ser Ser Cys Ser Pro Ala Pro Ser Pro Gly Ser Trp Val
                20                  25                  30

Asn Leu Ser His Leu Asp Gly Asn Leu Ser Asp Pro Cys Gly Pro Asn
            35                  40                  45

Arg Thr Asp Leu Gly Gly Arg Asp Ser Leu Cys Pro Pro Thr Gly Ser
        50                  55                  60

Pro Ser Met Ile Thr Ala Ile Thr Ile Met Ala Leu Tyr Ser Ile Val
65                  70                  75                  80

Cys Val Val Gly Leu Phe Gly Asn Phe Leu Val Met Tyr Val Ile Val
                85                  90                  95

Arg Tyr Thr Lys Met Lys Thr Ala Thr Asn Ile Tyr Ile Phe Asn Leu
            100                 105                 110

Ala Leu Ala Asp Ala Leu Ala Thr Ser Thr Leu Pro Phe Gln Ser Val
        115                 120                 125

Asn Tyr Leu Met Gly Thr Trp Pro Phe Gly Thr Ile Leu Cys Lys Ile
130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
        195                 200                 205

Thr Thr Lys Tyr Arg Gln Gly Ser Ile Asp Cys Thr Leu Thr Phe Ser
210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Thr Val Cys Tyr Gly Leu
                245                 250                 255

Met Ile Leu Arg Leu Lys Ser Val Arg Met Leu Ser Gly Ser Lys Glu
            260                 265                 270

Lys Asp Arg Asn Leu Arg Arg Ile Thr Arg Met Val Leu Val Val Val
        275                 280                 285

Ala Val Phe Ile Val Cys Trp Thr Pro Ile His Ile Tyr Val Ile Ile
290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
                325                 330                 335

Leu Tyr Ala Phe Leu Asp Glu Asn Phe Lys Arg Cys Phe Arg Glu Phe
            340                 345                 350

Cys Ile Pro Thr Ser Ser Asn Ile Glu Gln Gln Asn Ser Thr Arg Ile
        355                 360                 365

Arg Gln Asn Thr Arg Asp His Pro Ser Thr Ala Asn Thr Val Asp Arg
370                 375                 380

Thr Asn His Gln Leu Glu Asn Leu Glu Ala Glu Thr Ala Pro Leu Pro
385                 390                 395                 400

<210> SEQ ID NO 2
<211> LENGTH: 369
<212> TYPE: PRT
<213> ORGANISM: Homo sapiens

<400> SEQUENCE: 2

Met Asp Met Ala Asp Glu Pro Leu Asn Gly Ser His Thr Trp Leu Ser
1               5                   10                  15

Ile Pro Phe Asp Leu Asn Gly Ser Val Val Ser Thr Asn Thr Ser Asn
                20                  25                  30

Gln Thr Glu Pro Tyr Tyr Asp Leu Thr Ser Asn Ala Val Leu Thr Phe
            35                  40                  45

Ile Tyr Phe Val Val Cys Ile Ile Gly Leu Cys Gly Asn Thr Leu Val
50                  55                  60

Ile Tyr Val Ile Leu Arg Tyr Ala Lys Met Lys Thr Ile Thr Asn Ile
65                  70                  75                  80

Tyr Ile Leu Asn Leu Ala Ile Ala Asp Glu Leu Phe Met Leu Gly Leu
                85                  90                  95

Pro Phe Leu Ala Met Gln Val Ala Leu Val His Trp Pro Phe Gly Lys
                100                 105                 110

Ala Ile Cys Arg Val Val Met Thr Val Asp Gly Ile Asn Gln Phe Thr
            115                 120                 125

Ser Ile Phe Cys Leu Thr Val Met Ser Ile Asp Arg Tyr Leu Ala Val
130                 135                 140

Val His Pro Ile Lys Ser Ala Lys Trp Arg Arg Pro Arg Thr Ala Lys
145                 150                 155                 160

Met Ile Thr Met Ala Val Trp Gly Val Ser Leu Leu Val Ile Leu Pro
                165                 170                 175

Ile Met Ile Tyr Ala Gly Leu Arg Ser Asn Gln Trp Gly Arg Ser Ser
                180                 185                 190

Cys Thr Ile Asn Trp Pro Gly Glu Ser Gly Ala Trp Tyr Thr Gly Phe
            195                 200                 205

Ile Ile Tyr Thr Phe Ile Leu Gly Phe Leu Val Pro Leu Thr Ile Ile
210                 215                 220

Cys Leu Cys Tyr Leu Phe Ile Ile Lys Val Lys Ser Ser Gly Ile
225                 230                 235                 240

Arg Val Gly Ser Ser Lys Arg Lys Ser Glu Lys Lys Val Thr Arg
                245                 250                 255

Met Val Ser Ile Val Val Ala Val Phe Ile Phe Cys Trp Leu Pro Phe
                260                 265                 270

Tyr Ile Phe Asn Val Ser Ser Val Ser Met Ala Ile Ser Pro Thr Pro
            275                 280                 285

Ala Leu Lys Gly Met Phe Asp Phe Val Val Val Leu Thr Tyr Ala Asn
            290                 295                 300

Ser Cys Ala Asn Pro Ile Leu Tyr Ala Phe Leu Ser Asp Asn Phe Lys
305                 310                 315                 320

Lys Ser Phe Gln Asn Val Leu Cys Leu Val Lys Val Ser Gly Thr Asp
                325                 330                 335

Asp Gly Glu Arg Ser Asp Ser Lys Gln Asp Lys Ser Arg Leu Asn Glu
            340                 345                 350

Thr Thr Glu Thr Gln Arg Thr Leu Leu Asn Gly Asp Leu Gln Thr Ser
                355                 360                 365

Ile

<210> SEQ ID NO 3
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 3

Met Asp Ser Ser Ala Ala Pro Thr Asn Ala Ser Asn Cys Thr Asp Ala
1               5                   10                  15

Leu Ala Tyr Ser Ser Cys Ser Pro Ala Pro Ser Pro Gly Ser Trp Val
            20                  25                  30

Asn Leu Ser His Leu Asp Gly Asn Leu Ser Asp Pro Cys Gly Pro Asn
        35                  40                  45

Arg Thr Asp Leu Gly Gly Arg Asp Ser Leu Cys Pro
    50                  55                  60

<210> SEQ ID NO 4
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 4

Met Asp Met Ala Asp Glu Pro Leu Asn Gly Ser His Thr Trp Leu Ser
1               5                   10                  15

Ile Pro Phe Asp Leu Asn Gly Ser Val Val Ser Thr Asn Thr Ser Asn
            20                  25                  30

Gln Thr Glu Pro
        35

<210> SEQ ID NO 5
<211> LENGTH: 35
<212> TYPE: PRT
<213> ORGANISM: Artificial Sequence
<220> FEATURE:
<223> OTHER INFORMATION: Synthetic polypeptide

<400> SEQUENCE: 5

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn
        35

<210> SEQ ID NO 6
<211> LENGTH: 49
<212> TYPE: PRT
<213> ORGANISM: Artificial Sequence
<220> FEATURE:
<223> OTHER INFORMATION: Synthetic polypeptide

<400> SEQUENCE: 6

Phe Cys Ile Pro Thr Ser Ser Asn Ile Glu Gln Gln Asn Ser Thr Arg
1               5                   10                  15

Ile Arg Gln Asn Thr Arg Asp His Pro Ser Thr Ala Thr Val Asp
            20                  25                  30

Arg Thr Asn His Gln Leu Glu Asn Leu Glu Ala Glu Thr Ala Pro Leu
        35                  40                  45

Pro

<210> SEQ ID NO 7
<211> LENGTH: 43
<212> TYPE: PRT
<213> ORGANISM: Artificial Sequence
<220> FEATURE:
<223> OTHER INFORMATION: Synthetic polypeptide

<400> SEQUENCE: 7

Leu Cys Leu Val Lys Val Ser Gly Thr Asp Asp Gly Glu Arg Ser Asp
1               5                   10                  15

Ser Lys Gln Asp Lys Ser Arg Leu Asn Glu Thr Thr Glu Thr Gln Arg
            20                  25                  30

Thr Leu Leu Asn Gly Asp Leu Gln Thr Ser Ile
        35                  40

<210> SEQ ID NO 8
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 8

Leu Thr Ser Val Ser Arg Gly Ser Ser Leu Lys Ile Leu Ser Lys Gly
1               5                   10                  15

Lys Arg Gly Gly His Ser Ser Val Ser Thr Glu Ser Glu Ser Ser Ser
            20                  25                  30

Phe His Ser Ser
        35

<210> SEQ ID NO 9
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 9
ttactttatg tgttactac                                                19

<210> SEQ ID NO 10
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 10
taaatgacaa gtgtgttgc                                                19

<210> SEQ ID NO 11
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 11
atctatgcat aaacagctg                                                19

<210> SEQ ID NO 12
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 12
acctggtcat cttgttcga                                                    19

<210> SEQ ID NO 13
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 13
aagtcctctg gaatccgagt                                                   20

<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 14
gaggacattc tggaagctct                                                   20

<210> SEQ ID NO 15
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 15
tctggctcca agaaaagga                                                    20

<210> SEQ ID NO 16
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 16
caatgcagaa gtgccaagaa                                                   20

<210> SEQ ID NO 17
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 17
gacgccaaca tagaccacct                                                   20

<210> SEQ ID NO 18
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 18
ccgtggcaaa ctggtacttt                                                   20

<210> SEQ ID NO 19
<211> LENGTH: 20
<212> TYPE: DNA
<213> ORGANISM: Artificial Sequence

```
<220> FEATURE:
<223> OTHER INFORMATION: Synthetic polynucleotide

<400> SEQUENCE: 19
tacaggaagc tgctggaagg                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 20
accagaggga gtgaatccag                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 21
ggccaggaaa tcacatccta                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 22
ggcagtgtct ctccaaatcc                                              20

<210> SEQ ID NO 23
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 23
ctccatgtgc cggatagc                                                18

<210> SEQ ID NO 24
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 24
cgatttcacc agaagcctct ac                                           22

<210> SEQ ID NO 25
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 25
gaaccaatct caccgacagg                                              20
```

```
<210> SEQ ID NO 26
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 26
gccacccgag tgtaaccata                                          20

<210> SEQ ID NO 27
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 27
gtcgagccct aactgcaag                                           19

<210> SEQ ID NO 28
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 28
acaaacactt tgcggtcctt c                                        21
```